United States Patent
Jain et al.

(10) Patent No.: US 8,278,482 B2
(45) Date of Patent: *Oct. 2, 2012

(54) ANTIMICROBIAL N-CHLORINATED COMPOSITIONS

(75) Inventors: Rakesh K. Jain, Fremont, CA (US); Eddy Low, Foster City, CA (US); Charles Francavilla, Fremont, CA (US); Timothy P. Shiau, Oakland, CA (US); Satheesh K. Nair, Emeryville, CA (US)

(73) Assignee: Novabay Pharmaceuticals, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/614,347

(22) Filed: Nov. 6, 2009

(65) Prior Publication Data

US 2010/0158818 A1 Jun. 24, 2010

Related U.S. Application Data

(60) Provisional application No. 61/112,674, filed on Nov. 7, 2008.

(51) Int. Cl.
*C07F 9/02* (2006.01)
*C07C 291/00* (2006.01)
*C07D 295/00* (2006.01)
*C07D 211/00* (2006.01)
*C07D 213/00* (2006.01)
*A61K 31/66* (2006.01)
*A61K 31/535* (2006.01)
*A61K 31/44* (2006.01)
*A61K 31/13* (2006.01)

(52) U.S. Cl. .......... 564/15; 564/114; 564/117; 564/120; 544/106; 546/246; 546/329; 514/75; 514/231.2; 514/357; 514/612

(58) Field of Classification Search .................. None
See application file for complete search history.

(56) References Cited

U.S. PATENT DOCUMENTS

| 4,092,420 | A |  | 5/1978 | Kaminski et al. |  |
|---|---|---|---|---|---|
| 5,026,490 | A | * | 6/1991 | Peiffer et al. | 507/125 |
| 6,451,761 | B1 |  | 9/2002 | van Gelder et al. |  |
| 7,846,971 | B2 |  | 12/2010 | Najafi et al. |  |
| 7,893,109 | B2 |  | 2/2011 | Bassiri et al. |  |
| 2010/0076089 | A1 | * | 3/2010 | Wang et al. | 514/665 |
| 2010/0272783 | A1 | * | 10/2010 | Wang et al. | 424/447 |
| 2011/0151025 | A1 | * | 6/2011 | Gottardi et al. | 424/720 |
| 2011/0190392 | A1 | * | 8/2011 | Najafi et al. | 514/517 |

* cited by examiner

*Primary Examiner* — Kamal Saeed
*Assistant Examiner* — Nyeemah A Grazier
(74) *Attorney, Agent, or Firm* — Hamilton DeSanctis & Cha LLP

(57) ABSTRACT

The present application relates to N-chlorinated cationic compounds of Formula I

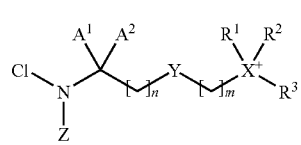

or a salt thereof, and associated compositions and methods of use as antimicrobial agents.

25 Claims, No Drawings

ANTIMICROBIAL N-CHLORINATED COMPOSITIONS

RELATED APPLICATIONS

This application claims the benefit of U.S. Provisional Application No. 61/112,674, filed on Nov. 7, 2008, which is incorporated by reference herein in its entirety.

FIELD

The present application relates to N-halogenated and N,N-dihalogenated cationic compounds, and associated compositions and methods of use as antimicrobial agents.

BACKGROUND

Halogens and halogenating agents have long been used as disinfectants, antiseptics and antimicrobials [see, e.g., G. F. Connell, *The Chlorination/Chloramination Handbook*, Am. Water Works Assn. (1996); H. W. Banks, U.S. Pat. No. 1,813,109; and F. C. Schmelkes, U.S. Pat. No. 1,958,370]. While effectively killing bacteria, fungi and viruses, many chlorinating agents are also toxic to mammalian cells [see, e.g., I. U. Schraufstatter et al., *J. Clin. Invest.* 85, 554-562 (1990)], which can limit their use in therapeutic applications.

Various N-chloro- and N,N-dichloroamino compounds are known. For example, Kaminski et al. (U.S. Pat. No. 4,092,420) discloses N-chloro- and N,N-dichloroamino alcohol derivatives. Gelder et al. (U.S. Pat. No. 6,451,761) discloses N,N-dichloroamino sulfonic, phosphonic and carboxylic acids for the treatment of central nervous system disorders. Bassiri et al. (U.S. Pat. No. 7,462,361) discloses N,N-dihaloamino acids and Najafi et al. (U.S. Patent Publication No. 2006/0247209) discloses various N-halo- and N,N-dihaloamino acids.

Despite these known compounds, other compounds with favorable antimicrobial, stability, water solubility, and other properties, are still needed.

SUMMARY

In one embodiment, the present application describes compounds useful as anti-microbial agents, including as antibacterial, anti-infective, disinfectant, antifungal, germicidal or antiviral agents.

The compounds of this application are represented by the following general structure (Formula I):

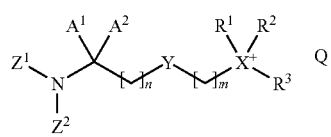

or a salt thereof, wherein:
n is an integer from 0 to 12;
m is an integer from 1 to 12;
$Z^1$ and $Z^2$ are independently H, Cl or Br;
Y is a single bond, —O—, —$CF_2$—, —CHF—, —C($CF_3$)H—, —C(=O)—, —C(=O)O—, —OC(=O)—, —C(=O)$NR^a$—, —$NR^a$—, —$N^+R^aR^b$—, —$NR^aC$(=O)—, —P(=O)($OR^b$)O—, —OP(=O)($OR^b$)—, —P(=O)($OR^b$)$NR^c$—, —$NR^cP$(=O)($OR^b$)—, —S—, —S(=O)—, —S(=O)$_2$—, —S(=O)$_2$O—, —OS(=O)$_2$—, —S(=O)$_2NR^d$—, —$NR^d$S(=O)$_2$— or heteroaryl;
X is N, P or S;
$A^1$ and $A^2$ are each independently selected from the group consisting of alkyl, aryl, cycloalkyl, heteroalkyl, heteroaryl and heterocycloalkyl, each of which may be optionally substituted; or $A^1$ and $A^2$ together with the carbon atom to which they are attached form a cycloalkyl or heterocycloalkyl group, each of which may be optionally substituted;
$R^1$ and $R^2$ are each independently selected from the group consisting of alkyl, aryl, cycloalkyl, heteroalkyl, heteroaryl and heterocycloalkyl, each of which may be optionally substituted; or W and $R^2$ together with the X atom to which they are attached form an optionally substituted heterocycloalkyl group;
$R^3$ is alkyl, aryl, cycloalkyl, heteroalkyl, heteroaryl or heterocycloalkyl, each of which may be optionally substituted, and may further be O when X is N;
$R^a$, $R^b$, $R^c$ and $R^d$ are each independently selected from the group consisting of hydrogen, alkyl, aryl, cycloalkyl, heteroalkyl, heteroaryl and heterocycloalkyl, each of which may be optionally substituted; and
Q is a counter ion or absent;
with the proviso that $R^3$ is absent when X is S.

Processes useful for the preparation of the compounds, compositions comprising the compounds, methods for the prevention and treatment of microbial infections including bacterial, fungal and viral infections in mammals using the compounds and compositions of the disclosure, and use of the compounds and compositions in methods to disinfect tissues (including skin and mucous membranes), medical devices and instruments, and others are also described.

Other aspects of the application may be apparent to one skilled in the art upon reading the following specification and claims.

DETAILED DESCRIPTION

This application is not limited to particular methodologies (e.g., modes of administration) or the specific compositions described, as such may, of course, vary. It is also to be understood that the terminology used herein is for the purpose of describing particular embodiments only, and is not intended to be limiting, since the scope of the present application will be limited only by the appended claims and their equivalents.

Unless defined otherwise, all technical and scientific terms used herein have the same meaning as commonly understood by one of ordinary skill in the art to which this application belongs. It must be noted that as used herein and in the appended claims, the singular forms "a", "and", and "the" include plural referents unless the context clearly dictates otherwise. Thus, e.g., reference to "the compound" includes a plurality of such compounds and reference to "the assay" includes reference to one or more assays and equivalents thereof known to those skilled in the art, and so forth. Also, a divalent group, such as a divalent "alkyl" group, a divalent "aryl" group, etc., may also be referred to as an "alkylene" group or an "alkylenyl" group, an "arylene" group or an "arylenyl" group, respectively.

As utilized in accordance with the present disclosure, the following terms, unless otherwise indicated, shall be understood to have the following meanings:

"Alkyl" refers to a saturated, branched, or straight-chain hydrocarbon radical derived by the removal of one hydrogen atom from a single carbon atom of a parent alkane. Alkyl groups include, but are not limited to, methyl; ethyl; propyls such as propan-1-yl, propan-2-yl (iso-propyl), cyclopropan-1-yl, etc.; butyls such as butan-1-yl, butan-2-yl (sec-butyl), 2-methyl-propan-1-yl (iso-butyl), 2-methyl-propan-2-yl (t-butyl), cyclobutan-1-yl; pentyls; hexyls; octyls; dodecyls; octadecyls; and the like. An alkyl group comprises from 1 to about 22 carbon atoms, e.g., from 1 to 22 carbon atoms, e.g. from 1 to 12 carbon atoms, or, e.g., from 1 to 6 carbon atoms.

"Alkylcycloalkyl" refers to an alkyl group attached to a cycloalkyl group. Alkylcycloalkyl groups include, but are not limited to, methyl cyclopentyl, methyl cyclobutyl, ethyl cyclohexyl, and the like. An alkylcycloalkyl group comprises from 4 to about 32 carbon atoms, i.e. the alkyl group can comprise from 1 to about 22 carbon atoms and the cycloalkyl group can comprise from 3 to about 10 carbon atoms.

"Active ingredient" refers to a compound of Formula I, or a salt thereof.

"Acyl" refers to a radical —C(=O)R, where R is hydrogen, alkyl, cycloalkyl, cycloheteroalkyl, aryl, arylalkyl, heteroalkyl, heteroaryl, or heteroarylalkyl as defined herein, each of which may be optionally substituted, as defined herein. Representative examples include, but are not limited to formyl, acetyl, cylcohexylcarbonyl, cyclohexylmethylcarbonyl, benzoyl, benzylcarbonyl and the like.

"Acylamino" (or alternatively "acylamido") refers to a radical —NR'C(=O)R, where R' and R are each independently hydrogen, alkyl, cycloalkyl, cycloheteroalkyl, aryl, arylalkyl, heteroalkyl, heteroaryl, or heteroarylalkyl, as defined herein, each of which may be optionally substituted, as defined herein. Representative examples include, but are not limited to, formylamino, acetylamino (i.e., acetamido), cyclohexylcarbonylamino, cyclohexylmethyl-carbonylamino, benzoylamino (i.e., benzamido), benzylcarbonylamino and the like.

"Acyloxy" refers to a radical —OC(=O)R, where R is hydrogen, alkyl, cycloalkyl, cycloheteroalkyl, aryl, arylalkyl, heteroalkyl, heteroaryl or heteroarylalkyl, as defined herein, each of which may be optionally substituted, as defined herein. Representative examples include, but are not limited to, acetyloxy (or acetoxy), butanoyloxy, benzoyloxy and the like.

"Alkoxy" refers to a radical —OR where R represents an alkyl or cycloalkyl group as defined herein, each of which may be optionally substituted, as defined herein. Representative examples include, but are not limited to, methoxy, ethoxy, propoxy, butoxy, cyclohexyloxy and the like.

"Alkoxycarbonyl" refers to a radical —C(=O)-alkoxy where alkoxy is as defined herein.

"Alkylsulfonyl" refers to a radical —S(=O)$_2$R where R is an alkyl or cycloalkyl group as defined herein, each of which may be optionally substituted, as defined herein. Representative examples include, but are not limited to, methylsulfonyl, ethylsulfonyl, propylsulfonyl, butylsulfonyl and the like.

"Aryl" refers to an aromatic hydrocarbon group which may be a single aromatic ring or multiple aromatic rings which are fused together, linked covalently, or linked to a common group such as a methylene or ethylene moiety. Aryl groups include, but are not limited to, groups derived from acenaphthylene, anthracene, azulene, benzene, biphenyl, chrysene, cyclopentadiene, diphenylmethyl, fluoranthene, fluorene, indane, indene, naphthalene, pentalene, perylene, phenalene, phenanthrene, pyrene, triphenylene, and the like. An aryl group comprises from 5 to about 20 carbon atoms, e.g., from 6 to 20 carbon atoms, e.g. from 5 to 10 carbon atoms.

"Arylalkyl" refers to an aryl group attached to an alkyl group. Arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl may be used. An arylalkyl group comprises from 7 to about 42 carbon atoms, e.g. the alkyl group can comprise from 1 to about 22 carbon atoms and the aryl group can comprise from 6 to about 20 carbon atoms.

"Carbamoyl" refers to the radical —OC(=O)N(R)$_2$ where each R group is independently hydrogen, alkyl, cycloalkyl or aryl as defined herein, which may be optionally substituted, as defined herein.

"Carbonate" refers to the group —CO$_3^{2-}$.

"Compounds" as used herein refers to any of the compounds encompassed by Formula I as disclosed herein. The compounds may be neutral, charged (e.g. cationic or anionic), or in a salt form. The compounds may be identified by structure or by name. If the chemical structure and chemical name conflict, the chemical structure will be determinative of the identity of the compound. The compounds may contain one or more chiral centers and/or double bonds and therefore, may exist as stereoisomers, such as double-bond isomers (i.e., geometric isomers), enantiomers or diastereomers. Accordingly, when stereochemistry at chiral centers is not specified, the chemical structures depicted herein encompass all possible configurations at those chiral centers including the stereoisomerically pure form (e.g., geometrically pure, enantiomerically pure or diastereomerically pure) and enantiomeric and stereoisomeric mixtures. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds also include isotopically labeled compounds where one or more atoms have an atomic mass different from the atomic mass conventionally found in nature. Examples of isotopes that may be incorporated into the compounds include, but are not limited to, $^2$H, $^3$H, $^{13}$C, $^{14}$C, $^{15}$N, $^{17}$O, $^{18}$O, $^{18}$F, $^{31}$P, $^{32}$P, $^{35}$S and $^{36}$Cl. Compounds may exist in unsolvated forms as well as solvated forms, including hydrated forms and as N-oxides. In general, the neutral, charged, protonated, salt, hydrated, solvated and N-oxide forms are within the scope of the present disclosure.

"Cycloalkyl" refers to a saturated or unsaturated cyclic alkyl radical. Typical cycloalkyl groups include, but are not limited to, groups derived from cyclopropane, cyclobutane, cyclopentane, cyclohexane, cyclohexene, 1,3-cyclohexadiene, and the like. A cycloalkyl group comprises from 3 to about 10 carbon atoms, e.g. from 3 to 10 carbon atoms, or, e.g. from 3 to 6 carbon atoms.

"Effective amount" means the amount of a compound that, when administered to a subject, surface or area for treating or preventing a microbial infection or contamination, is sufficient to effect such treatment or prevention. The "effective amount" will vary depending on the compound, the severity of the condition causing the microbial infection and the age, weight, etc., of the subject to be treated.

"Electron-withdrawing group" refers to atoms or functional groups which are electronegative either through a resonance effect or an inductive effect. Examples of such atoms and functional groups include, but are not limited to —CO$_2$R$^O$, —CO—, —NO$_2$, —SO$_3$R$^O$, —PO$_3$R$^O$R$^{OO}$, cyano, halogen (F, Cl, Br, I), and haloalkyl (e.g. —CF$_3$), where R$^O$ and R$^{OO}$ are independently H, alkyl, aryl, cycloalkyl, heteroalkyl, heteroaryl or cycloheteroalkyl group, as defined herein, each of which may be optionally and independently substituted.

"Halide" means a halogen bearing a negative charge, including fluoride, chloride, bromide and iodide.

"Halo" means a halogen, including fluoro, chloro, bromo and iodo.

"Heteroalkyl" refer to an alkyl radical in which one or more of the carbon atoms (and any associated hydrogen atoms) are each independently replaced with the same or different heteroatomic groups. Heteroatomic groups include, but are not limited to, —NR$^O$—, —O—, —S—, —PH—, —P(O)$_2$—, —S(O)—, —S(O)$_2$—, and the like, where R$^O$ is defined above. Heteroalkyl groups include, but are not limited to, —O—CH$_3$, —CH$_2$—O—CH$_3$, —S—CH$_3$, —CH$_2$—S—CH$_3$, —NR$^O$—CH$_3$, —CH$_2$—NR$^{OO}$—CH$_3$, and the like, where R$^O$ and R$^{OO}$ are defined above. A heteroalkyl group can comprise from 1 to about 22 carbon and hetero atoms, e.g., from 1 to 22 carbon and heteroatoms, e.g. from 1 to 12 carbon and hetero atoms, e.g., from 1 to 6 carbon and hetero atoms.

"Heteroaryl" refers to an aryl group in which one or more of the carbon atoms (and any associated hydrogen atoms) are each independently replaced with the same or different heteroatomic groups. Typical heteroatomic groups include, but are not limited to, —N—, —O—, —S— and —NR$^O$—, where R$^O$ is defined above. Typical heteroaryl groups include, but are not limited to, groups derived from acridine, carbazole, carboline, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. A heteroaryl group comprises from 5 to about 20 atoms, e.g., from 5 to 20 atoms, e.g. from 5 to 10 atoms.

"Heterocycloalkyl" refers to a saturated or unsaturated cycloalkyl radical in which one or more carbon atoms (and any associated hydrogen atoms) are independently replaced with the same or different heteroatom. Typical heteroatoms to replace the carbon atom(s) include, but are not limited to, N, P, O, S, etc. A heterocycloalkyl group may also contain a charged heteroatom or group, e.g., a quaternized ammonium group such as —N$^+$(R)$_2$— wherein R is alkyl, e.g., methyl, ethyl, etc. Heterocycloalkyl groups include, but are not limited to, groups derived from epoxides, imidazolidine, morpholine, piperazine, piperidine, pyrazolidine, piperidine, pyrrolidine, quinuclidine, N-bromopyrrolidine, N-bromopiperidine, N-chloropyrrolidine, N-chloropiperidine, an N,N-dialkylpyrrolidinium, such as N,N-dimethylpyrrolidinium, a N,N-dialkylpiperidinium such as N,N-dimethylpiperidium, and the like. The heterocycloalkyl group comprises from 3 to about 10 carbon and hetero atoms in the ring.

"Microbial" refers to bacteria, fungi (including, e.g., yeast) or virus, and any associated biofilm.

"Pharmaceutically acceptable" rerers to that which is useful in preparing a pharmaceutical composition that is generally safe, non-toxic, and neither biologically nor otherwise undesirable, and includes that which is acceptable for veterinary as well as human pharmaceutical use.

"Pharmaceutically acceptable salt" refers to a salt of a compound that is pharmaceutically acceptable and that possesses (or can be converted to a form that possesses) the desired pharmacological activity of the parent compound. Such salts include acid addition salts formed with inorganic acids such as hydrochloric acid, hydrobromic acid, sulfuric acid, nitric acid, phosphoric acid, and the like; or formed with organic acids such as acetic acid, benzenesulfonic acid, benzoic acid, camphorsulfonic acid, citric acid, ethanesulfonic acid, fumaric acid, glucoheptonic acid, gluconic acid, lactic acid, maleic acid, malonic acid, mandelic acid, methanesulfonic acid, 2-napththalenesulfonic acid, oleic acid, palmitic acid, propionic acid, stearic acid, succinic acid, tartaric acid, p-toluenesulfonic acid, trimethylacetic acid, and the like, and salts formed when an acidic proton present in the parent compound is replaced by either a metal ion, e.g., an alkali metal ion, an alkaline earth ion, or an aluminum ion; or coordinates with an organic base such as diethanolamine, triethanolamine, N-methylglucamine and the like. Also included in this definition are ammonium and substituted or quaternized ammonium salts. Representative non-limiting lists of pharmaceutically acceptable salts can be found in S. M. Berge et al., *J. Pharma Sci.*, 66(1), 1-19 (1977), and *Remington: The Science and Practice of Pharmacy*, R. Hendrickson, ed., 21st edition, Lippincott, Williams & Wilkins, Philadelphia, Pa., (2005), at p. 732, Table 38-5, both of which are hereby incorporated by reference herein.

"Pharmaceutically acceptable carrier" refers to a pharmaceutically acceptable diluent, adjuvant, excipient or vehicle and the like with which a compound is combined and/or administered.

"Pharmaceutical composition" as used herein comprises one or more compounds of Formula I and a pharmaceutically acceptable carrier.

"Phosphate" refers to the group $(R)_n PO_4^{(3-n)}$— where n is 0, 1 or 2 and R can be hydrogen, alkyl, aryl, cycloalkyl, heteroalkyl, or heteroaryl as defined herein, each of which may be optionally substituted.

"Prevent", "preventing" and "prevention" of a microbial infection refer to reducing the risk of a subject from developing a microbial infection, or reducing the frequency or severity of a microbial infection in a subject.

"Protecting group" refers to a group of atoms that when attached to a reactive functional group in a molecule masks, reduces or prevents reactivity of the functional group. Examples of protecting groups can be found in P. G. M. Wuts and T. W. Greene, *Greene's Protective Groups in Organic Synthesis* (4th Ed.), Wiley-Interscience, (2006), and Harrison et al., *Compendium of Synthetic Organic Methods*, Vols. 1-8 (John Wiley and Sons, 1971-1996). For example, representative amino protecting groups include, but are not limited to, formyl, acetyl, trifluoroacetyl, benzyl, benzyloxycarbonyl ("CBZ", "Cbz"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Salt" refers to a cation coupled with an anion, either in solution or as a solid. Salts include pharmaceutically acceptable salts as well as solvent addition forms (solvates) of the same salt.

"Subject" refers to an animal (including, but not limited to, a bull, steer, cow, horse, dog, cat, bird, reptile, monotreme, etc.), including a human.

"Sulfate" refers to the group $SO_4^{-2}$.

"Substituted" refers to a group wherein one or more hydrogens (e.g., from 1 to 5, e.g., from 1 to 3) have been replaced with one or more substituents including, but not limited to, acylamino, alkoxy, alkyl, amino, amidino, aryl, carboxyl, carbamoyl, cyano, cycloalkyl, guanidino, halo, heteroalkyl, heteroaryl, heterocycloalkyl, hydroxyl, imidino, imino, nitro, oxamidino, oxo, methoxamidino, sulfonamido, thio, thioamido, any electron-withdrawing group, or a combination thereof.

"Treat", "treating" and "treatment" of a microbial infection or contamination refer to reducing the frequency or severity of symptoms of a microbial infection (including eliminating them), or avoiding or reducing the chances of the occurrence of a microbial infection, or killing or inhibiting the growth of bacteria, fungus or virus.

The following abbreviations may also be used: APCI: atmospheric pressure chemical ionization; b: broad (NMR); bd: broad doublet (NMR); $BH_3$-$Me_2S$: borane dimethyl sulfide complex; $Boc_2O$: di-tert-butyl dicarbonate; b.p.: boiling point; $CbzOSu$: N-carbobenzoxysuccinimide; CDI: N,N'-carbonyldiimidazole; Cmpd: compound; d: doublet; dd: doublet of doublet; DCM: dichloromethane; DCE: 1,2-dichloroethane; DIAD: diisopropylazodicarboxylate; DIEA: diisopropylethylamine; DPPA: diphenylphosphoryl azide; DMF: N,N-dimethylformamide; EA, EtOAc: ethyl acetate; EDT: ethanedithiol; ESI+: electrospray ionization (positive mode); ESI−: electrospray ionization (negative mode); EtOH: ethanol; h: hour; HATU: O-(7-azabenzotriazol-1-yl)-N,N,N',N'-tetramethyluronium hexafluorophosphate; HOBT, HOBt: 1-hydroxybenzotriazole hydrate; HPLC: high pressure liquid chromatography; ISCO: normal phase flash chromatophy (e.g. using Teledyne®-ISCO® instrument); LAH: lithium aluminium hydride; LCMS: high pressure liquid chromatography with mass spectrometer detector; LRMS: low resolution mass spectrometer; M+H+, $MH^+$: molecular weight plus the weight of one proton; m: multiplet (NMR); MCPBA: 3-chloroperoxybenzoic acid; MeOH: methanol; min.: minutes; MS: mass spectrometer; m/z: mass to charge ratio; NMR: nuclear magnetic resonance; Pd/C: 10% palladium on carbon; PTFE: polytetrafluoroethylene; pos: positive; quant: quantitive; rotovap: rotary evaporator; RT, rt: room temperature; s: singlet (NMR); sat.: saturated; sext.: sextet (NMR); t: triplet (NMR); t-BuOCl: tert-butylhypochlorite; TEA: triethylamine; TFA: trifluoroacetic acid; THF: tetrahydrofuran; TLC: thin layer chromatography; UV, uv: ultraviolet. Other abbreviations commonly used in the art may also be used.

One aspect of the current disclosure relates to compounds of Formula I

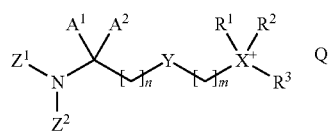

or a salt thereof, wherein:
n is an integer from 0 to 12;
m is an integer from 1 to 12;
$Z^1$ and $Z^2$ are independently H, Cl or Br;
Y is a single bond, —O—, —$CF_2$—, —CHF—, —C($CF_3$)H—, —C(=O)—, —C(=O)O—, —OC(=O)—, —C(=O)NR$^a$—, —N$^+$R$^a$R$^b$, —NR$^a$C(=O)—, —P(=O)(OR$^b$)O—, —OP(=O)(OR$^b$)—, —P(=O)(OR$^b$)NR$^c$—, —NR$^c$P(=O)(OR$^b$)—, —S—, —S(=O)—, —S(=O)$_2$—, —S(=O)$_2$O—, —OS(=O)$_2$—, —S(=O)$_2$NR$^d$—, —NR$^d$S(=O)$_2$— or heteroaryl;

X is N, P, or S;
$A^1$ and $A^2$ are each independently selected from the group consisting of alkyl, aryl, cycloalkyl, heteroalkyl, heteroaryl, and heterocycloalkyl, each of which may be optionally substituted; or $A^1$ and $A^2$ together with the carbon atom to which they are attached form a cycloalkyl or heterocycloalkyl group, each of which may be optionally substituted;
$R^1$ and $R^2$ are each independently selected from the group consisting of alkyl, aryl, cycloalkyl, heteroalkyl, heteroaryl and heterocycloalkyl, each of which may be optionally substituted; or $R^1$ and $R^2$ together with the X atom to which they are attached form an optionally substituted heterocycloalkyl group;
$R^3$ is alkyl, aryl, cycloalkyl, heteroalkyl, heteroaryl, or heterocycloalkyl, each of which may be optionally substituted, and may further be O when X is N;
$R^a$, $R^b$, $R^c$ and $R^d$ are each independently selected from the group consisting of hydrogen, alkyl, aryl, cycloalkyl, heteroalkyl, heteroaryl and heterocycloalkyl, each of which may be optionally substituted; and
Q is a counter ion or absent;
with the proviso that $R^3$ is absent when X is S.

In certain compounds of Formula I, n is 1, 2 or 3.
In certain compounds of Formula I, m is 1, 2 or 3.
In certain compounds of Formula I, $Z^1$ and $Z^2$ are independently H or Cl. In certain compounds of Formula I, $Z^1$ and $Z^2$ are both H. In other compounds of Formula I, $Z^1$ is Cl. In yet other compounds of Formula I, $Z^1$ is Cl and $Z^2$ is H. In yet other compounds of Formula I, $Z^1$ and $Z^2$ are both Cl.

In certain compounds of Formula I, Y is a single bond. In other compounds of Formula I, Y is —O—, —$CF_2$—, —CHF—, —C($CF_3$)H—, —C(=O)—, —C(=O)O—, —OC(=O)—, —C(=O)NR$^a$—, —NR$^a$—, —N$^+$R$^a$R$^b$, —NR$^a$C(=O)—, —P(=O)(OR$^b$)O—, —OP(=O)(OR$^b$)—, —P(=O)(OR$^b$)NR$^c$—, —NR$^c$P(=O)(OR$^b$)—, —S—, —S(=O)—, S(=O)$_2$—, —S(=O)$_2$O—, —OS(=O)$_2$—, —S(=O)$_2$NR$^d$— or —NR$^d$S(=O)$_2$—. In yet other compounds of Formula I, Y is heteroaryl. In certain compounds of Formula I, Y is triazole or tetrazole. In certain compounds of Formula I, the triazole can be a 1,2,3-triazole, and the tetrazole can be a 1,2,3,4-tetrazole.

In certain compounds of Formula I, X is N. In other compounds of Formula I, X is P or S.

In certain compounds of Formula I, $A^1$ and $A^2$ are alkyl, each of which may be optionally substituted. For example, $A^1$ and $A^2$ may both be methyl. In other compounds of Formula I, $A^1$ and $A^2$ together with the carbon atom to which they are attached form a cycloalkyl or heterocycloalkyl, each of which may be optionally substituted.

In certain compounds of Formula I, $R^1$, $R^2$ and $R^3$ are each independently selected from the group consisting of alkyl and aryl, each of which may be optionally substituted. In other compounds of Formula I, $R^1$ and $R^2$ together with the X atom to which they are attached form an optionally substituted heterocycloalkyl, and $R^3$ is optionally substituted alkyl or aryl.

In certain compounds of Formula I, at least one of $R^1$, $R^2$ and $R^3$ is substituted with one or more electron withdrawing groups. In certain compounds of Formula I, the electron-withdrawing group is a halo group (e.g. F), haloalkyl (e.g. —$CF_3$), or a sulfonic acid group. In certain compounds of Formula I, one or more of $A^1$ and $A^2$ may be substituted with one or more electron withdrawing groups. In certain compounds of Formula I, these electron-withdrawing groups can be a halo group (e.g. F), haloalkyl (e.g. —$CF_3$), or a sulfonic acid group.

In certain compounds of Formula I, $R^1$, $R^2$ and $R^3$ are alkyl.

Compounds of Formula I may further comprise one or more counter ions. Counter ions may be those of any salt (e.g. of a pharmaceutically acceptable salt), including, without limitation, carbonate, carboxylate, halide (e.g. chloride), hydroxide, sulfate, sulfonate, acetate, succinate, formate, methylsulfonate or phosphate. In certain compounds of Formula I, Q is a counter ion. In other compounds of Formula I, Q is absent; that is, certain compounds of Formula I may be zwitterions.

In certain compounds, the salt may be a pharmaceutically acceptable salt.

Another aspect of the current disclosure relates to compounds of Formula IA

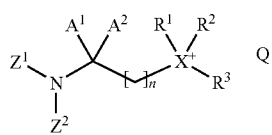

IA or a salt thereof, wherein:
n is an integer from 0 to 12;
$Z^1$ and $Z^2$ are independently H, Cl or Br;
X is N, P or S;
$A^1$ and $A^2$ are each independently selected from the group consisting of alkyl, aryl, cycloalkyl, heteroalkyl, heteroaryl and heterocycloalkyl, each of which may be optionally substituted; or $A^1$ and $A^2$ together with the carbon atom to which they are attached form a cycloalkyl or heterocycloalkyl group, each of which may be optionally substituted;
$R^1$ and $R^2$ are each independently selected from the group consisting of alkyl, aryl, cycloalkyl, heteroalkyl, heteroaryl and heterocycloalkyl, each of which may be optionally substituted; or $R^1$ and $R^2$ together with the X atom to which they are attached form an optionally substituted heterocycloalkyl group;
$R^3$ is alkyl, aryl, cycloalkyl, heteroalkyl, heteroaryl or heterocycloalkyl, each of which may be optionally substituted, and may further be O when X is N; and
Q is a counter ion or absent;
with the proviso that $R^3$ is absent when X is S.

In certain compounds of Formula IA, n is 1, 2 or 3.

In certain compounds of Formula IA, $Z^1$ and $Z^2$ are independently H or Cl. In certain compounds of Formula IA, $Z^1$ and $Z^2$ are both H. In other compounds of Formula IA, $Z^1$ is Cl. In yet other compounds of Formula IA, $Z^1$ is Cl and $Z^2$ is H. In yet other compounds of Formula IA, $Z^1$ and $Z^2$ are both Cl.

In certain compounds of Formula IA, X is N. In other compounds of Formula IA, X is P or S.

In certain compounds of Formula IA, $A^1$ and $A^2$ are alkyl, each of which may be optionally substituted. For example, $A^1$ and $A^2$ may both be methyl. In other compounds of Formula IA, $A^1$ and $A^2$ together with the carbon atom to which they are attached form a cycloalkyl or heterocycloalkyl, each of which may be optionally substituted.

In certain compounds of Formula IA, $R^1$, $R^2$ and $R^3$ are each independently selected from the group consisting of alkyl and aryl, each of which may be optionally substituted. In other compounds of Formula IA, $R^1$ and $R^2$ together with the X atom to which they are attached form an optionally substituted heterocycloalkyl, and $R^3$ is optionally substituted alkyl or aryl.

In certain compounds of Formula IA, at least one of $R^1$, $R^2$ and $R^3$ is substituted with one or more electron withdrawing groups. In certain compounds of Formula IA, the electron-withdrawing group is a halo group (e.g. F), haloalkyl (e.g. —$CF_3$), or a sulfonic acid group. In certain compounds of Formula IA, one or more of $A^1$ and $A^2$ may be substituted with one or more electron withdrawing groups. In certain compounds of Formula IA, these electron-withdrawing groups can be a halo group (e.g. F), haloalkyl (e.g. —$CF_3$), or a sulfonic acid group.

In certain compounds of Formula IA, $R^1$, $R^2$ and $R^3$ are alkyl.

Compounds of Formula IA may further comprise one or more counter ions, as described above. In certain compounds of Formula IA, Q is a counter ion. In other compounds of Formula IA, Q is absent; that is, certain compounds of Formula IA may be zwitterions.

Another aspect of the current disclosure relates to compounds of Formula IB

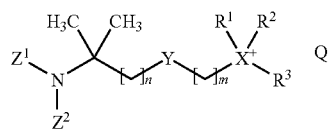

IB or a salt thereof, wherein:
n is an integer from 0 to 12;
m is an integer from 1 to 12;
$Z^1$ and $Z^2$ are independently H, Cl or Br;
Y is a single bond, —O—, —$CF_2$—, —CHF—, —C($CF_3$)H—, —C(=O)—, —C(=O)O—, —OC(=O)—, —C(=O)N$R^a$—, —N$R^a$—, —$N^+R^aR^b$, —N$R^a$C(=O)—, —P(=O)(O$R^b$)O—, —OP(=O)(O$R^b$)—, —P(=O)(O$R^b$)N$R^c$—, —N$R^c$P(=O)(O$R^b$)—, —S—, —S(=O)—, —S(=O)$_2$—, —S(=O)$_2$O—, —OS(=O)$_2$—, —S(=O)$_2$N$R^d$—, —N$R^d$S(=O)$_2$— or heteroaryl;
X is N, P or S;
$R^1$ and $R^2$ are each independently selected from the group consisting of alkyl, aryl, cycloalkyl, heteroalkyl, heteroaryl and heterocycloalkyl, each of which may be optionally substituted; or $R^1$ and $R^2$ together with the X atom to which they are attached form an optionally substituted heterocycloalkyl group;
$R^3$ is alkyl, aryl, cycloalkyl, heteroalkyl, heteroaryl, or heterocycloalkyl, each of which may be optionally substituted, and may further be O when X is N;
$R^a$, $R^b$, $R^c$ and $R^d$ are each independently selected from the group consisting of hydrogen, alkyl, aryl, cycloalkyl, heteroalkyl, heteroaryl and heterocycloalkyl, each of which may be optionally substituted; and
Q is a counter ion or absent;
with the proviso that $R^3$ is absent when X is S.

In certain compounds of Formula IB, n is 1, 2 or 3.

In certain compounds of Formula IB, m is 1, 2 or 3.

In certain compounds of Formula IB, $Z^1$ and $Z^2$ are independently H or Cl. In certain compounds of Formula IB, $Z^1$ and $Z^2$ are both H. In other compounds of Formula IB, $Z^1$ is Cl. In yet other compounds of Formula IB, $Z^1$ is Cl and $Z^2$ is H. In yet other compounds of Formula IB, $Z^1$ and $Z^2$ are both Cl.

In certain compounds of Formula IB, Y is a single bond. In other compounds of Formula I, Y is —O—, —$CF_2$—, —CHF—, —C($CF_3$)H—, —C(=O)—, —C(=O)O—, —OC(=O)—, —C(=O)N$R^a$—, —N$R^a$—$N^+R^aR^b$, —N$R^a$C(=O)—, —P(=O)(O$R^b$)O—, —OP(=O)(O$R^b$)—, —P(=O)(O$R^b$)N$R^c$—, —N$R^c$P(=O)(O$R^b$)—, —S—, —S(=O)—, —S(=O)$_2$—, —S(=O)$_2$O—, —OS(=O)$_2$—, —S(=O)$_2$NR$^d$— or —NR$^d$S(=O)$_2$—. In yet other compounds of Formula IB, Y is heteroaryl. For example, in certain compounds, Y is a single bond, —O—, —CF$_2$—, —CHF—, —C(CF$_3$)H—, —C(=O)—, —C(=O)O—, —OC(=O)—, —C(=O)NR$^a$—, —NR$^a$—, —N$^+$R$^a$R$^b$, —NR$^a$C(=O)—, —S(=O)$_2$—, or heteroaryl. In certain compounds of Formula IB, Y is triazole or tetrazole. In certain compounds of Formula IB, the triazole can be a 1,2,3-triazole, and the tetrazole can be a 1,2,3,4-tetrazole.

In certain compounds of Formula IB, X is N. In other compounds of Formula IB, X is P or S.

In certain compounds of Formula IB, R$^1$, R$^2$ and R$^3$ are each independently selected from the group consisting of alkyl and aryl, each of which may be optionally substituted. In other compounds of Formula IB, R$^1$ and R$^2$ together with the X atom to which they are attached form an optionally substituted heterocycloalkyl, and R$^3$ is optionally substituted alkyl or aryl.

In certain compounds of Formula IB, at least one of R$^1$, R$^2$ and R$^3$ is substituted with one or more electron withdrawing groups. In certain compounds of Formula IB, the electron-withdrawing group is a halo group (e.g. F), haloalkyl (e.g. —CF$_3$), or a sulfonic acid group.

In certain compounds of Formula IB, R$^1$, R$^2$ and R$^3$ are alkyl.

Compounds of Formula IB may further comprise one or more counter ions, as described above. In certain compounds of Formula IB, Q is a counter ion. In other compounds of Formula IA, Q is absent; that is, certain compounds of Formula IB may be zwitterions.

Another aspect of the current disclosure relates to compounds of Formula IC

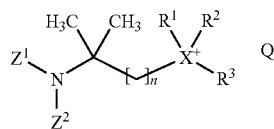

IC or a salt thereof, wherein:

n is an integer from 0 to 12;

Z$^1$ and Z$^2$ are independently H, Cl or Br;

X is N, P, or S;

R$^1$ and R$^2$ are each independently selected from the group consisting of alkyl, aryl, cycloalkyl, heteroalkyl, heteroaryl and heterocycloalkyl, each of which may be optionally substituted; or R$^1$ and R$^2$ together with the X atom to which they are attached form an optionally substituted heterocycloalkyl group;

R$^3$ is alkyl, aryl, cycloalkyl, heteroalkyl, heteroaryl, or heterocycloalkyl, each of which may be optionally substituted, and may further be O when X is N; and Q is a counter ion or absent;

with the proviso that R$^3$ is absent when X is S.

In certain compounds of Formula IC, n is 1, 2 or 3.

In certain compounds of Formula IC, Z$^1$ and Z$^2$ are independently H or Cl. In certain compounds of Formula IC, Z$^1$ and Z$^2$ are both H. In other compounds of Formula IC, Z$^1$ is Cl. In yet other compounds of Formula IC, Z$^1$ is Cl and Z$^2$ is H. In yet other compounds of Formula IC, Z$^1$ and Z$^2$ are both Cl.

In certain compounds of Formula IC, X is N. In other compounds of Formula IC, X is P or S.

In certain compounds of Formula IC, R$^1$, R$^2$ and R$^3$ are each independently selected from the group consisting of alkyl and aryl, each of which may be optionally substituted. In other compounds of Formula IC, R$^1$ and R$^2$ together with the X atom to which they are attached form an optionally substituted heterocycloalkyl, and R$^3$ is optionally substituted alkyl or aryl.

In certain compounds of Formula IC, at least one of R$^1$, R$^2$ and R$^3$ is substituted with one or more electron withdrawing groups. In certain compounds of Formula IC, the electron-withdrawing group is a halo group (e.g. F), haloalkyl (e.g. —CF$_3$), or a sulfonic acid group.

In certain compounds of Formula IC, R$^1$, R$^2$ and R$^3$ are alkyl.

Compounds of Formula IC may further comprise one or more counter ions, as described above. In certain compounds of Formula IC, Q is a counter ion. In other compounds of Formula IC, Q is absent; that is, certain compounds of Formula I may be zwitterions.

In certain compounds of Formula I (which include compounds of Formulae IA, IB and IC), the salt may be a pharmaceutically acceptable salt.

As discussed herein, compounds of Formula I may comprise one or more counter ions. Thus, the specific compounds shown below may be named or depicted with or without a particular counter ion (e.g. chloride or Cl$^-$). It will nevertheless be understood that in such cases, the associated ion or charged species (e.g. anion, cation, di-cation, zwiterion, etc.) and any other salt form (e.g. the corresponding bromide, carbonate, hydroxide, etc.), as well as the particular salt named or depicted, are contemplated and are within the scope of this disclosure. The present application further includes the following compounds, hereby identified by name, structure, and reference number.

TABLE 1

| Name (Compound No.) | Structure |
|---|---|
| 2-(3-(chloroamino)-3-methylbutylsulfonyl)-N,N,N-trimethylethanammonium chloride (21-01) | 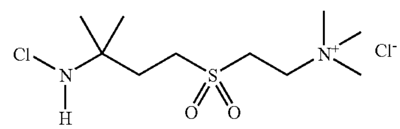 |
| 2-(3-(dichloroamino)-3-methylbutylsulfonyl)-N,N,N-trimethylethanammonium chloride (21-02) | 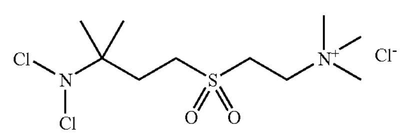 |

TABLE 1-continued

| Name (Compound No.) | Structure |
|---|---|
| 2-(2-(chloroamino)-2-methylpropylsulfonyl)-N,N,N-trimethylethanammonium chloride (21-03) | 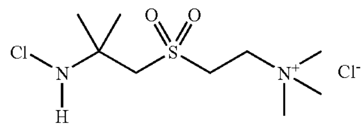 |
| 2-(2-(dichloroamino)-2-methylpropylsulfonyl)-N,N,N-trimethylethanammonium chloride (21-04) | 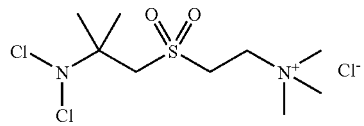 |
| 5-(chloroamino)-N,N,N,5-tetramethyl-3-oxohexan-1-ammonium chloride (21-05) | 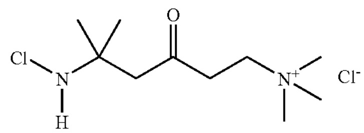 |
| 5-(dichloroamino)-N,N,N,5-tetramethyl-3-oxohexan-1-ammonium chloride (21-06) | 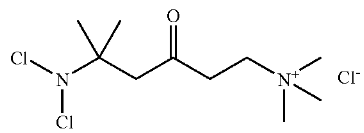 |
| 6-(chloroamino)-N,N,N,6-tetramethyl-3-oxoheptan-1-ammonium chloride (21-07) | 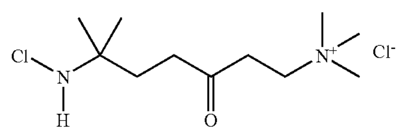 |
| 6-(dichloroamino)-N,N,N,6-tetramethyl-3-oxoheptan-1-ammonium chloride (21-08) | 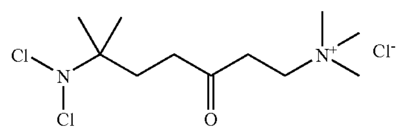 |
| 2-(3-(chloroamino)-3-methylbutanoyloxy)-N,N,N-trimethylethanammonium chloride (21-09) | 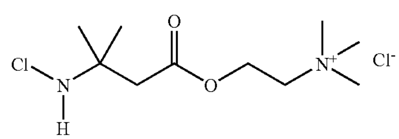 |
| 2-(3-(dichloroamino)-3-methylbutanoyloxy)-N,N,N-trimethylethanammonium chloride (21-10) | 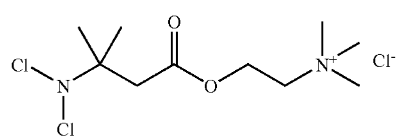 |
| 2-(3-(chloroamino)-3-methylbutanamido)-N,N,N-trimethylethanammonium chloride (21-11) | 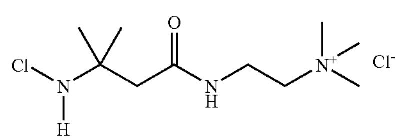 |
| 2-(3-(dichloroamino)-3-methylbutanamido)-N,N,N-trimethylethanammonium chloride (21-12) | 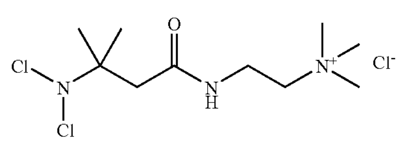 |
| 2-(3-(chloroamino)-N,3-dimethylbutanamido)-N,N,N-trimethylethanammonium chloride (21-13) | 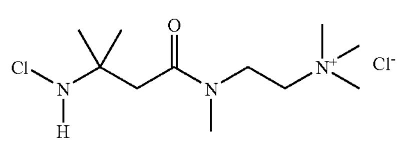 |

TABLE 1-continued

| Name (Compound No.) | Structure |
|---|---|
| 2-(3-(dichloroamino)-N,3-dimethylbutanamido)-N,N,N-trimethylethanammonium chloride (21-14) | 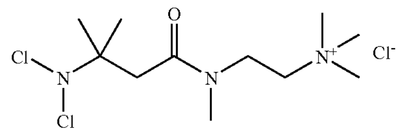 |
| 2-(3-(chloroamino)-3-methylbutylsulfonamido)-N,N,N-trimethylethanammonium chloride (21-15) | 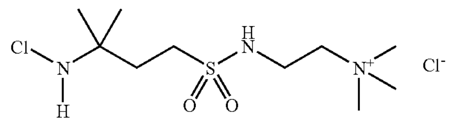 |
| 2-(3-(dichloroamino)-3-methylbutylsulfonamido)-N,N,N-trimethylethanammonium chloride (21-16) | 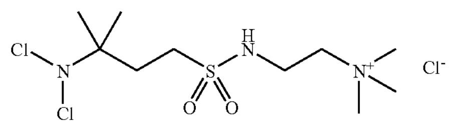 |
| 2-(3-(chloroamino)-N,3-dimethylbutylsulfonamido)-N,N,N-trimethylethanammonium chloride (21-17) | 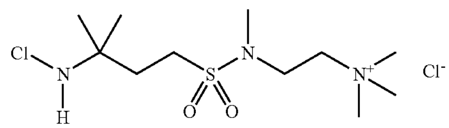 |
| 2-(3-(dichloroamino)-N,3-dimethylbutylsulfonamido)-N,N,N-trimethylethanammonium chloride (21-18) | 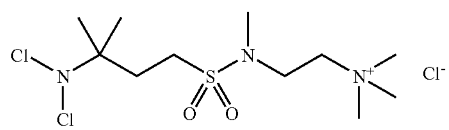 |
| 2-(3-(chloroamino)-3-methylbutylsulfonyloxy)-N,N,N-trimethylethanammonium chloride (21-19) | 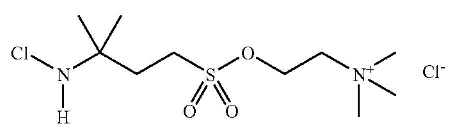 |
| 2-(3-(dichloroamino)-3-methylbutylsulfonyloxy)-N,N,N-trimethylethanammonium chloride (21-20) | 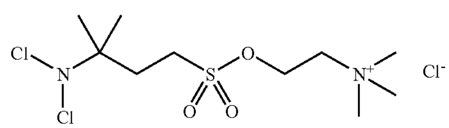 |
| 2-((3-(chloroamino)-3-methylbutyl)(hydroxy)phosphoryloxy)-N,N,N-trimethylethan-ammonium chloride (21-21) | 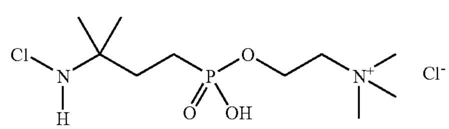 |
| 2-((3-(dichloroamino)-3-methylbutyl)(hydroxy)phosphoryloxy)-N,N,N-trimethylethan-ammonium chloride (21-22) | 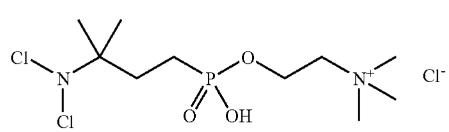 |
| 2-((3-(chloroamino)-3-methylbutyl)(methoxy)phosphoryloxy)-N,N,N-trimethylethan-ammonium chloride (21-23) | 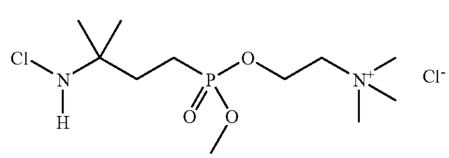 |
| 2-((3-(dichloroamino)-3-methylbutyl)(methoxy)phosphoryloxy)-N,N,N-trimethylethan-ammonium chloride (21-24) | 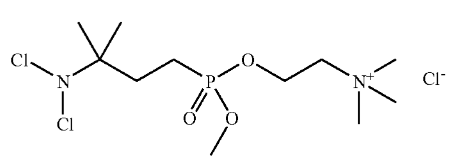 |

TABLE 1-continued

| Name (Compound No.) | Structure |
|---|---|
| 2-(((3-(chloroamino)-3-methylbutyl(hydroxy)phosphoryl)(methyl)amino)-N,N,N-trimethylethanammonium chloride (21-25) | 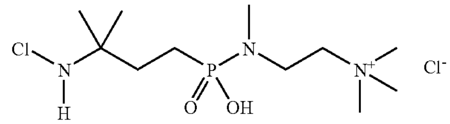 |
| 2-(((3-(dichloroamino)-3-methylbutyl)(hydroxy)phosphoryl)(methyl)amino)-N,N,N-trimethylethanammonium chloride (21-26) | 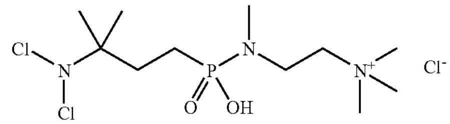 |
| 2-(((3-(chloroamino)-3-methylbutyl)(methoxy)phosphoryl)(methyl)amino)-N,N,N-trimethylethanammonium chloride (21-27) | 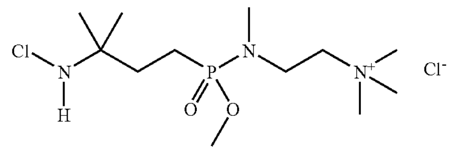 |
| 2-(((3-(dichloroamino)-3-methylbutyl)(methoxy)phosphoryl)(methyl)amino)-N,N,N-trimethylethanammonium chloride (21-28) | 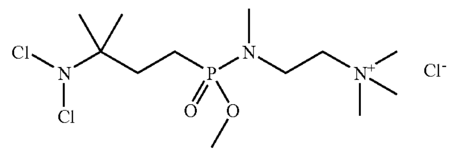 |
| 2-(chloroamino)-N,N,N-2-tetramethylpropan-1-ammonium chloride (21-29) | 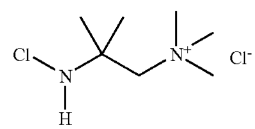 |
| 2-(dichloroamino)-N,N,N,2-tetramethylpropan-1-ammonium chloride (21-30) | 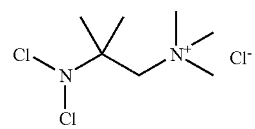 |
| 3-(chloroamino)-N,N,N,3-tetramethylbutan-1-ammonium chloride (21-31) | 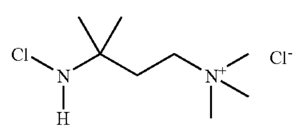 |
| 3-(dichloroamino)-N,N,N,3-tetramethylbutan-1-ammonium chloride (21-32) | 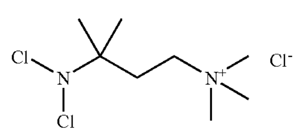 |
| 2-(chloroamino)-N-(fluoromethyl)-N,N,2-trimethylpropan-1-ammonium chloride (21-33) | 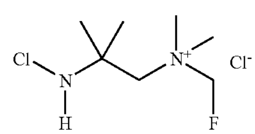 |
| 2-(dichloroamino)-N-(fluoromethyl)-N,N,2-trimethylpropan-1-ammonium chloride (21-34) | 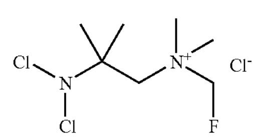 |
| 3-(chloroamino)-N-(fluoromethyl)-N,N,3-trimethylbutan-1-ammonium chloride (21-35) | 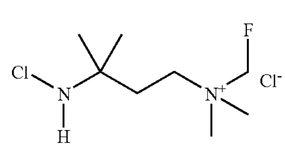 |

TABLE 1-continued

| Name (Compound No.) | Structure |
|---|---|
| 3-(dichloroamino)-N-(fluoromethyl)-N,N,3-trimethylbutan-1-ammonium chloride (21-36) | 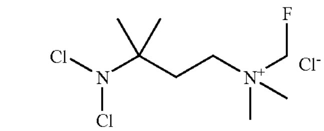 |
| 2-(chloroamino)-N,N,2-trimethyl-N-(2,2,2-trifluoroethyl)propan-1-ammonium chloride (21-37) | 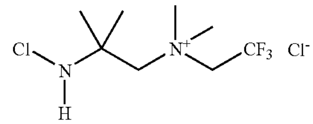 |
| 2-(dichloroamino)-N,N,2-trimethyl-N-(2,2,2-trifluoroethyl)propan-1-ammonium chloride (21-38) | 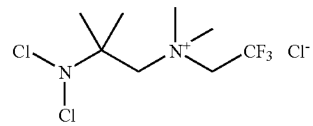 |
| 3-(chloroamino)-N,N,3-trimethyl-N-(2,2,2-trifluoroethyl)butan-1-ammonium chloride (21-39) | 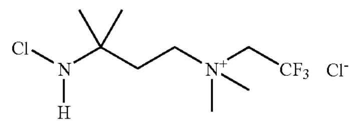 |
| 3-(dichloroamino)-N,N,3-trimethyl-N-(2,2,2-trifluoroethyl)butan-1-ammonium chloride (21-40) | 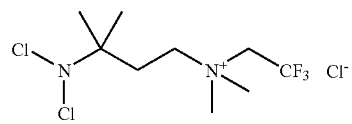 |
| N-(2-(chloroamino)-2-methylpropyl)-3,3,3-trifluoro-N,N-dimethylpropan-1-ammonium chloride (21-41) | 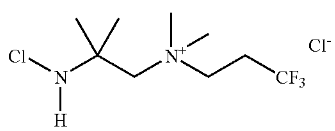 |
| N-(2-(dichloroamino)-2-methylpropyl)-3,3,3-trifluoro-N,N-dimethylpropan-1-ammonium chloride (21-42) | 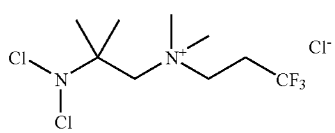 |
| 3-(chloroamino)-N,N,3-trimethyl-N-(3,3,3-trifluoropropyl)butan-1-aminium chloride (21-43) | 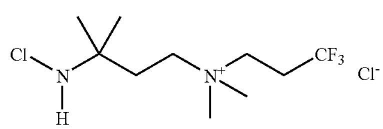 |
| 3-(dichloroamino)-N,N,3-trimethyl-N-(3,3,3-trifluoropropyl)butan-1-aminium chloride (21-44) | 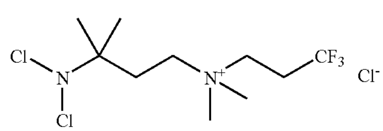 |
| N-butyl-N-(2-(chloroamino)-2-methylpropyl)-N-methylbutan-1-ammonium chloride (21-45) | 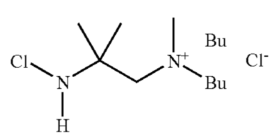 |
| N-butyl-N-(2-(dichloroamino)-2-methylpropyl)-N-methylbutan-1-ammonium chloride (21-46) | 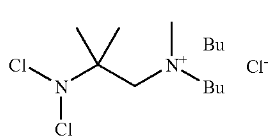 |
| N,N-dibutyl-3-(chloroamino)-N,3-dimethylbutan-1-ammonium chloride (21-47) | 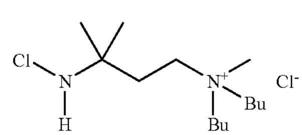 |

TABLE 1-continued

| Name (Compound No.) | Structure |
|---|---|
| N,N-dibutyl-3-(dichloroamino)-N,3-dimethylbutan-1-ammonium chloride (21-48) | 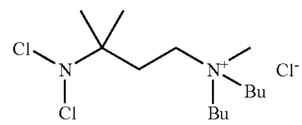 |
| N,N-dibutyl-N-(2-(chloroamino)-2-methylpropyl)butan-1-ammonium chloride (21-49) | 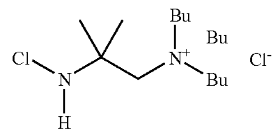 |
| N,N-dibutyl-N-(2-(dichloroamino)-2-methylpropyl)butan-1-ammonium chloride (21-50) | 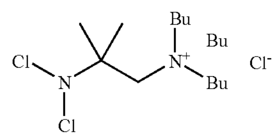 |
| N,N,N-tributyl-3-(chloroamino)-3-methylbutan-1-ammonium chloride (21-51) | 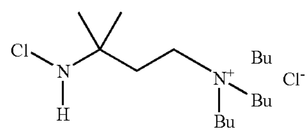 |
| N,N,N-tributyl-3-(dichloroamino)-3-methylbutan-1-ammonium chloride (21-52) | 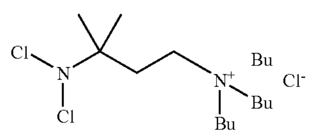 |
| N-(2-(chloroamino)-2-methylpropyl)-3-fluoro-N,N-dimethylbenzenaminium chloride (21-53) | 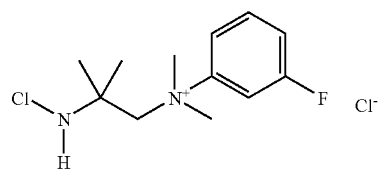 |
| N-(2-(dichloroamino)-2-methylpropyl)-3-fluoro-N,N-dimethylbenzenaminium chloride (21-54) | 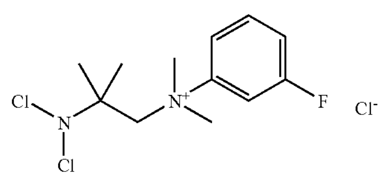 |
| N-(3-(chloroamino)-3-methylbutyl)-3-fluoro-N,N-dimethylbenzaminium chloride (21-55) | 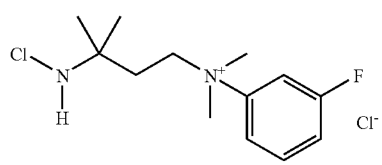 |
| N-(3-(dichloroamino)-3-methylbutyl)-3-fluoro-N,N-dimethylbenzenaminium chloride (21-56) | 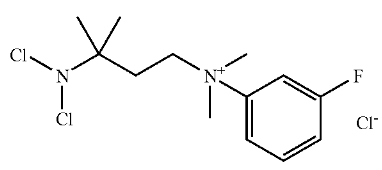 |
| 5-(chloroamino)-3-fluoro-N,N,N,5-tetramethylhexan-1-ammonium chloride (21-57) | 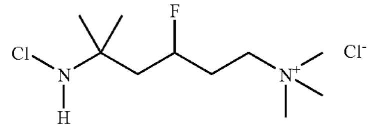 |

TABLE 1-continued

| Name (Compound No.) | Structure |
|---|---|
| 5-(dichloroamino)-3-fluoro-N,N,N,5-tetramethylhexan-1-ammonium chloride (21-58) | 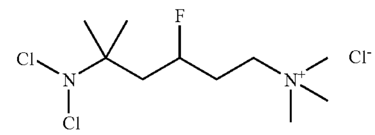 |
| 5-(chloroamino)-3,3-difluoro-N,N,N,5-tetramethylhexan-1-ammonium chloride (21-59) | 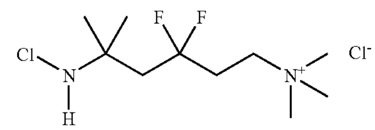 |
| 5-(dichloroamino)-3,3-difluoro-N,N,N,5-tetramethylhexan-1-ammonium chloride (21-60) | 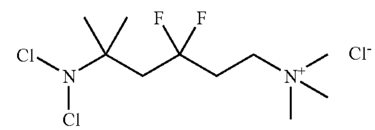 |
| 6-(chloroamino)-3-fluoro-N,N,N,6-tetramethylheptan-1-ammonium chloride (21-61) | 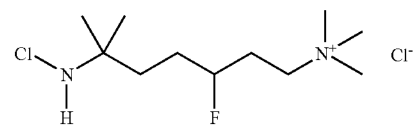 |
| 6-(dichloroamino)-3-fluoro-N,N,N,6-tetramethylheptan-1-ammonium chloride (21-62) | 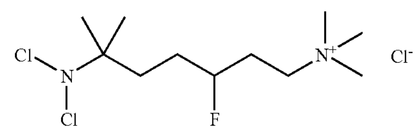 |
| 6-(chloroamino)-3,3-difluoro-N,N,N,6-tetramethylheptan-1-ammonium chloride (21-63) | 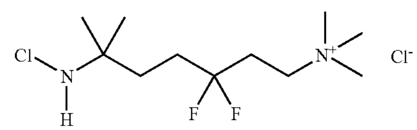 |
| 6-(dichloroamino)-3,3-difluoro-N,N,N,6-tetramethylheptan-1-ammonium chloride (21-64) | 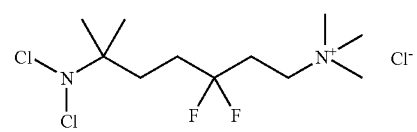 |
| N-(2-(chloroamino)-2-methylpropyl)-N,N-dimethyl-3-(trifluoromethyl)benzenammonium chloride (21-65) | 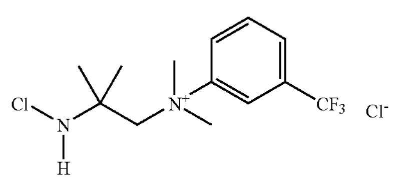 |
| N-(2-(dichloroamino)-2-methylpropyl)-N,N-dimethyl-3-(trifluoromethyl)benzenammonium chloride (21-66) | 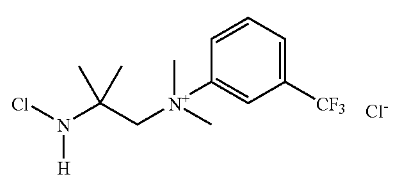 |
| N-(3-(chloroamino)-3-methylbutyl)-N,N-dimethyl-3-(trifluoromethyl)benzenammonium chloride (21-67) | 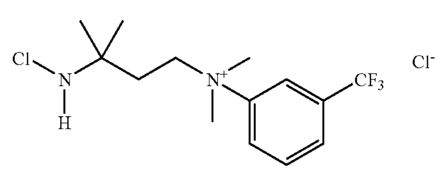 |

TABLE 1-continued

| Name (Compound No.) | Structure |
|---|---|
| N-(3-(dichloroamino)-3-methylbutyl)-N,N-dimethyl-3-(trifluoromethyl)benzenammonium chloride (21-68) | 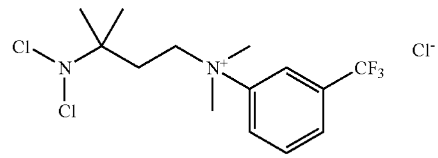 |
| N-(2-(chloroamino)-2-methylpropyl)-N,N-dimethyl-5-(trifluoromethyl)pyridin-2-ammonium chloride (21-69) | 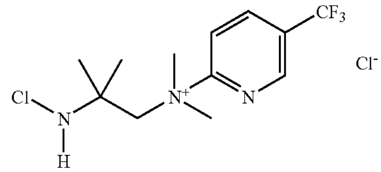 |
| N-(2-(dichloroamino)-2-methylpropyl)-N,N-dimethyl-5-(trifluoromethyl)pyridin-2-ammonium chloride (21-70) | 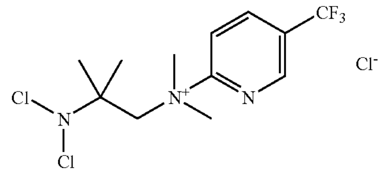 |
| N-(3-(chloroamino)-3-methylbutyl)-N,N-dimethyl-5-(trifluoromethyl)pyridin-2-ammonium chloride (21-71) | 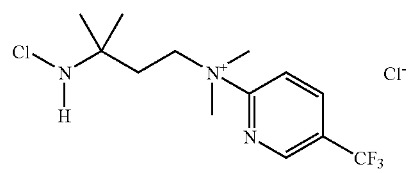 |
| N-(3-(dichloroamino)-3-methylbutyl)-N,N-dimethyl-5-(trifluoromethyl)pyridin-2-ammonium chloride (21-72) | 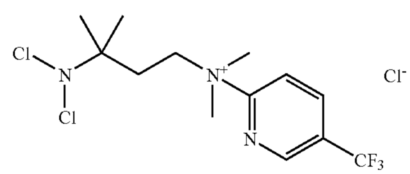 |
| 4-(2-(chloroamino)-2-methylpropyl)-4-methylmorpholin-4-ium chloride (21-73) | 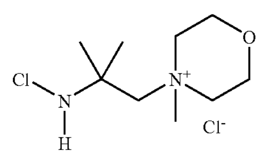 |
| 4-(2-(dichloroamino)-2-methylpropyl)-4-methylmorpholin-4-ium chloride (21-74) | 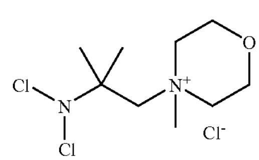 |
| 4-(3-(chloroamino)-3-methylbutyl)-4-methylmorpholin-4-ium chloride (21-75) | 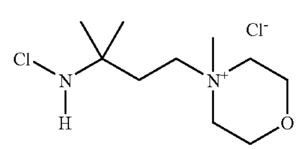 |
| 4-(3-(dichloroamino)-3-methylbutyl)-4-methylmorpholin-4-ium chloride (21-76) | 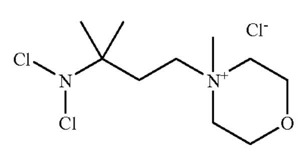 |

TABLE 1-continued

| Name (Compound No.) | Structure |
|---|---|
| 1-(2-(chloroamino)-2-methylpropyl)-1-methylpiperidium chloride (21-77) | 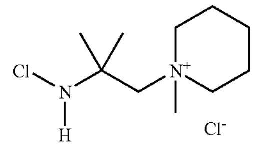 |
| 1-(2-(dichloroamino)-2-methylpropyl)-1-methylpiperidium chloride (21-78) | 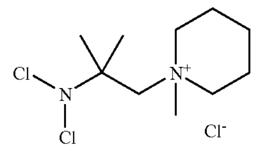 |
| 1-(3-(chloroamino)-3-methylbutyl)-1-methylpiperidium chloride (21-79) | 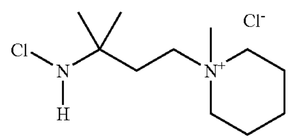 |
| 1-(3-(dichloroamino)-3-methylbutyl)-1-methylpiperidium chloride (21-80) | 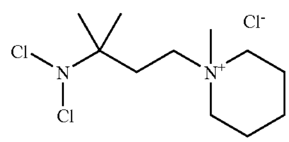 |
| (2-(chloroamino)-2-methylpropyl) trimethylphosphonium chloride (21-81) | 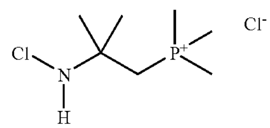 |
| (2-(dichloroamino)-2-methylpropyl) trimethylphosphonium chloride (21-82) | 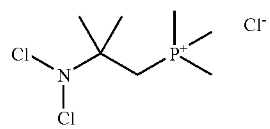 |
| (3-(chloroamino)-3-methylbutyl) trimethylphosphonium chloride (21-83) | 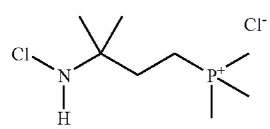 |
| (3-(dichloroamino)-3-methylbutyl) trimethylphosphonium chloride (21-84) | 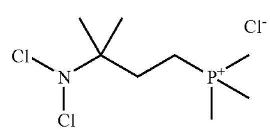 |
| (2-(chloroamino)-2-methylpropyl) dimethylsulfonium chloride (21-85) | 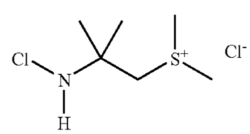 |
| (2-(dichloroamino)-2-methylpropyl) dimethylsulfonium chloride (21-86) | 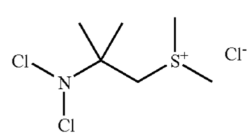 |
| (3-(chloroamino)-3-methylbutyl)dimethylsulfonium chloride (21-87) | 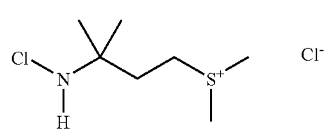 |

TABLE 1-continued

| Name (Compound No.) | Structure |
|---|---|
| (3-(dichloroamino)-3-methylbutyl)dimethylsulfonium chloride (21-88) | 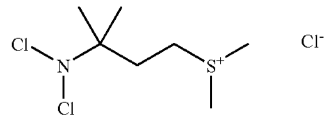 |
| 2-((2-(chloroamino)-2-methylpropyl)dimethylammonio)ethanesulfonate (21-89) | 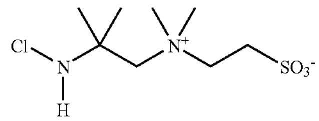 |
| 2-((2-(dichloroamino)-2-methylpropyl)dimethylammonio)ethanesulfonate (21-90) | 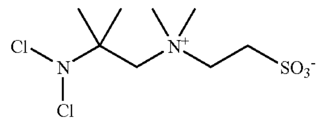 |
| 2-(4-(2-(chloroamino)propan-2-yl)-1H-1,2,3-triazol-1-yl)-N,N,N-trimethylethanaminium chloride (21-91) | 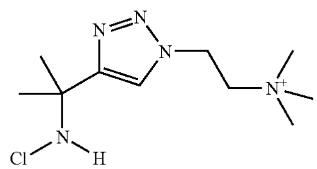 |
| 2-(4-(2-(dichloroamino)propan-2-yl)-1H-1,2,3-triazol-1-yl)-N,N,N-trimethylethanaminium chloride (21-92) | 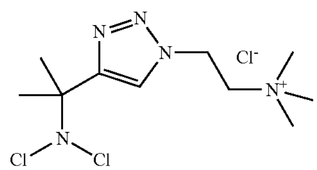 |
| 1-(2-(3-(dichloroamino)-3-methylbutanoyloxy)ethyl)-1-methylpiperidinium chloride (21-93) | 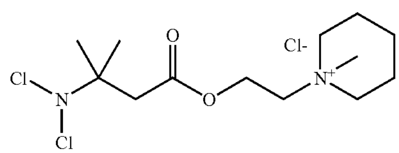 |
| 1-(2-(3-(chloroamino)-3-methylbutanoyloxy)ethyl)-1-methylpiperidinium chloride (21-94) | 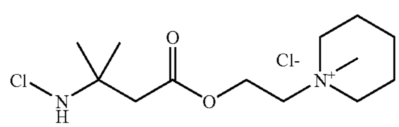 |
| 5-(dichloroamino)-3-hydroxy-N,N,N,5-tetramethylhexan-1-aminium chloride (21-95) | 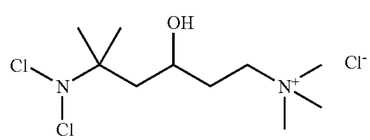 |
| 5-(chloroamino)-3-hydroxy-N,N,N,5-tetramethylhexan-1-aminium chloride (21-96) | 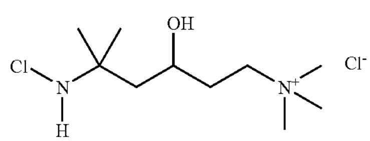 |
| 6-(dichloroamino)-4-hydroxy-N,N,N,6-tetramethylheptan-1-aminium chloride (21-97) | 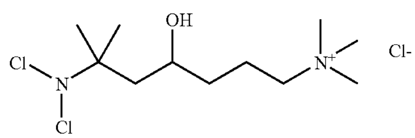 |
| 6-(dichloroamino)-4-hydroxy-N,N,N,6-tetramethylheptan-1-aminium chloride (21-98) | 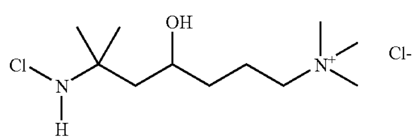 |

TABLE 1-continued

| Name (Compound No.) | Structure |
|---|---|
| 6-(dichloroamino)-4-fluoro-N,N,N,6-tetramethylheptan-1-aminium chloride (21-99) | 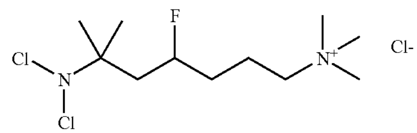 |
| 6-(chloroamino)-4-fluoro-N,N,N,6-tetramethylheptan-1-aminium chloride (21-100) | 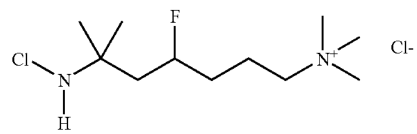 |
| 1-(3-(dichloroamino)-3-methylbutyl)pyridinium chloride (21-101) | 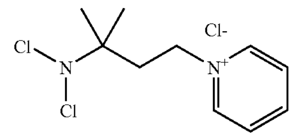 |
| 1-(3-(chloroamino)-3-methylbutyl)pyridinium chloride (21-102) | 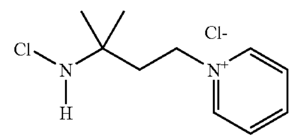 |
| 1-(4-(dichloroamino)-4-methylpentyl)pyridinium chloride (21-103) | 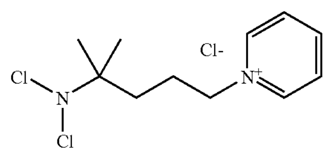 |
| 1-(4-(chloroamino)-4-methylpentyl)pyridinium chloride (21-104) | 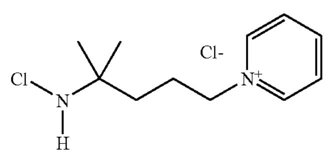 |
| (4-(chloroamino)-4-methylpentyl)trimethylphosphonium chloride (21-105) | 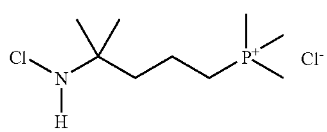 |
| (4-(dichloroamino)-4-methylpentyl)trimethylphosphonium chloride (21-106) | 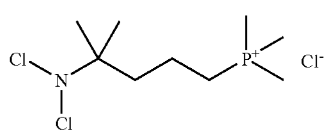 |
| 4-(chloroamino)-N,N,N-tetramethylpentan-1-ammonium chloride (21-107) | 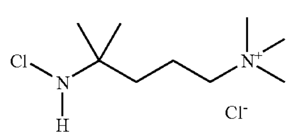 |
| 4-(dichloroamino)-N,N,N,4-tetramethylpentan-1-ammonium chloride (21-108) | 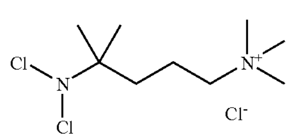 |
| 4-acetyl-1-(2-(chloroamino)-2-methylpropyl)-1-methylpiperazin-1-ium chloride (21-109) | 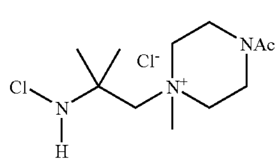 |

TABLE 1-continued

| Name (Compound No.) | Structure |
| --- | --- |
| 4-acetyl-1-(2-(dichloroamino)-2-methylpropyl)-1-methylpiperazin-1-ium chloride (21-110) | 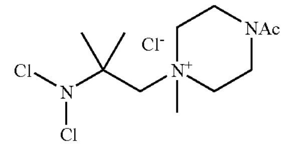 |
| 3-(3-(chloroamino)-3-methylbutylsulfonyl)-N,N,N-trimethylpropan-1-ammonium chloride (21-111) | 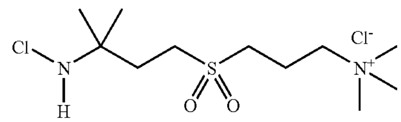 |
| 3-(3-(dichloroamino)-3-methylbutylsulfonyl)-N,N,N-trimethylpropan-1-ammonium chloride (21-112) | 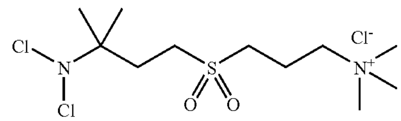 |
| 3-(chloroamino)-N,N-diethyl-N,3-dimethylbutan-1-ammonium chloride (21-113) | 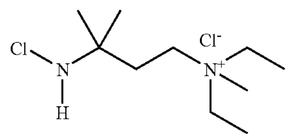 |
| 3-(dichloroamino)-N,N-diethyl-N,3-dimethylbutan-1-ammonium chloride (21-114) | 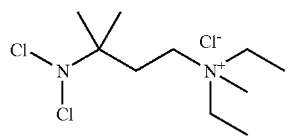 |
| 1-(3-(chloroamino)-3-methylbutyl)-4,4-difluoro-1-methylpiperidinium chloride (21-115) | 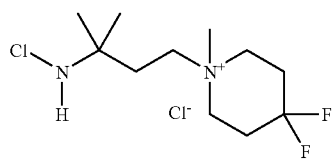 |
| 1-(3-(Dichloroamino)-3-methylbutyl)-4,4-difluoro-1-methylpiperidinium chloride (21-116) | 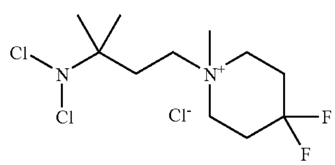 |
| 1-(3-(chloroamino)-3-methylbutyl)-1-methylazepanium chloride (21-117) | 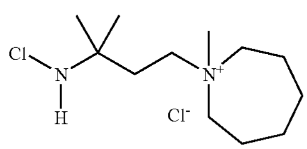 |
| 1-(3-(dichloroamino)-3-methylbutyl)-1-methylazepanium chloride (21-118) | 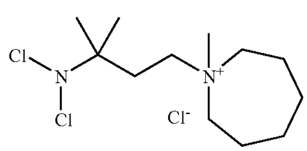 |
| 1-(3-(chloroamino)-3-methylbutyl)-1-azoniabicyclo[2.2.2]octane methanesulfonate (21-119) | 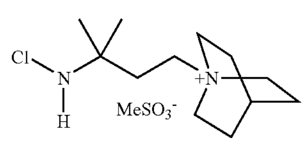 |

TABLE 1-continued

| Name (Compound No.) | Structure |
|---|---|
| 1-(3-(dichloroamino)-3-methylbutyl)-1-azoniabicyclo[2.2.2]octane methanesulfonate (21-120) | 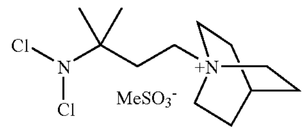 |
| 1-(3-(chloroamino)-3-methylbutyl)-1,4,4-trimethylpiperidinium chloride (21-121) | 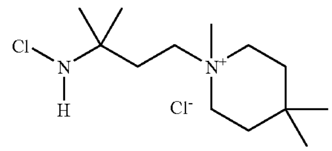 |
| 1-(3-(dichloroamino)-3-methylbutyl)-1,4,4-trimethylpiperidinium chloride (21-122) | 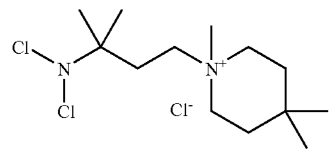 |
| N-butyl-3-(chloroamino)-N,N,3-trimethylbutan-1-ammonium chloride (21-123) | 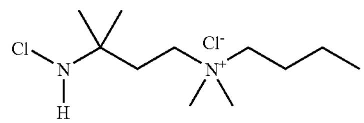 |
| N-butyl-3-(dichloroamino)-N,N,3-trimethylbutan-1-ammonium chloride (21-124) | 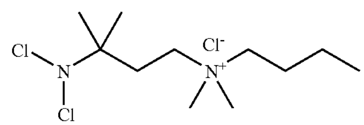 |
| N-(3-(chloroamino)-3-methylbutyl)-N,N-dimethylcyclohexanammonium chloride (21-125) | 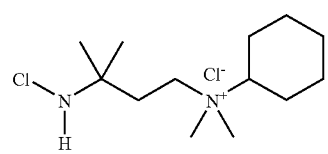 |
| N-(3-(dichloroamino)-3-methylbutyl)-N,N-dimethylcyclohexanammonium chloride (21-126) | 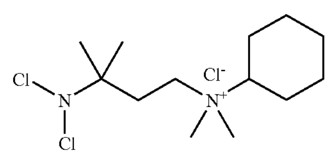 |
| $N^1$-(3-(chloroamino)-3-methylbutyl)-$N^1$, $N^1$, $N^3$, $N^3$, $N^3$-pentamethylpropane-1,3-diammonium chloride (21-127) | 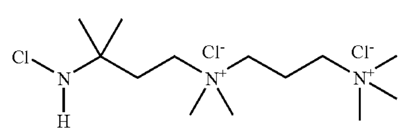 |
| $N^1$-(3-(dichloroamino)-3-methylbutyl)-$N^1$, $N^1$, $N^3$, $N^3$, $N^3$-pentamethylpropane-1,3-diammonium chloride (21-128) | 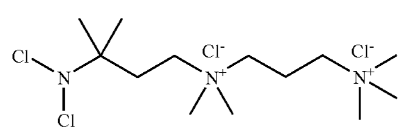 |
| 1-(3-(chloroamino)-3-methylbutyl)-1-methylpyrrolidinium chloride (21-129) | 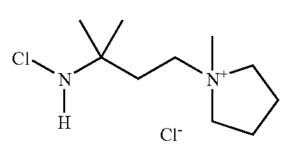 |
| 1-(3-(dichloroamino)-3-methylbutyl)-1-methylpyrrolidinium chloride (21-130 | 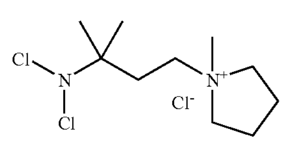 |

TABLE 1-continued

| Name (Compound No.) | Structure |
| --- | --- |
| 3-(chloroamino)-N,N,3-trimethyl-N-(2,2,2-trifluoroethyl)butan-1-ammonium chloride (21-131) | 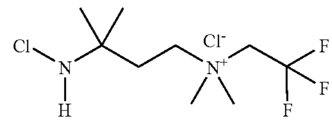 |
| 3-(dichloroamino)-N,N,3-trimethyl-N-(2,2,2-trifluoroethyl)butan-1-ammonium chloride (21-132) | 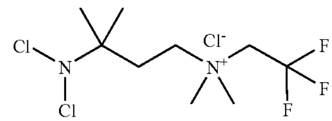 |
| 3-(chloroamino)-N-ethyl-N,N,3-trimethylbutan-1-aminium chloride (21-133) | 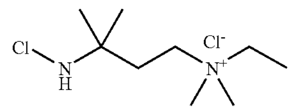 |
| 3-(dichloroamino)-N-ethyl-N,N,3-trimethylbutan-1-aminium chloride (21-134) | 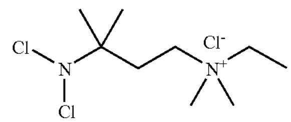 |
| N-(3-(chloroamino)-3-methylbutyl)-N,N-dimethylhexan-1-aminium chloride (21-135) | 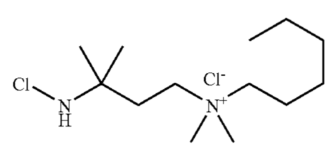 |
| N-(3-(dichloroamino)-3-methylbutyl)-N,N-dimethylhexan-1-aminium chloride (21-136) | 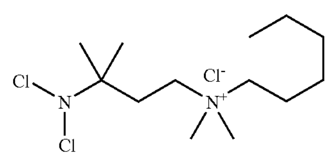 |
| N-(3-(chloroamino)-3-methylbutyl)-N,N-dimethyldodecan-1-aminium chloride (21-137) | 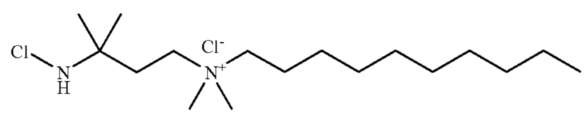 |
| N-(3-(dichloroamino)-3-methylbutyl)-N,N-dimethyldodecan-1-aminium chloride (21-138) | 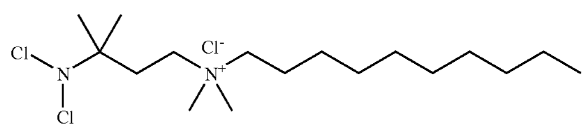 |
| 1-(3-(chloroamino)-3-methylbutyl)pyridinium chloride (21-139) | 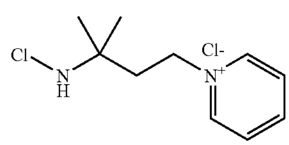 |
| 1-(3-(dichloroamino)-3-methylbutyl)pyridinium chloride (21-140) | 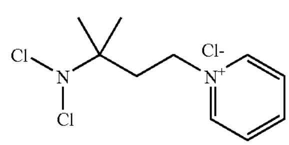 |
| 4-(chloroamino)-N,N,N-trimethyl-4-propylheptan-1-aminium (21-141) | 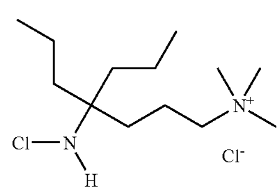 |

TABLE 1-continued

| Name (Compound No.) | Structure |
|---|---|
| 4-(dichloroamino)-N,N,N-trimethyl-4-propylheptan-1-aminium (21-142) | 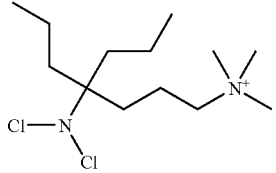 |
| 3-(1-chloroamino)cyclohexyl)-N,N,N-trimethylpropan-1-aminium (21-143) | 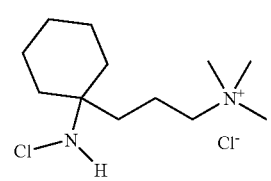 |
| 3-(1-(dichloroamino)cyclohexyl)-N,N,N-trimethylpropan-1-aminium (21-144) | 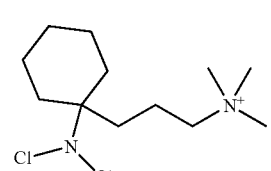 |
| 3-(1-(chloroamino)cyclopentyl)-N,N,N-trimethylpropan-1-aminium (21-145) | 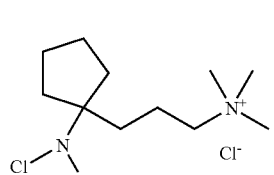 |
| 3-(1-(dichloroamino)cyclopentyl)-N,N,N-trimethylpropan-1-aminium (21-146) | 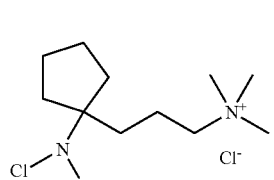 |

The starting materials and reagents employed in preparing these compounds are either available from commercial suppliers such as Sigma-Aldrich Chemical Company (Millwaukee, Wis., USA), TCI America (Portland, Oreg., USA), Matrix Scientific (Columbia, S.C., USA), VWR International (Pasadena, Calif., USA), Fisher Scientific (Chicago, Ill., USA), Alfa Aesar (Wood Hill, Mass., USA), Advanced Chem Tech (Louisville, Ky., USA), Chem Impex (Chicago, Ill., USA), and Advanced Asymmetrics (Belleville, Ill., USA) or are prepared by methods known in the art following procedures available in the literature and references such as *Protective Groups in Organic Synthesis* (John Wiley & Sons, 3$^{rd}$ Edition), *Protective Groups, Foundation of Organic Chemistry* (Thieme & Sons Inc.), *Fieser and Fieser's Reagents for Organic Synthesis*, Volumes 1-15 (John Wiley and Sons, 1991), *Rodd's Chemistry of Carbon Compounds*, Volumes 1-15 and Supplemental Materials (Elsevier Science Publishers, 1989), *Organic Reactions, Volume* 1-40 (John Wiley & Sons, 1991), *March's Advanced Organic Chemistry* (John Wiley & Sons, 4$^{th}$ Edition), and *Larock's Comprehensive Organic Transformation* (VCH Publishers Inc., 1989).

Various chlorine sources may be used to produce the N-chlorinated compounds, e.g., chlorine itself (i.e., Cl$_2$ gas), certain N-chloroarylsulfonamide salts, wherein the aryl group contains from about 6 to about 15 carbon atoms with 1 or 2 aromatic rings, 6 to 10 or 6 to 8 carbon atoms and one aromatic ring, such as N-chlorobenzene-sulfonamide or N-chloro-4-alkylbenzenesulfonamide, wherein the alkyl group is an alkyl from about 1 to about 4 carbons, such as methyl or ethyl. The N-chlorobenzene-sulfonamides or N-chloro-4-alkylbenzenesulfonamides are often used in the form of their salts, e.g., alkali salts, e.g., sodium or potassium salts. Frequently used reagents include N-chlorobenzene-sulfonamide and N-chloro-4-methyl-benzenesulfonamide in the form of their sodium salts, because they are readily commercially available. Other non-limiting chlorinating agents include HOCl and N-chlorosuccinimide. Similarly, the halogenation reaction may be accomplished using the corresponding reagents as disclosed herein that provide a source of bromine, as in known in the art. Examples of such bromination reagents include Br$_2$, N-bromoarylsulfonamide salts, HOBr and N-bromosuccinimide, and the like.

Compounds of Formula I (which includes compounds of Formulae IA, IB and IC) may be prepared according to the following exemplary generalized schemes in addition to other standard manipulations known in the art. These schemes are illustrative and are not limiting. Compound numbers shown in the schemes do not necessarily correlate to compound numbers used in Table 1 or the Examples.

Scheme 1: Ester-Containing Compounds

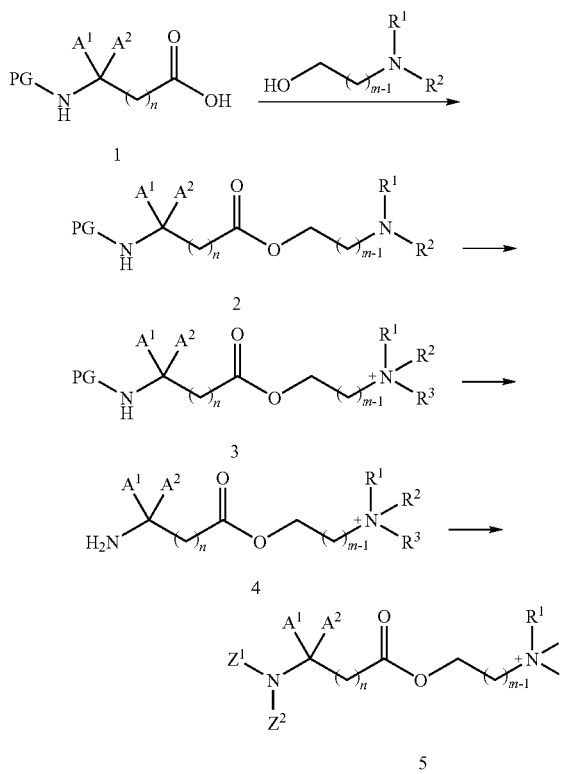

Step 1-1: Esterification of acid 1 can be accomplished by condensation with an optionally substituted aminoalcohol under conditions well known in the art, preferably in an inert organic solvent, in presence of a coupling agent and an organic base to provide compound 2. A wide range of amines can be employed, e.g. primary N-alkyl amines, substituted N-alkyl amines, secondary amines, etc. This reaction can be performed using commonly employed amide coupling agents such as O-(7-azabenzotriazol-1-yl)-N, N,N',N'-tetramethyluronium hexafluorophosphate (HATU), 1-hydroxybenzotriazole hydrate (HOBT), carbodiimides such as N,N'-carbonyldiimidazole (CDI), diphenylphosphoryl azide (DPPA), and the like. Suitable organic bases include diisopropyethylamine (DIEA), triethylamine (TEA), pyridine, N-methyl morpholine, and the like. Suitable inert organic solvents which can be used include, e.g., N,N-dimethylformamide, acetonitrile, dichloromethane, and the like. This reaction is typically carried out at temperatures in the range of about 0° C. to about 80° C. The reaction is continued until completion, which typically occurs in about 2 to 24 hours.

Step 1-2: Quarternization of the tertiary amine of compound 2 can be carried out using an alkylating agent, either in the presence or absence of a base, to provide compound 3 using methods known in the art. Suitable alkylating agents include alkyl halides such as methyl iodide, and the like. The alkylation may be conducted neat with excess of alkylating reagent or in an inert organic solvent such as, e.g., N,N-dimethylformamide, acetonitrile, dichloromethane, alcohols and N-methylpyridone. Suitable bases include N,N-diisopropyl ethylamine, triethylamine, cesium carbonate and the like. The reaction is typically conducted at room temperature to 100° C. for about 16 to about 48 hours.

Step 1-3: Compound 3 can then be converted to compound 4 by removal of the protecting group, e.g. by hydrogenation to remove an N-benzyloxycarbonyl protecting group (Cbz), or by treatment with an acid for removal of a tert-butyloxycarbony (Boc) protecting group. Deprotection is typically carried out in a polar organic solvent such as ethanol or methanol. Hydrogenations are typically carried out in the presence of a catalytic amount of palladium(II) or palladium(0), such as palladium(0) on carbon, under a hydrogen atmosphere. The hydrogenation may be carried at ambient temperature in about 1 to 24 hours.

Step 1-4: Chlorination of compound 4 to the corresponding N,N-dichloroamine or N-chloroamine (i.e., where at least one of $Z^1$ and $Z^2$ are Cl) can be accomplished by treatment of the primary amine with a suitable amount (as described in the Examples below) of chlorinating agent such as tert-butyl hypochlorite, trichloroisocyanuric acid, sodium hypochlorite, N-chlorosuccinimide, various N-chlorohydantoins or chlorine gas in a solvent such as water, N,N-dimethylformamide, methylene chloride, and the like, to give chlorinated or dichlorinated compounds of Formula I. The reaction is typically carried out at low temperature to room temperature for about 2 to 24 hours. The corresponding N-bromo- and N,N-dibrominated compounds (i.e., where at least one of $Z^1$ and $Z^2$ are Br) may be prepared in similar fashion with a suitable source of bromine, as described above.

Scheme 2: Alternative Synthesis of Ester-Containing Compounds

Alternatively, ester-containing compounds of Formula I can be prepared by the reaction steps as shown in Scheme 2.

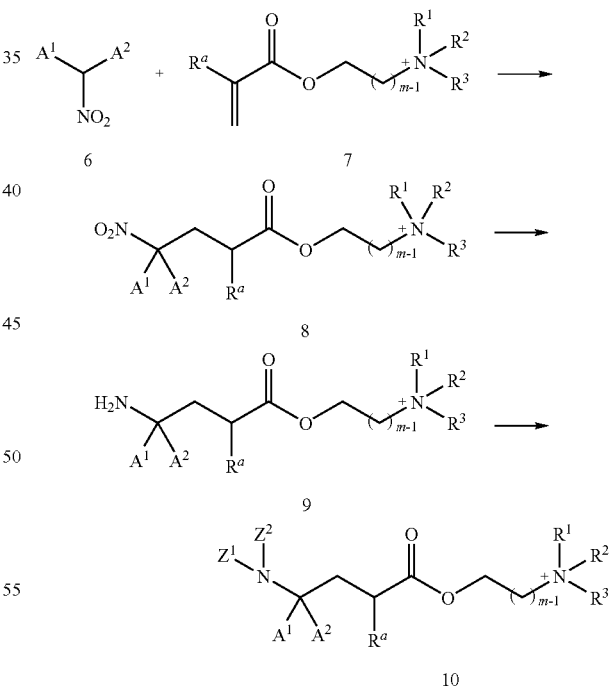

Step 2-1: Compound 6 can be coupled with an α,β-unsaturated ester 7 under suitable reaction conditions, e.g., in an inert organic solvent and in the presence of an organic base, to provide ester 8. Suitable organic bases include benzyltrimethylammonium hydroxide, DIEA, TEA, pyridine, N-methyl morpholine, and the like. Suitable inert organic solvents which can be used include, e.g., water, dioxane, N,N-dimethylformamide, acetonitrile, dichloromethane, and the like. This reaction is typically conducted at temperatures in the range of about 0° C. to 100° C. The reaction is continued until completion, which typically occurs in about 2 to 24 hours.

Step 2-2: Compound 8 can then be converted to amine 9 under prolonged hydrogenation conditions as described in step 1-3.

Step 2-3: Compound 9 can then be converted to the corresponding N,N-dihalo- or N-haloamine 10 as described in step 1-4.

Scheme 3: Amide-Containing Compounds

Amide-containing compounds of Formula I can be prepared by the reaction steps as shown in Scheme 3.

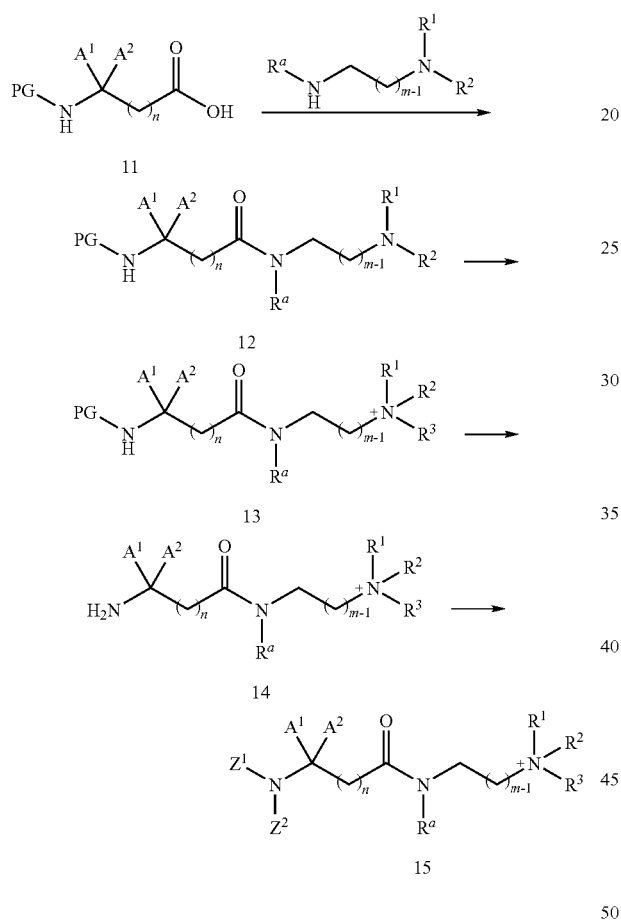

Step 3-1: Amidation of aminoacid 11 can be carried out by reacting an optionally substituted diamine (wherein $R^a$ is H, alkyl, aryl, cycloalkyl, heteroalkyl, heteroaryl or heterocycloalkyl, each of which may be optionally substituted) under suitable reaction conditions, preferably in an inert organic solvent, in presence of an amide coupling agent and an organic base to provide an amide compound 12. Amidation reaction conditions are well known in the art. A wide range of amines can be employed, e.g. primary amines, substituted primary amines, secondary amines, etc. This reaction can be performed with any number of known coupling agents, such as O-(7-azabenzotriazol-1-yl)-N,N,N',N'-tetramethyluronium hexafluorophosphate (HATU), 1-hydroxybenzotriazole hydrate (HOBT), carbodiimides such as N,N'-carbonyldiimidazole (CDI), diphenylphosphoryl azide (DPPA), and the like. Suitable organic bases include diisopropyethylamine (DIEA), TEA, pyridine, N-methyl morpholine, and the like.

Suitable inert organic solvents which can be used include, e.g., N,N-dimethylformamide, acetonitrile, dichloromethane, and the like. This reaction is typically carried out at temperatures in the range of about 0° C. to about 80° C. The reaction is continued until completion, which typically occurs in about 2 to 24 hours.

Step 2: The tertiary amine 12 can be alkylated using an alkylating agent in the presence of a base, as described in step 1-2, to provide compound 13.

Step 3: N-Deprotection may be carried out as described in step 1-3 to give compound 14.

Step 4: Compound 14 can then be converted to the corresponding N,N-dihalo- or N-haloamine 15 as described in step 1-4.

Scheme 4: Sulfone-Containing Compounds

Sulfone-containing compounds of Formula I can be prepared by the reaction steps as shown in Scheme 4.

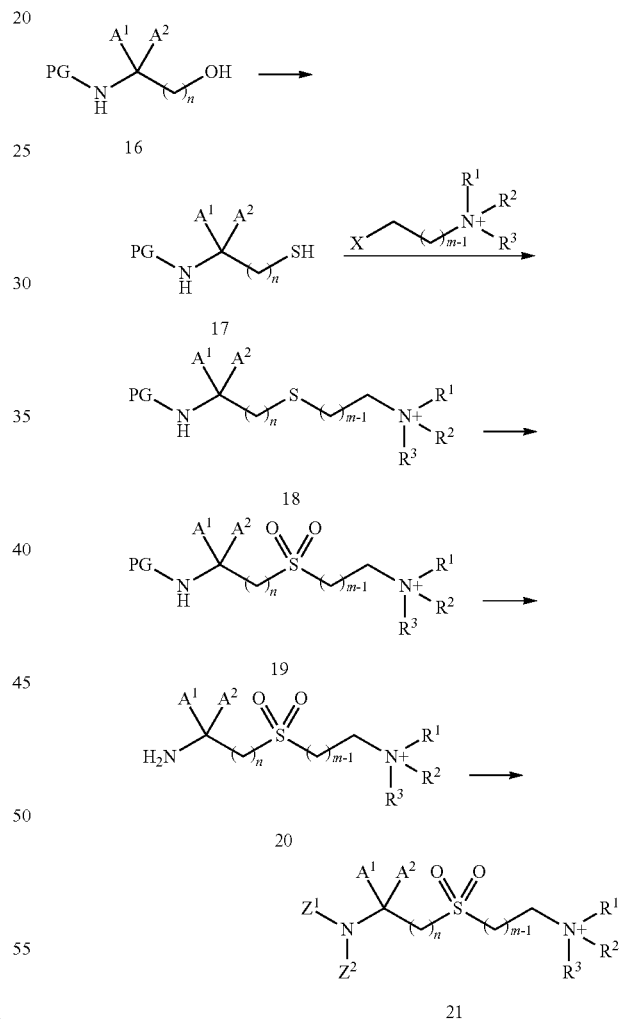

Step 4-1: N-Protected thiol 17 can be generated by reaction of compound 16 with thioacetic acid, phosphine and diisopropyl azodicarboxylate (DIAD) in a suitable solvent such as tetrahydrofuran, methylene chloride, and the like followed by deacylation with a suitable alkaline reagent such as LiOH in MeOH. The transformation is typically carried out at low temperatures, e.g., 0° C., and after the addition, the reaction is allowed to warm to ambient temperatures, e.g., about 25° C.

Step 4-2: Reaction of thiol 17 with trimethylammoniumalkyl halide in polar solvents such as DMF, THF, water, and the like in the presence of base affords compound 18. This reaction is generally performed at low temperatures, e.g., 0° C., and after the addition, the reaction is allowed to warm to about 100° C.

Step 4-3: Oxidation of compound 18 to sulfone 19 can be achieved using commercially available oxidizing agents, e.g., 3-chloroperoxybenzoic acid (MCPBA), oxone in solvents such as acetone, methylene chloride, methanol and the like. This reaction is typically done at low temperatures, e.g., 0° C., to ambient temperatures, e.g., about 25° C. for about 2 to 24 hours.

Step 4-4: N-Deprotection may be carried out as described in step 1-3.

Step 4-5: Compound 20 may then be converted to the corresponding N,N-dihalo- or N-haloamine 21 as described in step 1-4.

Scheme 5: Sulfonamide-Containing Compounds

Sulfonamide-containing compounds of Formula I can be prepared by the reaction steps as shown in Scheme 5.

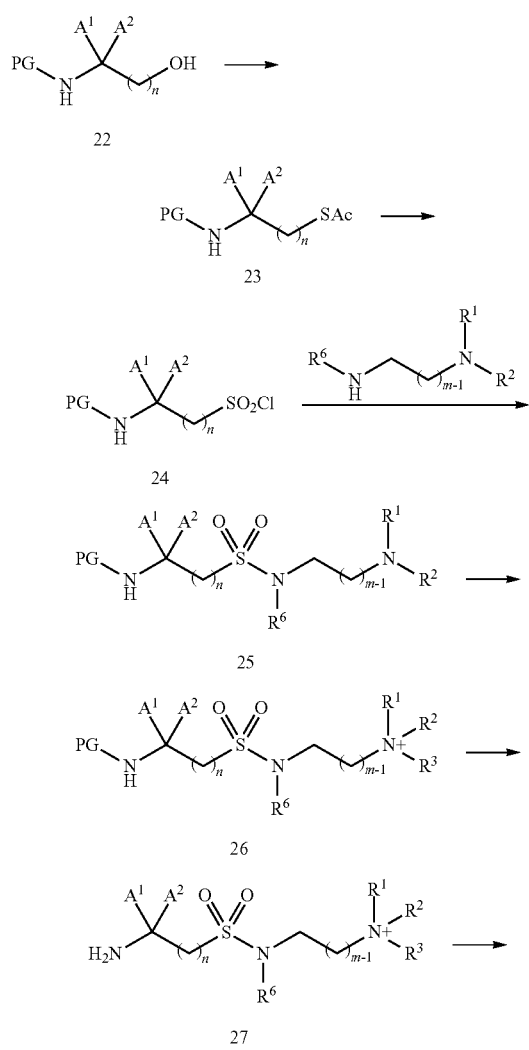

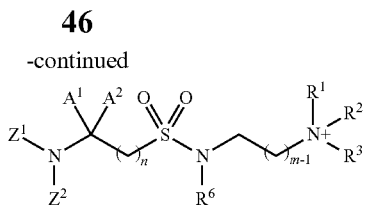

28

Step 5-1: N-Protected thioacetyl 23 can be generated by reaction of compound 22 with thioacetic acid, phosphine and diisopropyl azodicarboxylate (DIAD) in a suitable solvent such as tetrahydrofuran, methylene chloride, and the like. This reaction is typically carried out at temperature ranging from 0° C. to room temperature for about 8 to about 24 hours.

Step 5-2: Compound 23 can be oxidized to the corresponding sulfonyl chloride 24 with aqueous chlorine or aqueous hypochlorous acid, which can be generated by acidification of sodium hypochlorite in an organic solvent like methylene chloride. The reaction is typically carried out at 0° C. to room temperature for about 2 to about 24 hours.

Step 5-3: Sulfonyl chloride 24 can be reacted with an optionally substituted N,N-dialkylaminoalkane amine in a mixture of organic solvent and water in the presence of an inorganic base to provide sulfonamide 25. Suitable inorganic bases include sodium hydroxide, sodium bicarbonate, and the like. Suitable inert organic solvents include dichloromethane, THF, and the like. The reaction may be conducted at ambient temperature in about 2 to 24 hours.

Step 5-4: The tertiary amine 25 can be alkylated as described in step 1-3, to provide 26.

Step 5-5: N-Deprotection may be carried out as described in step 1-4.

Step 5-6: The amine compound 27 can then be converted to the corresponding corresponding N,N-dihalo- or N-haloamine 28 as described in step 1-4.

Scheme 6: Synthesis of Ammonium Compounds of Formula IA and IC

Ammonium compounds of Formula IA and IC can be prepared by the reaction steps as shown in Scheme 6.

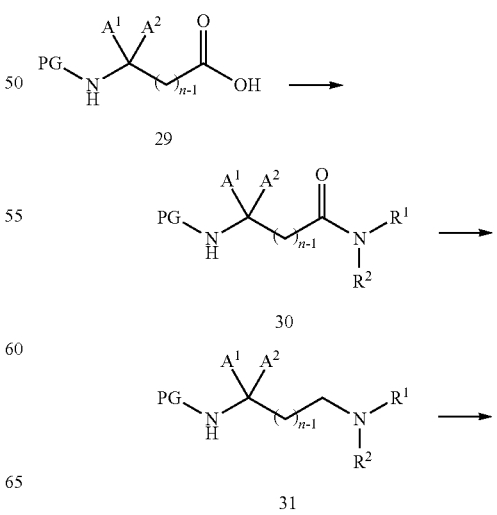

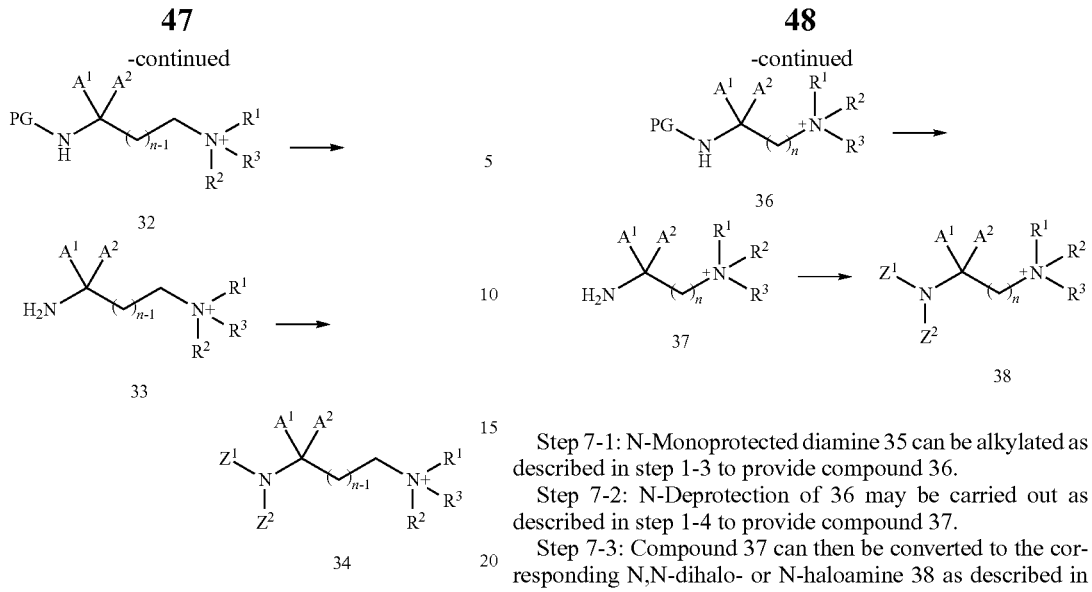

32

33

34

Step 6-1: Compound 29 can be condensed with an optionally substituted amine under suitable reaction conditions, preferably in an inert organic solvent, in presence of an amide coupling agent and an organic base to provide amide 30. A wide range of amines can be employed, e.g. primary amines, substituted primary amines, secondary amines, etc. This reaction can be performed using common amide coupling agents such as O-(7-azabenzotriazol-1-yl)-N,N,N', N'-tetramethyluronium hexafluorophosphate (HATU), 1-hydroxybenzotriazole hydrate (HOBT), carbodiimides such as N,N'-carbonyldiimidazole (CDI), diphenylphosphoryl azide (DPPA), and the like. Suitable organic bases include diisopropyethylamine (DIEA), TEA, pyridine, N-methyl morpholine, and the like. Suitable inert organic solvents which can be used include, e.g., N,N-dimethylformamide, acetonitrile, dichloromethane, and the like. This reaction is typically carried out at temperatures in the range of about 0° C. to about 80° C. The reaction is continued until completion, which typically occurs from 2 to 24 hours.

Step 6-2: Compound 30 can be converted compound 31 by using a reducing agent. For example, this transformation can be accomplished by reaction with a borane such as BH$_3$-Me$_2$S complex or BH$_3$/THF in a suitable solvent such as tetrahydrofuran, ethyl alcohol and methyl alcohol. Other suitable reducing agents are LiAlH$_4$ in dry ether at room temperature.

Step 6-3: The quaternization of the tertiary amine in compound 31 can be performed as described in step 1-3.

Step 6-4: N-Deprotection may be carried out as described in step 1-4 to provide compound 33.

Step 6-5: Compound 33 can then be converted to the corresponding N,N-dihalo- or N-haloamine 34 as described in step 1-4.

Scheme 7: Alternative Synthesis of Ammonium Compounds of Formula IA and IC

Ammonium compounds of Formula IA and IC can also be prepared by the reaction steps as shown in Scheme 7.

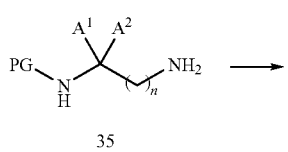

35

36

37

38

Step 7-1: N-Monoprotected diamine 35 can be alkylated as described in step 1-3 to provide compound 36.

Step 7-2: N-Deprotection of 36 may be carried out as described in step 1-4 to provide compound 37.

Step 7-3: Compound 37 can then be converted to the corresponding N,N-dihalo- or N-haloamine 38 as described in step 1-4.

Scheme 8: Alternative Synthesis of Ammonium Compounds of Formulae IA and IC

In addition, ammonium compounds of Formula IA and IC can also be prepared by the reaction steps as shown in Scheme 8.

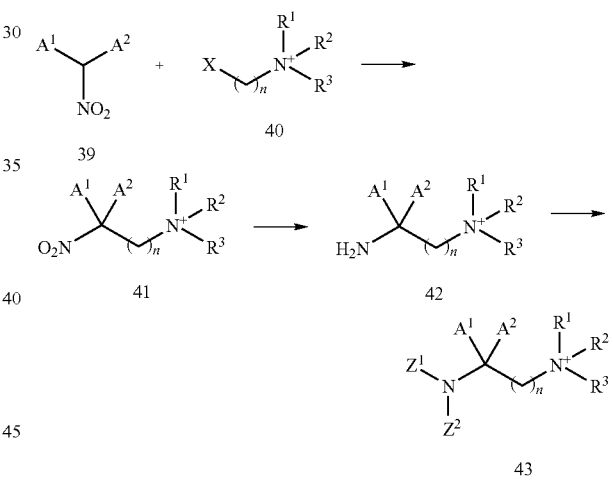

39  40

41  42

43

Step 8-1: Nitro compound 39 can be reacted with alkyl halide 40 (wherein X is, e.g., Cl, Br, I, —OSO$_2$CH$_3$ or —OSO$_2$CF$_3$) under basic reaction conditions, preferably in an inert organic solvent, in the presence of an organic base to provide nitro compound 41. Suitable organic bases include benzyltrimethylammonium hydroxide, lithium diisopropylamine, N,N-diisopropyl ethylamine, triethylamine, pyridine, N-methyl morpholine, and the like. Suitable inert organic solvents which can be used include N,N-dimethylformamide, acetonitrile, dichloromethane, and the like. This reaction is typically conducted at temperatures in the range of about 0° C. to 100° C. The reaction is continued until completion, typically in about 2 to 24 hours.

Step 8-2: Nitro compound 41 can be converted to the corresponding amine 42 by hydrogenation in the presence of hydrogenation catalyst, such as Raney Nickel, Pd on carbon, and the like, or by treatment with aqueous acid in the presence of metal e.g. iron, tin and the like. N-Deprotection is carried out in a polar organic solvent such as ethanol or methanol.

Palladium hydrogenations are typically carried out under a hydrogen atmosphere at ambient temperatures and at a pressure from 15 psi to 500 psi in about 1 to 24 hours.

Step 8-3: Compound 42 is converted to the corresponding N,N-dihalo- or N-haloamine 43 as described in step 1-4.

Scheme 9: Sulfonium Compounds

Sulfonium compounds of Formula I can be prepared by the reaction steps as shown in Scheme 9.

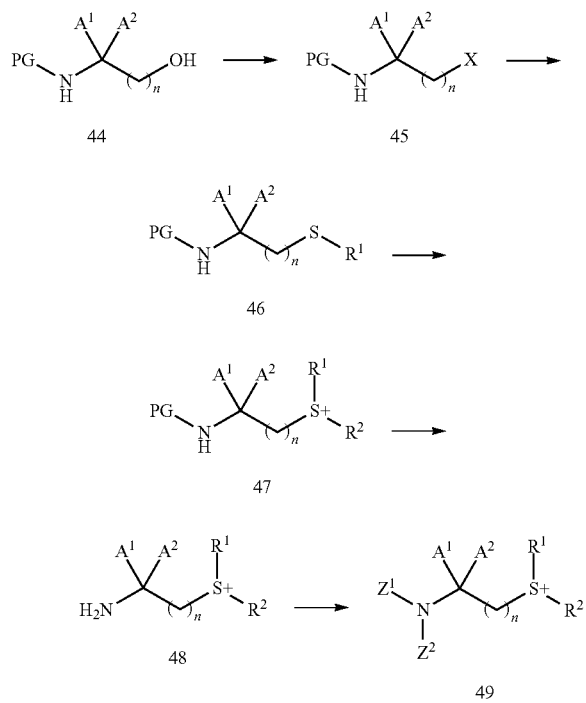

Scheme 10: Phosphonium Compounds

Phosphonium compounds of Formula I can be prepared by the reaction steps as shown in Scheme 10.

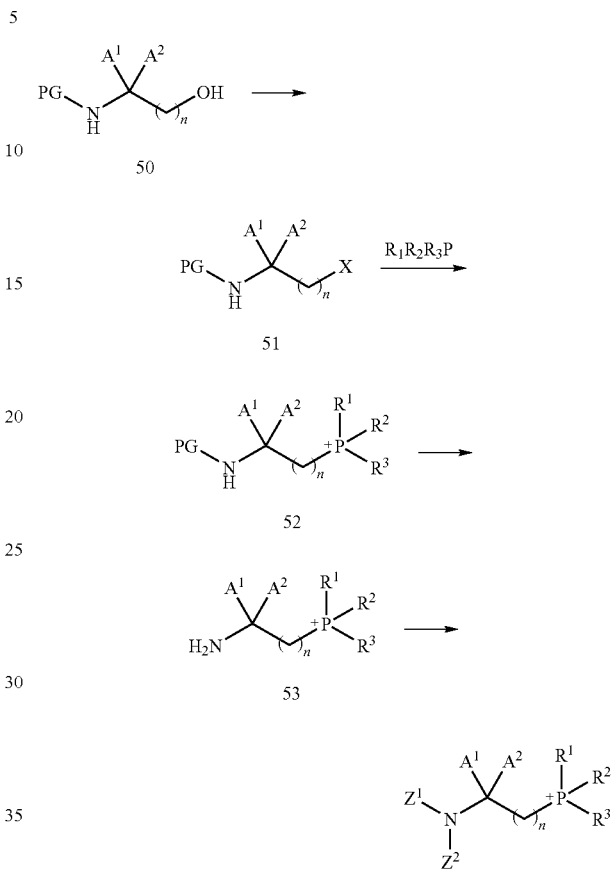

Step 9-1: Alcohol 44 can be converted to compound 45, which contains leaving group X. For example, X may be chloride and formed by the reaction of alcohol 44 with an alkanesulfonyl chloride in the presence of base followed by the reaction with a halogenating agent such as a chloride source. Suitable inert organic solvents include dichloromethane, tetrahydrofuran, and the like. The reaction is typically conducted at temperatures in the range of about 0° C. to 50° C. The reaction is continued until completion, which typically in about 2 to 24 hours. In another example, X may be trifluoromethane sulfonate, a substituted aryl sulfonate, or the like.

Step 9-2: Compound 45 can be converted thioalkyl compound 46 by reaction with a sodium thioalkoxide in a suitable organic solvents such as N,N-dimethylformamide, acetonitrile, methylenechloride, tetrahydrofuran, and the like. The reaction is typically carried out at ambient temperature to 100° C. for about 2 to 24 hours.

Step 9-3: Compound 46 can then be treated with an alkylating agent such as an alkyl halide to provide sulfonium 47, under similar reaction conditions described in step 1-3 for the alkylation of amines to ammonium compounds.

Step 9-4: N-Deprotection of 47 may be carried out as described in step 1-4 to provide compound 48.

Step 9-5: Compound 48 can then be converted to the corresponding N,N-dihalo- or N-haloamine 49 as described in step 1-4.

Step 10-1: Compound 51 can be prepared by reacting N-protected amine 50 with an alkanesulfonyl chloride in the presence of a suitable base followed by the reaction with a halogenating agent as described in step 9-1. Suitable inert organic solvents include methylenechloride, tetrahydrofuran, and the like. The reaction is typically conducted at temperatures in the range of about 0° C. to 100° C. The reaction is continued until completion, typically in about 2 to 24 hours.

Step 10-2: Compound 51 can be transformed to the corresponding trialkylphosphonium derivative 52 by reaction with a trialkylphosphine in a polar organic solvent such as 2-butanone, ethyl methyl ketone, ethanol, and the like. The reaction is typically carried out in the range of about 25° C. to 130° C. for about 12 to 24 hours under pressure ranging from 200 psi to 500 psi.

Step 10-3: N-Deprotection of 52 may be carried out as described in step 1-4 to provide compound 53.

Step 10-4: Compound 53 can then be converted to the corresponding N,N-dihalo- or N-haloamine 54 as described in step 1-4.

Scheme 11: 1,2,3-Triazole-Containing Compounds 1,2,3-Triazole-containing compounds of Formula IA and IC can be prepared by the reaction steps as shown in Scheme 11.

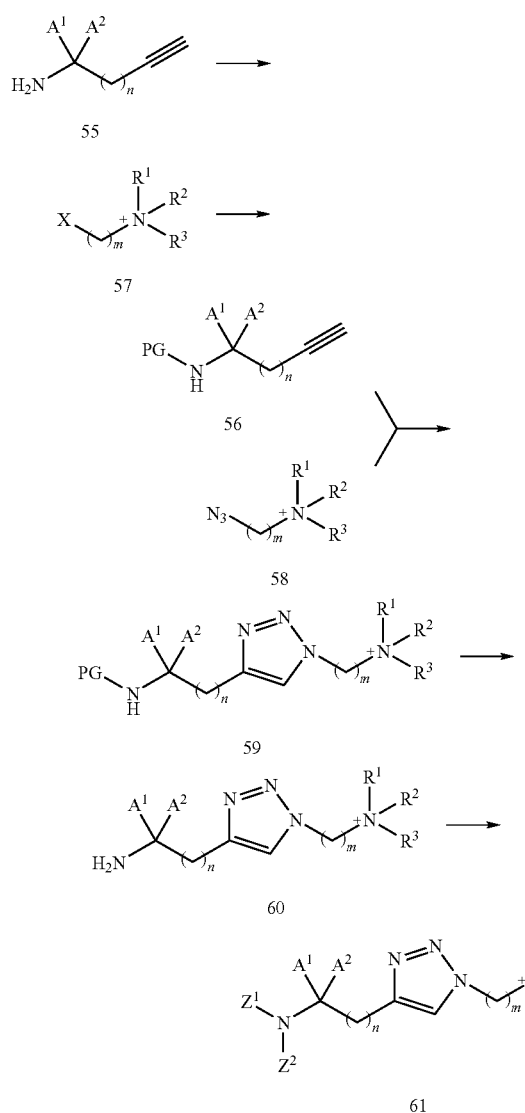

Step 11-4: N-Deprotection of 59 may be carried out as described in step 1-4 to provide compound 60.

Step 11-5: Compound 60 can then be converted to the corresponding N,N-dihalo- or N-haloamine 61 as described in step 1-4.

Scheme 12: Heteroaryl-Containing Compounds

Heteroaryl-containing compounds of Formula IA and IC can be prepared by the reaction steps as shown in Scheme 12. As shown in Scheme 12, the dotted line is intended to depict the aromatic nature of the heteroaryl. A single or double bond may be present depending on the identity of T, U, V, W and p.

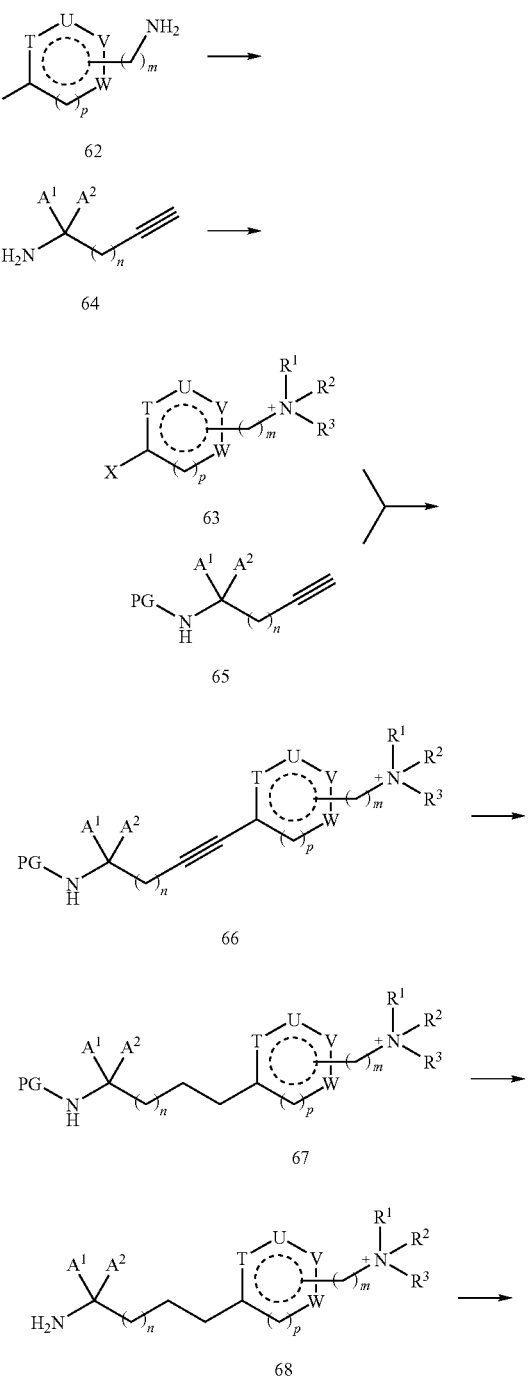

Step 11-1: Compound 55 can be optionally protected with an amine protection group, such as N-benzyloxycarbonyl (Cbz) or tert-butyloxycarbonyl (Boc). The Boc protection group can be added by reacting amine 55 with di-tert-butyl dicarbonate in an inert organic solvent such as tetrahydrofuran at ambient temperatures in about 1 to 24 hours. The Cbz protection group can be added by treating the amine 55 with benzyl chloroformate in an inert organic solvent such as dichloromethane or tetrahydrofuran at 0° C. to ambient temperatures in about 5 minutes to 2 hours.

Step 11-2: Compound 57 (wherein X is, e.g., Cl, Br, I, —$OSO_2CH_3$ or —$OSO_2CF_3$) can be converted to the azide 58 by reaction with sodium azide or potassium azide in a suitable inert solvent, i.e., one that can dissolve a salt, such as N,N-dimethylformamide. The reaction is typically conducted between room temperature to 120° C. for 2 to 24 hours.

Step 11-3: Compounds 56 and 58 can be converted to triazole 59 under copper catalyzed reaction conditions, such as with the use of copper iodide or copper sulfate, and an organic base, such as N,N-diisopropyl ethylamine or sodium ascorbate, in a polar solvent, such as water, methanol, ethanol, tetrahydrofuran, and the like. The reaction is typically conducted at room temperature for 8 to 48 hours.

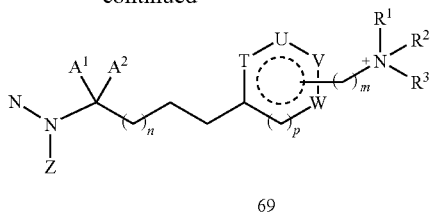

69

Step 12-1: The quarternization of the amine in compound 62 (wherein X is, e.g., Cl, Br or I; wherein T, U, V and W are independently N, O, S or CH; and p is 0 or 1) can be carried out using an alkylating agent as described in step 1-3 in the presence or absence of a base to provide compound 63. Suitable alkylating agents include alkyl halides, such as methyl iodide, and the like. The alkylation may be conducted neat with excess of alkylating agent or in an inert organic solvent such as, e.g., N,N-dimethylformamide, acetonitrile, dichloromethane, alcohols and N-methylpyridone. Suitable bases include, N,N-diisopropyl ethylamine, triethylamine, cesium carbonate and the like. The reaction is typically conducted at room temperature to 100° C. for about 16 to about 48 hours.

Step 12-2: Amine 64 can be protected with a suitable protecting group, such as tert-butyloxycarbonyl (Boc). The Boc protecting group can be added by reacting amine 64 with di-tert-butyl dicarbonate in an inert organic solvent such as tetrahydrofuran at ambient temperatures in about 1 to 24 hours.

Step 12-3: Aryl halide 63 and acetylene 65 can be coupled under the usual Sonogashira coupling conditions [see, e.g. *Chem. Rev.*, 107, 874-922 (2007)] to give compound 66.

Step 12-4: Acetylene 66 can then be converted to compound 67 by hydrogenation in the presence of hydrogenation catalyst, such as Pd on carbon. The hydrogenation is typically carried out under a hydrogen atmosphere at ambient temperature and at pressure from 15 psi to 100 psi in about 1 to 24 hours.

Step 12-5: N-Deprotection of 67 may be carried out as described in step 1-4 to provide compound 68.

Step 12-6: Compound 68 is then converted to the corresponding N,N-dihalo- or N-haloamine 69 as described in step 1-4.

Scheme 13: Charged Heteroaryl-Containing Compounds

Heteroaryl-containing compounds of Formula I can be prepared by the reaction steps as shown in Scheme 13. As shown in Scheme 13, the dotted line is intended to depict the aromatic nature of the heteroaryl. A single or double bond may be present depending on the identity of U, V, Z, $R^3$, and p.

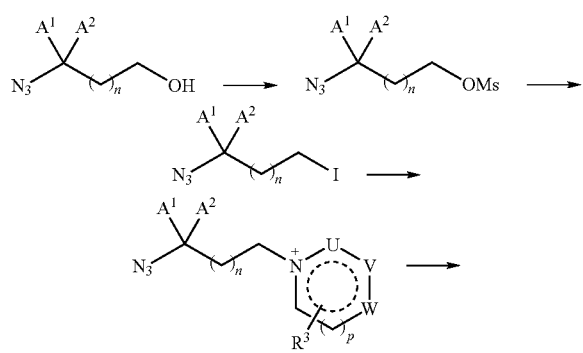

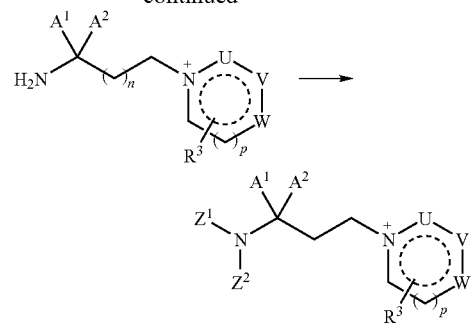

Step 13-1: Compound 71 can be prepared by reacting alcohol 70 with methanesulfonyl chloride in the presence of a suitable base followed by the reaction with a halogenating agent as described in step 9-1. Suitable inert organic solvents include methylenechloride, tetrahydrofuran, and the like. Suitable bases include triethylamine, diisoproylethylamine, and the like. The reaction is typically conducted at temperatures in the range of about 0° C. to 100° C. The reaction is continued until completion, typically in about 1 to 24 hours.

Step 13-2: Iodide 72 can be prepared by reacting compound 71 with iodide ion, such as sodium iodide, potassium iodide, and the like, inert organic solvent. Suitable inert organic solvents include N,N-dimethylformamide, acetone, and the like. The reaction is typically conducted at temperatures in the range between 0° C. to 100° C. The reaction is continued until completion, typically in about 1 to 24 hours.

Step 13-3: Compound 73 can be prepared by reacting iodide 72 with heteroaryl reagent in the presence of an inert organic solvent. Suitable inert organic solvents include methylenechloride, tetrahydrofuran, methanol and the like. The reaction is typically conducted at temperatures in the range between room temperature to 180° C. for approximately 4 to 48 hours.

Step 13-4: Amine 74 can be prepared by hydrogenation of compound 73 in a polar solvent with a palladium catalyst under hydrogen gas. Suitable palladium catalysts include 10% palladium on carbon, 5% palladium on carbon, 5% palladium on barium sulfate, and the like. Suitable inert organic solvents include ethanol, methanol and the like. The reaction is typically conducted at temperatures in the range between room temperature to 80° C. for approximately 4 to 48 hours under hydrogen gas ranging from 1 to 10 atmospheres of pressure.

Step 13-4: Compound 74 is then converted to the corresponding N,N-dihalo- or N-haloamine 75 as described in step 1-4.

More specific synthetic routes to illustrative compounds of Formula I are given in the Examples below.

Salts (including pharmaceutically acceptable salts) of the compounds of the present application may be prepared by reacting the free acid or base moieties of these compounds, where present, with a stoichiometric or greater amount of the appropriate base or acid in water or in an organic solvent, or in a mixture of the two; generally, e.g., non-aqueous media like ether, ethyl acetate, ethanol, isopropanol. The salts of the present application may also be prepared by ion exchange.

Compounds of Formula I may be formulated as a solid. For example, such solids may consist primarily of a compound of Formula I as a salt. Compositions comprising one or more compounds of Formula I and one or more other substances may be formed, and may take the form of aerosols, creams, emulsions, gels, lotions, ointments, pastes, powders, solutions, suspensions and other forms of the active ingredient.

Compositions may include multiple (e.g. two or more) compounds of Formula I. The compositions may further comprise other active ingredients, such as HOCl or other antimicrobial agents.

Compositions or formulations may include a pharmaceutically acceptable carrier, as defined above. By way of example, the compositions of the present application may include the following pharmaceutically acceptable carriers: sodium chloride to attain isotonicity, buffers, stabilizers, solvents, flavoring agents (in case of oral or nasopharyngeal administration or the food industry), preserving agents, diluents, extenders and other auxiliary substances or excipients. Examples of pharmaceutically acceptable carriers and excipients that may be used are described in *Remington: The Science and Practice of Pharmacy*, R. Hendrickson, ed., 21st edition, Lippincott, Williams & Wilkins, Philadelphia, Pa., (2005) at pages 317-318, which are hereby incorporated by reference in their entireties. In general, water, saline, oils, alcohols (e.g. 2-propanol, 1-butanol, etc.), polyols (e.g. 1,2-propanediol, 2,3-butanediol, etc.), and glycols (e.g. propylene glycol, polyethylene glycols, etc.) may be suitable carriers for solutions. In one aspect solutions contain the active ingredient in a water soluble or aqueous medium soluble form, e.g. as a salt, together with suitable stabilizing agents and if necessary, buffer substances.

For example, compounds of Formula I may be formulated with cyclodextrin or cyclodextrin derivatives, including cyclodextrin sulfobutyl ether (Capisol®, Cyclex, Overland Park, Kans., USA). These and other carriers may be used to improve or otherwise modulate the solubility, penetration, uptake and other properties of compositions comprising the compounds described herein.

Aerosols can range from colloidal dispersions to formulations designed for pressurized delivery. Modes of operation include liquefied-gas systems, compressed-gas systems and barrier-type systems.

Creams are viscous liquids or semisolid emulsions, either oil-in-water or water-in-oil. Cream bases are water-washable, and contain an oil phase, an emulsifier and an aqueous phase. The oil phase, also called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant.

Emulsions are two-phase systems prepared by combining two immiscible liquids, in which small globules of one liquid are dispersed uniformly throughout the other liquid. Emulsions may be designated as oil-in-water or water-in-oil type emulsions. Certain emulsions may not be classified as such because they are described by another category, such as a lotion, cream, and the like.

Gels are semisolid, suspension-type systems. Single-phase gels contain organic macromolecules distributed substantially uniformly throughout the carrier liquid, which is typically aqueous, but also, e.g., contain an alcohol such as ethanol or isopropanol and, optionally, an oil. Exemplary gelling agents include crosslinked acrylic acid polymers such as the "carbomer" family of polymers, e.g., carboxypolyalkylenes that may be obtained commercially under the Carbopol® trademark (Lubrizol Corporation, Wickliffe, Ohio, USA). Also useful are hydrophilic polymers such as polyethylene oxides, polyoxyethylene-polyoxypropylene copolymers and polyvinylalcohol; cellulosic polymers such as hydroxypropyl cellulose, hydroxyethyl cellulose, hydroxypropyl methylcellulose, hydroxypropyl methylcellulose phthalate, and methyl cellulose; gums such as tragacanth and xanthan gum; sodium alginate; and gelatin. In order to prepare a uniform gel, dispersing agents such as alcohol or glycerin can be added, or the gelling agent can be dispersed by trituration, mechanical mixing or stirring, or combinations thereof.

Lotions are preparations generally applied to the skin surface so as to avoid high friction, and are typically liquid or semiliquid preparations in which solid particles, including the active agent, are present in a water or alcohol base. Lotions are usually suspensions of solids, and, e.g., comprise a liquid oily emulsion of the oil-in-water type. Lotions can be used to large body areas, because of the ease of applying a generally fluid composition. It is generally necessary that the insoluble matter in a lotion be finely divided. Lotions will typically contain suspending agents to produce better dispersions as well as compounds useful for localizing and holding the active agent in contact with the skin, e.g., methylcellulose, sodium carboxymethyl-cellulose, or the like.

Ointments are semi-solid preparations that are typically based on petrolatum or other petroleum derivatives. The specific ointment base to be used is one that will provide for optimum active ingredient delivery, and other desired characteristics, e.g., emolliency. As with other carriers or vehicles, an ointment base should be inert, stable, nonirritating and nonsensitizing. Ointment bases may be grouped in four classes: oleaginous bases, emulsifiable bases, emulsion bases and water-soluble bases. Oleaginous ointment bases include, e.g., vegetable oils, fats obtained from animals, and semisolid hydrocarbons obtained from petroleum. Emulsifiable ointment bases, also known as absorbent ointment bases, contain little or no water and include, e.g., hydroxystearin sulfate, anhydrous lanolin and hydrophilic petrolatum. Emulsion ointment bases are either water-in-oil (W/O) emulsions or oil-in-water (O/W) emulsions, and include, e.g., cetyl alcohol, glyceryl monostearate, lanolin and stearic acid. For example, water-soluble ointment bases are prepared from polyethylene glycols of varying molecular weight.

Pastes are semisolid dosage forms in which the active agent is suspended in a suitable base. Depending on the nature of the base, pastes are divided between fatty pastes or those made from single-phase aqueous gels. The base in a fatty paste is generally petrolatum or hydrophilic petrolatum or the like. The pastes made from single-phase aqueous gels generally incorporate carboxymethylcellulose or the like as a base.

Suspensions may be defined as a coarse dispersion containing finely divided insoluble material suspended in a liquid medium.

Formulations may also be prepared with liposomes, micelles, and microspheres.

Various additives may also be included in formulations, e.g. to solubilize the active ingredients. Other optional additives include opacifiers, antioxidants, fragrances, colorants, gelling agents, thickening agents, stabilizers, surfactants and the like.

These and other compositions or formulations suitable for carrying and delivering compounds of Formula I, IA, IB and IC are described in Chapters 22, 39, 43, 45, 50 and 55 of *Remington*, above, which are hereby incorporated by reference in their entireties.

The concentration of compounds of Formula I or their salts in compositions, formulations, and dosage forms may be up to the saturation concentration of compounds of Formula I, IA, IB or IC or their salts, e.g., up to about 1 M (molar), up to about 500 mM (milimolar), or up to about 150 mM. For example, compositions of the present application comprise a composition having a concentration of compounds of Formula I, IA, IB or IC or their salts ranging from about 0.001 mM to about 1 M, from about 0.01 mM to about 500 mM, from about 0.05 mM to about 150 mM, from about 0.1 mM to about 10 mM, and about 0.5 mM to about 2 mM. Compositions of the present application can also have a concentration of compounds of Formula I, IA, IB and IC or their salts ranging from about 0.1 μg/ml to about 300 g/L, about 1 μg/ml to about 150 g/L, from about 5 μg/ml to about 45 g/L, from about 10 μg/ml to about 3000 μg/ml and about 50 μg/ml to about 600 μg/ml. In a further aspect, compositions of the present application comprise isotonic and physiologically balanced solutions of compounds of Formula I, IA, IB and IC or their salts.

In certain embodiments the compositions in form of solutions are osmotically balanced. In further embodiments, the compositions described herein have a therapeutic index ranging from about 10 to about 10,000, e.g. from about 100 to about 1000.

The compounds of Formula I, IA, IB and IC or their salts, are useful in methods of preventing or treating microbial (e.g. bacterial, viral, or fungal) infection or contamination. Compounds described herein may also be administered to prevent or treat a disease, disorder, ailment, or other pathology caused by bacteria, fungus, virus, or associated biofilm. The compounds or salts described herein may also be used for the preparation of a medicine for the prevention or treatment of microbial infection, contamination or activity in a subject. Such methods comprise administering or applying an effective amount of the compound or salt thereof in or near the area of interest, e.g. in or near a tissue or organ, to a surface of a medical device, within a storage container, and so on.

Compositions of the present application are useful in a wide range or applications in which antimicrobial properties are desirable. Such applications include, without limitation, treatment or reduction of pathogens on or in the integumentary system, including the skin, nails and hair, or mucous membranes, including wounds, surgical sites, and so forth. Applications and areas of interest include wounds, burns, ulcers, inflammation or lesions of the skin, the eyes, ears, nasal passages, sinus, bronchpulmonary system, vagina, rectum and other mucous membranes or related tissues. Applications include treatment of viral conditions such as cold sores, warts, and molluscum contagiosum; dermatological bacterial conditions such as acne, impetigo, cellulitis, erysipelas, cutaneous abcesses, folliculitis, furuncles (boils), and paronychial infections; the treatment of various fungal infections such as onychomycosis (fungal nail infections on fingers and toes); acute or chronic rhinosinusitis or other infections such as otitis, dermatitis, bronchitis, pneumonias such as *Pneumocystis carinii*, fungal infections of urinary, reproductive or sex organs such as vulvovaginal candidosis, colpitis, endometritis, balanitis; infections of the gastrointestinal tract such as stomatitis, oesophagitis, enteritis, or fungal infections of the urethra such as pyelonephritis, ureteritis, cystitis, or urethritis (including, e.g., urinary tract infection, such as catheter-associated urinary tract infection ("CAUTI"); use in lavage, reduction of infectious load in organs for transplantation; reduction of bacterial load in autologous or artificial tissue transplantation; cleaning of tissue sites (e.g., pre- and post-operative surgical preparation); ophthalmic applications (e.g. treatment of viral or bacterial conjunctivitis, cleaning solutions or irrigation of the eye, and, e.g., treatment of tissue before, during, or after ophthalmic surgery); nasal or nasopharyngeal applications including, but not limited to, the treatment of rhinosinusitis or rhinitis caused by viral, bacterial or fungal infections; dental applications including oral disinfection, the treatment of gingivitis or periodontitis; reduction of pathogens in pulmonary infections; treatment of biofilm (e.g. for cystic fibrosis or other diseases that produces biofilms); and animal health applications (e.g. treatment of mastitis). Administration of compositions for these applications may be topical, e.g., topical application to the skin or mucous membranes (e.g. the mouth, nose, eye, ear, vagina, rectum).

Applications also include use in vaccine formulations (as preservative and potentially adjuvant), viral inactivation of both DNA and RNA classes of viruses including HIV, hepatitis A, respiratory syncytial virus, rhinovirus, adenovirus, West Nile virus, HSV-1, HSV-2, SARS, influenza and parainfluenza viruses, picornaviruses, and vaccinia virus (as a model for poxviruses).

Furthermore, the compositions described herein have antimicrobial activity against many other microorganisms, including *Hemophilus influenzae, Escherichia coli, Enterococcus faecium, Enterococcus faecalis, Listeria monocytogenes, Staphylococcus aureus*, methicillin-resistant *S. aureus* (MRSA), *Staphylococcus epidermidis, Streptococcus pneumoniae, Pseudomonas aeruginosa, Proteus mirabilis, Klebsiella pneumoniae, Lactobacillus, Acinetobacter junii*, yeast, including *Candida albicans*, vancomycin-resistant *enterococcus*, molds, and spores, including spores of anthrax and cysts of Acanthamoeba. Vancomycin-resistant enterococci and staphylococci, MRSA, and others can be destroyed by the compositions of the present application. Examples of bacteria implicated in periodontal disease and destroyed by the compositions of the present application are *Bacteroides gingivalis, Bacillus intermedius, Actinomyces actinomycetemcomitans* and *Bacteroides forsythus*. Examples of bacteria that are implicated in mastitis (infection of cow udder) and killed by the compositions are *Streptococcus agalactiae* and *Streptococcus infantarius*. The compositions destroy biofilms and are therefore effective against micro-organisms growing in both planktonic form and in biofilms.

While N-halogenated and N,N-dihalogenated compounds of Formulae I, IA, IB and IC may have inherent antimicrobial activity, the corresponding protonated (i.e. non-halogenated) analogs may also have antimicrobial activity, or may be activated to an antimicrobial (or increased antimicrobial) state by a source of halogen. For example, it is well known that hypochlorite and/or hypochlorous acid is generated by neutrophils, eosinophils, mononuclear phagocytes, and B lymphocytes [see, e.g., L. Wang et al., *J. Burns Wounds*, 6, 65-79 (2007) and M. Nagl et al., *Antimicrob. Agents Chemother.* 44(9) 2507-13 (2000)]. Certain organic cloramines, including N-chlorotaurine, have been detected in the supernatants of stimulated granulocytes, and are thought to prolong the oxidative capacity of these cells during oxidative burst and to protect cells from damage by $HOCL/OCl^-$. In a similar fashion to taurine, N-protonated and N,N-diprotonated compounds of Formulae I, IA, IB and IC, in or near these cells may be chlorinated during oxidative burst, and may serve a similar microbicidal and/or protective effect. Thus, compounds of Formulae I, IA, IB and IC may be used in methods to generate antimicrobial activity in situ, to prolong or otherwise modulate the oxidative capacity of cells during oxidative burst, or to decrease associated cyclotoxicity.

The compounds described herein may also be useful in a method to treat, disinfect, or decontaminate surfaces or areas, including to kill or reduce or inhibit the growth of bacteria, fungi or viruses, the method comprising the administration of an effective amount of the compound or salt thereof to the surface. Applications include the elimination or reduction of pathogens on or in medical devices (including surgical, dental, optical, and other), equipment and instruments, (e.g. breathing tubes, catheters, contact lenses, dental implants and equipment, equipment used for organ preservation, hearing aids, prostheses, stents, etc.), devices, food (e.g., meats, fish, fruits, vegetables, nuts, etc.) and food contact surfaces (e.g. cutting tools, storage rooms or containers, etc.) including the elimination or reduction of bacterial biofilms, and agricultural uses including protection of seed stocks.

By way of example, compositions of the present application may be applied to tissues such as the skin directly, via an applicator, aerosol or spray, or incorporated into bandages or wound dressings. The compositions, which may be in the form of solutions, pastes, creams, gels or lotions, and may be used in combination with specially designed bandages in a wound treatment protocol. For example, a bandage may include (or be impregnated with) a gauze, gel, ointment, or similar means to allow the antimicrobial composition to contact the area of interest, e.g. the wound or infection. A bandage may also include an opening or "window" through which topical treatment materials such as the solution of the present application may be applied, reapplied, circulated, etc. The compositions may also be applied in applications (e.g. treatment of burns) where it is desirable to maintain a moist and sterile environment without disturbing the dressing. In one such example, a perforated tube is placed between the dressing and the outer bandage or wrap. Periodically, the composition is passed through the tube thus irrigating the dressing with fresh antimicrobial solution.

In another example, compounds and compositions of the present application may be used for the eradication of bacteria (including bacteria in a biofilm), such as, but not limited to, bacterial and biofilms in or on medical devices, e.g. in the lumen of a catheter (e.g. urinary, central venous, hemodialysis catheters and the like), stent, breathing tube, etc. Such methods may include the destruction of the corresponding biofilm matrix to clear the bacterial load from the medical device, such as improving or maintaining patency in the lumen of a catheter, stent, or breathing tube. Biofilms are a group of microorganisms attached to a substrate and are often associated with the excretion of extracelullar polymeric substance [R. M. Donlan et al., *Clin. Microbiol. Rev.*, 4, 167-193 (2002)]. The demonstrated resistance of biofilms to antimicrobials has caused problems in human health and has had a significant impact on the success of medical implants, e.g., catheters [J. W. Costerton et al., *Science*, 284(5418), 1318-22 (1999)]. Once catheters are colonized, biofilms will develop on the outer and inner surfaces and cause infections. Reduction of the bacterial load by prevention of the formation of biofilm [J. F. Williams and S. D. Worley, *J. Endourology*, 14(5), 395-400 (2000); K. Lewis and A. M. Klibanov, *Trends in Biotech.*, 23, 7, 343-348 (2005)], destruction of an existing biofilm [P. Wood et al., *Appl. Env. Microb.* 62(7), 2598-2602 (1996)] and killing bacteria in biofilm [P. Gilbert and A. J. McBain, *Am. J. Infect. Control*, 29, 252-255 (2001)] are strategies towards lowering microbial load and reducing biofilm-related infection from any catheters and shunts, such as but not limited to, urinary and central venous catheters, implanted artificial joints, implanted artificial hearts, gastric feeding tubes, and colostomy tubes.

Compounds described herein may be used to treat, eradicate, or prevent the formation of biofilm formed by a variety of bacteria and fungi, including, but not limited to, gram-positive cocci, gram-negative rods, *P. aeruginosa*, *C. albicans*, *S. aureus*, *B. cepacia*, *E. coli*, *S. epidermidis*, *A. hydrophila*, *H. influenzae*, *S. liquifaciens*, *P. mirabilis*, *K. pneumoniae*, and *P. vulgaris*. A discussion of these, and examples of other, biofilm-forming species may be found in, e.g., S. Kjelleberg, and S. Molin, *Curr Opin Microbiol.*, June, 5(3):254-8 (2002); J. W. Consterton et al., *Science*, 284, May 21, 1318-11 (1999); and D. J. Stickler et al., *Methods in Enzymology*, 310: 494-501 (1999).

In another application of treating, disinfecting, decontaminating or cleaning medical devices, a solution of a compound of the present application may be used to cleanse contact lenses. Such solutions may also contain additional preservatives and disinfecting agents as well as cleaning and other agents. These solutions may be used to store contact lenses (e.g., in packaging, between uses, in carrying cases, etc.), to condition lenses, to wet or re-wet lenses before insertion into the eye, or to clean, disinfect or rinse lenses. Disinfection of contact lenses is important in the prevention of infections of the eye caused by micro-organisms. Microbes are primarily introduced to the eye by handling of the lens. For example, introduction of *E. coli* may lead to infections of various eye structures, such as microbial keratitis. Fungal pathogens, such as *Fusarium*, can also infect the eye when transferred from a colonized contact lens. [See, e.g., J. K. Suchecki et al., *Opthalmol. Clin. North Am.*, 16(3), 471-84 (2003).]

EXAMPLES

The following examples are offered by way of illustration and not by way of limitation.

The starting materials and reagents used in preparing the compounds described herein are either available from commercial suppliers such as Aldrich-Sigma Chemical Co. (Milwaukee, Wis., USA), Bachem (Torrance, Calif., USA), Toronto Research Chemicals (North York, ON, Canada), Anaspec (San Jose, Calif., USA), Chem-Impex International (Wood Dale, Ill., USA), Spectrum (Gardena, Calif., USA), PharmaCore (High Point, N.C., USA) or are prepared by methods known to those skilled in the art following procedures set forth in the literature and references such as *Fieser's Reagents for Organic Synthesis*, Volumes 1-12 (Wiley-Interscience, 1999), *March's Advanced Organic Chemistry*, (Wiley-Interscience, 6th Edition, 2007), and M. C. Pirrung, *The Synthetic Organic Chemist's Companion* (John Wiley & Sons, Inc., 2007).

Example 1

2-(3-(Dichloroamino)-N,3-dimethylbutanamido)-N,N,N-trimethylethanaminium chloride (Compound 21-14)

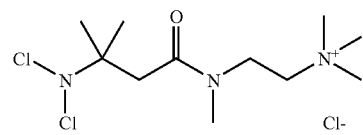

Benzyl 4-((2-(dimethylamino)ethyl)(methyl)amino)-2-methyl-4-oxobutan-2-ylcarbamate

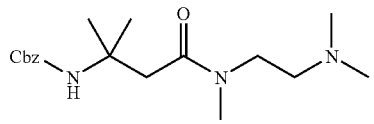

To a solution of 3-(benzyloxycarbonylamino)-3-methylbutanoic acid (described in international publication number WO 2008/083347 A1) (5.74 g, 22.9 mmol) in N,N-dimethylformamide (150 ml) was added N,N-carbonyldiimidazole (4.45 g, 27.4 mmol). The reaction mixture was stirred for 1 hour at room temperature. N,N-diisoproylethylamine (11.2 ml, 68.8 mmol) and N,N,N-trimethylethylenediamine (3.6 ml, 27.8 mmol) were added was added to the reaction mixture. The mixture was stirred for an additional 18 hours at room temperature. The reaction mixture was poured into water and was extracted with ethyl acetate. The organic layer was washed two more times with water and dried over sodium sulfate. The dried organic layer was filtered and concentrated in vacuo. The crude product was purified on silica gel column chromatography (0 to 10% methanol in dichloromethane) to give 2.08 g (27% yield) of benzyl 4-((2-(dimethylamino)ethyl)(methyl)amino)-2-methyl-4-oxobutan-2-ylcarbamate. $^1$H NMR (CDCl$_3$) δ 7.34-7.26 (m, 5 H), 6.14 (s, 1 H), 5.04 (s, 2 H), 3.47 (t, J=5.3 Hz, 2 H), 3.02 (s, 3 H), 2.60 (s, 2 H), 2.59 (t, J=5.3 Hz, 2 H), 2.24 (s, 6 H), 1.46 (s, 6 H); MS (ESI+) calculated for $C_{18}H_{30}N_3O_3$: 335.23, Found: 336.2 (M+H+).

2-(3-(Benzyloxycarbonylamino)-N,3-dimethylbutanamido)-N,N,N-trimethylethanaminium iodide

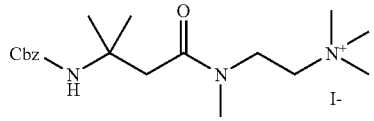

Benzyl 4-((2-(dimethylamino)ethyl)(methyl)amino)-2-methyl-4-oxobutan-2-ylcarbamate (2.08 g, 6.2 mmol) was dissolved in a solution of ethanol (4 ml) and methyl iodide (30 ml). The mixture was stirred at 50° C. for 18 hours. The reaction mixture was concentrated in vacuo and dissolved in water. The aqueous mixture was washed with ethyl acetate. The washed aqueous mixture concentrated in vacuo to give 2.19 g (74%) of 2-(3-(benzyloxycarbonylamino)-N,3-dimethylbutanamido)-N,N,N-trimethylethanaminium iodide. MS (ESI+) calculated for $C_{19}H_{32}N_3O_3^+$: 350.24, Found: 350.2 (M+).

2-(3-amino-N,3-dimethylbutanamido)-N,N,N-trimethylethanaminium hydrochloride

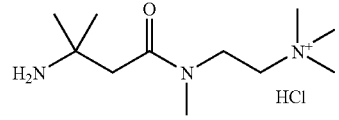

2-(3-(Benzyloxycarbonylamino)-N,3-dimethylbutanamido)-N,N,N-trimethylethanaminium iodide (2.19 g, 4.6 mmol) was dissolved in hydrogen bromide (33% in acetic acid, 30 ml) was stirred at room temperature for 3 hours. Ether was added to the reaction mixture and the white precipitate was filtered off. The solid material was dissolved in water (100 ml) and silver oxide (6.00 g) was added. The suspension was stirred for 30 minutes, and the solution was filtered through Celite®. The aqueous solution was acidified with concentrated hydrogen chloride (6 ml), and the mixture was filtered again through Celite®. The aqueous solution was concentrated and purified by prep-HPLC to give 511 mg (44%) of 2-(3-amino-N,3-dimethylbutanamido)-N,N,N-trimethylethanaminium hydrochloride. $^1$H NMR (D$_2$O) δ 3.87 (t, J=5.7 Hz, 2 H), 3.53 (t, J=5.7 Hz, 2 H), 3.19 (s, 9 H), 3.11 (s, 3 H), 2.81 (s, 2 H), 1.42 (s, 6 H); calc. for $C_{11}H_{26}N_3O+$: 216.21, Found: 216.2 (M+).

2-(3-(dichloroamino)-N,3-dimethylbutanamido)-N,N,N-trimethylethanaminium chloride

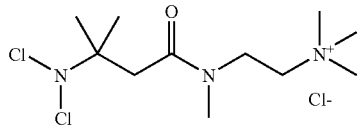

To a solution of 2-(3-amino-N,3-dimethylbutanamido)-N,N,N-trimethylethanaminium hydrochloride (511 mg, 2.0 mmol) in methanol (40 ml) was added tert-butylhypochlorite (0.77 g, 7.1 mmol). The mixture was stirred for 1 hour at room temperature. The reaction mixture was concentrated in vacuo, and purified by prep-HPLC to give 253 mg (39%) of 2-(3-(dichloroamino)-N,3-dimethylbutanamido)-N,N,N-trimethylethanaminium chloride. $^1$H NMR (D$_2$O) δ 3.88 (t, J=5.4 Hz, 2 H), 3.53 (t, J=5.4, 2 H), 3.26 (s, 3 H), 3.21 (s, 9 H), 2.98 (s, 2 H), 1.51 (s, 6 H); calc. for $C_{11}H_{24}C_{12}N_3O^+$: 284.13, Found: 284.1 (M+).

Example 2

2-(Dichloroamino)-N,N,N-2-tetramethylpropan-1-ammonium chloride (Compound 21-30)

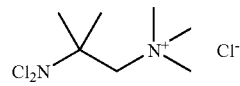

N,N-2-Trimethyl-2-nitropropan-1-amine

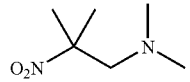

Following the methods reported in T. Ueda and T. Tsuji, Chem. Pharm. Bull., 12, 946-950 (1964); H. G. Johnson, J. Am. Chem. Soc., 68, p. 12 (1946); M. Senkus, J. Am. Chem. Soc., 68, p. 10 (1946); and M. Senkus, U.S. Pat. No. 2,419,506, a stirred ice cold solution of 2-nitropropane (27.0 mL, 0.3 mol) and 40% aqueous dimethylamine (33.8 mL, 1 equiv, 0.3 mol) was added dropwise a 37% solution of formaldehyde (24.3 mL, 1 equiv, 0.3 mol) over 1 h. The flask was removed from the ice bath and stirred at room temperature for 1 h. The reaction was then heated at 50° C. for 1 h. The cooled solution was poured into a separatory funnel and extracted with ether (3×150 mL). The organic layer was washed with water (2×100 mL) and brine (100 mL). The organic layer was dried over anhydrous MgSO$_4$, filtered and concentrated to a yellow oil. The oil was vacuum distilled through a short path distillation apparatus. The forerun (30-61° C., 9 mbar) was discarded and the main fraction (61-65° C., 9 mbar) was collected as a pale yellow liquid (26.8 g, 61.1%). $^1$H NMR (CDCl$_3$, 400 MHz): δ 1.56 (s, 6H), 2.27 (s, 6H), 2.79 (s, 2 H). LRMS (ESI+) for C$_6$H$_{14}$N$_2$O$_2$ (146.1); Found: 147 (MH+).

N$^1$,N$^1$,2-Trimethylpropane-1,2-diamine

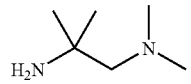

N,N-2-Trimethyl-2-nitropropan-1-amine (11.00 g, 77.7 mmol) was dissolved into anhydrous THF (50 mL, 0.2 M) and added dropwise to an ice cold suspension of LAH (5.89 g, 2.0 equiv) in anhydrous THF over 1 h. The reaction was left to stir at 0° C. for 30 min. The flask was fitted with a condenser and the reaction was heated in a 70° C. oil bath for 17 h. The reaction mixture was cooled in an ice bath and water (5.9 mL) was added dropwise over 20 min. Then 15% NaOH solution (5.9 mL) was added dropwise over 10 min. The suspension was stirred for a further 10 min and water (12.0 mL) was in one portion and the mixture stirred for 30 min to give a fine white suspension. The suspension was filtered through a pad of Celite® and the solids washed with THF (3×100 mL). The combined filtrate was carefully concentrated on a rotovap with the bath temperature set to 20° C. to give a pale yellow liquid (5.68 g, yield: 62.9%). The crude amine was used without further purification. $^1$H NMR (CDCl$_3$, 400 MHz): δ 1.41 (s, 6H), 2.51 (s, 2H), 2.98 (s, 2 H). LRMS (ESI+) for C$_6$H$_{16}$N$_2$ (116.1); Found: 117 (MH+).

Benzyl 1-(dimethylamino)-2-methylpropan-2-ylcarbamate

N$^1$,N$^1$,2-Trimethylpropane-1,2-diamine (5.68 g, 48.8 mmol) was dissolved into isopropanol/water (1:1, 150 mL). To this solution was added CbzOSu (12.2 g, 1 equiv, 48.8 mmol) in one portion. The reaction was left to stir at room temperature overnight for 17 h. The solvent was removed and the residue was taken up in a mixture of ethyl acetate (300 mL) and water (100 mL). The layers were separated and the organic layer extracted with water (2×100 mL). The organic layer was dried over anhydrous MgSO$_4$, filtered and concentrated to an oil. The crude oil was purified on an ISCO purification system with gradient elution from 2% methanol in DCM to 30% methanol in DCM. The desired fraction was collected and concentrated to give a colorless oil (8.95 g, yield: 73.2%). $^1$H NMR (CDCl$_3$, 400 MHz): δ 1.41 (s, 6H), 2.51 (s, 2H), 2.98 (s, 2 H). LRMS (ESI+) for C$_{14}$H$_{22}$N$_2$O$_2$ (250.2); Found: 251 (MH+).

2-(Benzyloxycarbonylamino)-N,N,N-2-tetramethylpropan-1-ammonium chloride

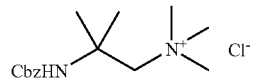

Benzyl 1-(dimethylamino)-2-methylpropan-2-ylcarbamate (4.0 g, 16.0 mmol) was placed into a 15 mL pressure tube. Methanol (2.4 mL, 6.8 M) and methyl iodide (2.0 mL, 2 equiv, 32.0 mmol) was added to the reaction. A stir bar was added and the pressure tube sealed. The reaction was left to stir for 17 h. The thick suspension was filtered and rinsed with a small amount of methanol and dried under high vacuum to give a white solid (5.48 g, 87.3%). This solid was dissolved into water (100 mL) and Ag$_2$O (2.41 g, 0.65 equiv, 10.04 mmol) was added in one portion. The black suspension immediately changed to a cream color suspension. The reaction was stirred at room temperature for 3 h and the solid filtered through a pad of Celite®. The solid was washed with water (50 mL) and the filtrate acidified with 6 M HCl until the filtrate was pH 2. The filtrate was concentrated via rotovap to give a white powder. The white powder was dried over P$_2$O$_5$ to give (4.10 g, quantitative from iodide and 85.2%). $^1$H NMR (CDCl$_3$, 400 MHz): δ 1.41 (s, 6H), 2.51 (s, 2H), 2.98 (s, 2 H). LRMS (ESI+) for C$_{15}$H$_{25}$N$_2$O$_2$$^+$ (265.2); Found: 265 (M+).

2-Amino-N,N,N-2-tetramethylpropan-1-ammonium chloride hydrochloride

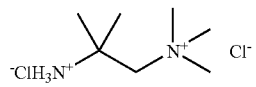

2-(Benzyloxycarbonylamino)-N,N,N-2-tetramethylpropan-1-ammonium chloride (3.14 g, 10.4 mmol) was dissolved into methanol and water (1:1, 100 mL). The flask was flushed with nitrogen for 5 min and 10% Pd/C was added to the reaction in one portion. The flask was sealed and degassed with vacuum and flushed with hydrogen from a balloon (3×). The reaction was stirred at room temperature for 17 h. The suspension was filtered through a pad of Celite® and the solid was washed with methanol water (1:1, 50 mL). The filtrate was concentrated to a viscous oil. The oil was dried under high vacuum over P$_2$O$_5$ to give a hygroscopic white foam (1.52 g, 87.6%). $^1$H NMR (CDCl$_3$, 400 MHz): δ 1.41 (s, 6H), 2.51 (s, 2H), 2.98 (s, 2 H). LRMS (ESI+) for C$_7$H$_{19}$N$_2$$^+$ (131.2); Found: 131 (M+).

2-(Dichloroamino)-N,N,N-2-tetramethylpropan-1-ammonium chloride

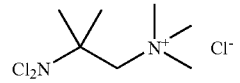

A solution of 2-amino-N,N,N-2-tetramethylpropan-1-ammonium chloride hydrochloride (5.0 g, 24.6 mmol) in a mixture of methanol (20 mL) and water (10 mL) was cooled in an ice bath for 15 min. t-BuOCl (2.57 mL, 2.5 equiv, 22.8 mmol) was added in one portion via syringe to the colorless solution to give a deep yellow solution. The reaction mixture was stirred for 30 min at 0° C., then concentrated under reduced pressure to yield a white solid. This solid was dissolved into water and purified via reverse phase chromatography on a Shimadzu Prep-LC utilizing water/acetonitrile and 0.05% acetic acid as modifier. Fractions were collected monitoring UV absorbance at 254 nm. Fractions were pooled and concentrated via rotovap with the water bath set at 25° C. to give a white solid, (3.99 g, 68.8%). $^1$H NMR (CDCl$_3$, 400 MHz): δ 1.41 (s, 6H), 2.51 (s, 2H), 2.98 (s, 2 H). LRMS (ESI+) for $C_7H_{17}Cl_2N_2^+$ (199.1); Found: 199, 201 (M+, M2H+).

Example 3

3-(Dichloroamino)-N,N,N-3-tetramethylbutan-1-ammonium chloride (Compound 21-32)

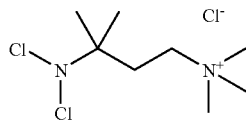

3-Azido-3-methylbutanoic acid

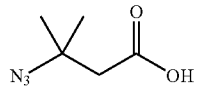

According to the method of S, Nagarajan and B. Ganem, *J. Org. Chem.*, 51, 4856, (1986), sodium azide (52 g, 0.8 mol) in water (100 mL) was added to a stirred solution of 3,3-dimethylacrylic acid (20 g, 0.2 mol) in glacial acetic acid (50 mL) in one portion. The clear yellow solution was stirred for 1 h at RT, then heated in an oil bath at 95° C. for 2 days. Water (50 mL) was added to the cooled orange solution. This solution was poured into a separatory funnel and extracted with ether (5×200 mL). The combined organic extracts were dried over anhydrous MgSO$_4$ and concentrated to an orange oil. This oil was used without further purification.

3-Azido-3-methylbutanoyl chloride

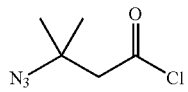

To a stirred solution of 3-azido-3-methylbutanoic acid (10 g, 69.8 mmol) in anh. dichloroethane (50 mL) was added thionyl chloride in one portion (10.0 mL, 2 equiv, 0.14 mol). The flask was fitted with a condenser and the reaction was heated in a 50° C. oil bath for 2 h. The reaction was concentrated to a brown-black suspension. The residue was vacuum distilled through a short path distillation apparatus. The fore-run was discarded and the major fraction distilled at 66° C. at 18 mbar as a pale yellow liquid (9.66 g, 85.6%). $^1$H NMR (CDCl$_3$, 400 MHz): δ 1.41 (s, 6H), 2.51 (s, 2H), 2.98 (s, 2 H).

3-Azido-N,N-3-trimethylbutanamide

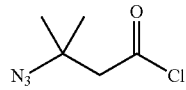

To a stirred ice cold solution of 3-azido-3-methylbutanoyl chloride (9.66 g, 59.8 mmol) in anhydrous DCM (150 mL) was added a solution of 40% aqueous dimethylamine (23.7 mL, 3 equiv, 0.18 mol) in one portion. A white solid formed immediately and the suspension was stirred vigorously until a clear biphasic mixture formed. The speed of stirring was reduced and the reaction was left at 0° C. for 1 h. DCM (200 mL) was added to the reaction mixture and the contents poured into a separatory funnel. The organic layer was separated and washed with water (3×50 mL) and brine (50 mL). It was dried over anhydrous MgSO$_4$, filtered, concentrated and dried under high vacuum to give a crude oil (10.16 g, quant). This material was used without further purification.

$N^1,N^1$-3-Trimethylbutane-1,3-diamine

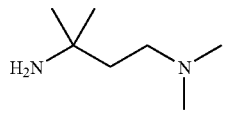

A solution of 3-azido-N,N-3-trimethylbutanamide (10.2 g, 59.7 mmol) in anhdrous THF (100 mL, 0.2 M) was added dropwise to an ice cold suspension of LAH (4.50 g, 2.0 equiv, 0.12 mol) in anhydrous THF (150 mL) over 1 h. After complete addition, the flask was fitted with a condenser and the reaction heated in a 70° C. oil bath for 4 h. The reaction mixture was removed from the bath and stirred at room temperature for 17 h. The reaction mixture was cooled in an ice bath and water (3.5 mL) was added dropwise over 20 min. Then 15% NaOH solution (3.5 mL) was added dropwise over 10 min. The suspension was stirred for a further 10 min and water (7.0 mL) was added in one portion and the mixture stirred for 30 min to a give fine white suspension. The suspension was filtered through a pad of Celite® and the white cake was re-suspended into diethyl ether (200 mL) to give a white granular solid. The suspension was filtered and the cake washed with diethyl ether (2×100 mL) and the combined filtrate was carefully concentrated on a rotovap with the bath temperature set to 20° C. to give a pale yellow liquid which was briefly dried under high vacuum to give 8.15 g (yield: 105%,). The crude amine was not dried completely to minimize loss of product due to its low b.p. and used without further purification.

Benzyl 4-(dimethylamino)-2-methylbutan-2-ylcarbamate

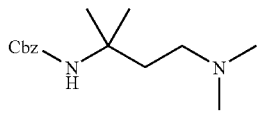

Solid CbzOSu (15.6 g, 1 equiv, 48.8 mmol) was added in one portion to a solution of $N^1,N^1$-3-trimethylbutane-1,3-diamine (8.15 g, 62.6 mmol) in THF (100 mL). The reaction was left to stir at room temperature for 17 h. The solvent was removed and the residue was taken up in a mixture of ethyl acetate (500 mL) and water (100 mL). The layers were separated and the organic layer washed with saturated sodium bicarbonate (2×100 mL), water (100 mL) and brine (100 mL). The organic layer was dried over anhydrous $MgSO_4$, filtered and concentrated to a pale yellow oil. The crude oil was purified on an ISCO purification system with gradient elution from 1-5% methanol in DCM. The desired fractions were collected and concentrated to give a colorless oil (11.49 g, yield: 69.6%). $^1$H NMR ($CDCl_3$, 400 MHz): δ 1.35 (s, 6H), 1.67-1.72 (t, J=6.6, 2H), 2.23 (s, 6H), 2.36-2.40 (t, J=7.2, 2H), 6.46 (s, 1H), 7.27-7.36 (m, 5H), LRMS (ESI+) for $C_{15}H_{24}N_2O_2$ (264.2); Found: 265 (MH+).

3-(Benzyloxycarbonylamino)-N,N,N-3-tetramethylbutan-1-ammonium iodide

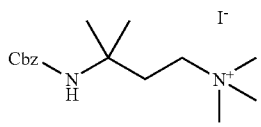

Benzyl 4-(dimethylamino)-2-methylbutan-2-ylcarbamate (4.0 g, 15.2 mmol) was placed into a 15 mL pressure tube. Methanol (2.2 mL, 6.8 M) and methyl iodide (1.89 mL, 2 equiv, 32.0 mmol) was added to the reaction. A stir bar was added and the pressure tube sealed. The reaction was left to stir at room temperature for 17 h. The solution had become a solid cake. The solid was filtered and rinsed with a small amount of methanol and dried under high vacuum to give a white crystalline solid (6.03 g, 97.0%). $^1$H NMR ($CD_3OD$, 400 MHz): δ 1.31 (s, 6H), 2.20-2.27 (m, 2H), 3.04 (s, 9H), 3.28-3.33 (m, 6H), 5.04 (s, 2H), 7.30-7.39 (m, 5H). LRMS (ESI −ve) for $C_{16}H_{27}N_2O_2^+$ (279.2); Found: 279 (M+).

3-Amino-N,N,N-3-tetramethylbutan-1-ammonium chloride hydrochloride

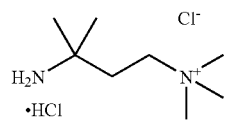

3-(Benzyloxycarbonylamino)-N,N,N-3-tetramethylbutan-1-ammonium iodide (6.03 g, 15.2 mmol) was dissolved into water (150 mL) and $Ag_2O$ (2.28 g, 0.65 equiv, 9.88 mmol) was added in one portion. The black suspension immediately changed to a cream color suspension. The reaction was stirred at room temperature for 17 h. The red-black solid was filtered through a pad of Celite® and the solid was washed with water (50 mL). The filtrate concentrated to give the crude product (6.0 g) which was dissolved into a methanol-water mixture (1:1, 80 mL). The flask was flushed with nitrogen for 5 min and 10% Pd/C (200 mg) was added to the reaction in one portion. The flask was sealed and degassed with vacuum and flushed with hydrogen from a balloon (3×). The reaction was stirred at room temperature for 17 h. The suspension was filtered through a pad of Celite® and the solid was washed with methanol-water (1:1, 50 mL). The filtrate was acidified with 6 M HCl to pH 2, and then concentrated to a viscous oil. The oil was dried under high vacuum over $P_2O_5$ to give a hygroscopic white foam (1.65 g, 50%). $^1$H NMR (D$_2$O, 400 MHz): δ 1.43 (s, 6H), 2.18-2.22 (m, 2H), 3.19 (s, 9H), 3.50-3.56 (m, 2H). LRMS (ESI+) for $C_8H_{21}N_2^+$ (145.2); Found: 145 (M+).

3-(Dichloroamino)-N,N,N-3-tetramethylbutan-1-ammonium chloride

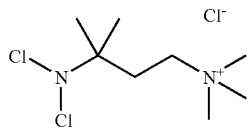

A solution of 3-amino-N,N,N-3-tetramethylbutan-1-ammonium chloride hydrochloride (0.7289 g, 3.35 mmol) in methanol (10 mL) was cooled in an ice bath for 15 min. t-BuOCl (2.57 mL, 2.5 equiv, 22.8 mmol) was added in one portion via syringe to the colorless solution to give a deep yellow solution. The reaction mixture was stirred for 30 min at 0° C., then concentrated under reduced pressure to yield a white solid. This solid was dissolved into water and purified via reverse phase chromatography on a Shimadzu Prep-LC utilizing water/acetonitrile and 0.05% acetic acid as modifier. Fractions were collected monitoring UV absorbance at 254 nm. Fractions were pooled and concentrated via rotovap with the water bath set at 25° C. to give a white solid, (0.60 g, 71.7%). $^1$H NMR (D$_2$O, 400 MHz): δ 1.45 (s, 6H), 2.25-2.30 (m, 2H), 3.15 (s, 9H), 3.45-3.50 (m, 2H). LRMS (ESI+) for $C_8H_{19}Cl_2N_2^+$ (213.1); Found: 213 (M+).

Example 4

4-(2-(Dichloroamino)-2-methylpropyl)-4-methylmorpholin-4-ium chloride (Compound 21-74)

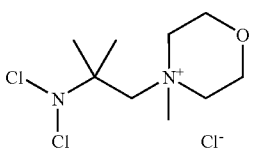

tert-Butyl 2-methyl-1-morpholinopropan-2-ylcarbamate

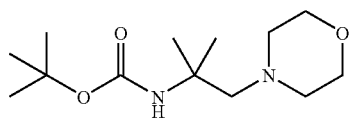

2-Methyl-1-morpholinopropan-2-amine (430 mg, 2.7 mmol) and di-tert-butyl dicarbonate (593 mg, 2.7 mmol) were dissolved in tetrahydrofuran (25 ml). The reaction mixture was stirred at room temperature for 18 hours. The reaction mixture was concentrated in vacuo, and the crude material was dissolved in ethyl acetate. The solution was washed with aqueous sodium bicarbonate solution. The organic layer was dried over sodium sulfate and concentrated in vacuo to give 640 mg (91%) of tert-butyl 2-methyl-1-morpholinopropan-2-ylcarbamate. $^1$H NMR (CDCl$_3$) δ 4.62 (s, 1 H), 3.70-3.67 (m, 4 H), 2.57-2.54 (m, 4 H), 2.45 (s, 2 H), 1.43 (s, 9 H), 1.26 (s, 6 H); MS (ESI+) calculated for C$_{13}$H$_{27}$N$_2$O$_3$: 258.20, Found: 259 (M+H).

4-(2-(tert-Butoxycarbonylamino)-2-methylpropyl)-4-methylmorpholin-4-ium iodide

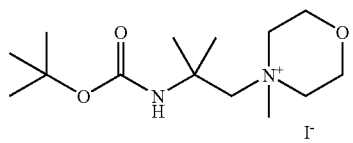

tert-Butyl 2-methyl-1-morpholinopropan-2-ylcarbamate (640 mg, 2.5 mmol) was dissolved in methyl iodide (20 ml) and placed in a sealed tube. The reaction was stirred at 50° C. for 18 hours. The reaction mixture was concentrated and partitioned between water and ethyl acetate. The water layer was separated and concentrated to give 840 mg (85%) 4-(2-(tert-butoxycarbonylamino)-2-methylpropyl)-4-methylmorpholin-4-ium iodide. $^1$H NMR (D$_2$O): δ (m, 4 H), 3.83 (s, 2 H), 3.72-3.54 (m, 4 H), 3.37 (s, 3 H), 1.50 (s, 6 H), 1.45 (s, 9 H); MS (ESI+) calculated for C$_{14}$H$_{29}$N$_2$O$_3^+$: 273.22, Found: 273 (M$^+$).

4-(2-Amino-2-methylpropyl)-4-methylmorpholin-4-ium chloride

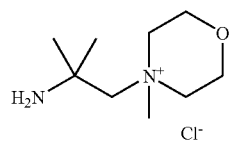

4-(2-(tert-Butoxycarbonylamino)-2-methylpropyl)-4-methylmorpholin-4-ium iodide (840 mg, 2.1 mmol) was dissolved in methanol (5 ml). To the solution was added 4M hydrogen chloride in dioxane (25 ml), and stirred for 4 hours at room temperature. The reaction mixture was concentrated and dissolved in water. Silver oxide (1.0 g) was added to the aqueous solution and the mixture was stirred at room temperature for 30 minutes. The solution was filtered through Celite®, and concentrated hydrochloric acid (0.5 ml) was added to the solution. The solution was filtered through Celite® a second time, and the aqueous solution was concentrated in vacuo to give 380 mg (87%) of 4-(2-amino-2-methylpropyl)-4-methylmorpholin-4-ium chloride. MS (ESI+) calculated for C$_9$H$_{21}$N$_2$O$^+$: 173.16, Found: 173 (M$^+$).

4-(2-(Dichloroamino)-2-methylpropyl)-4-methylmorpholin-4-ium chloride

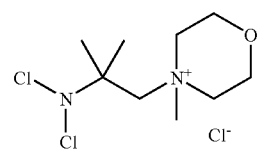

tert-Butyl hypochlorite (0.49 mg, 4.5 mmol) was added to a stirred solution of 4-(2-amino-2-methylpropyl)-4-methylmorpholin-4-ium chloride (380 mg, 1.8 mmol) in methanol (25 ml) and stirred for 1 hour at room temperature. The reaction mixture was concentrated in vacuo, and purified by prep-HPLC to give 64 mg (13% yield) of 4-(2-(dichloroamino)-2-methylpropyl)-4-methylmorpholin-4-ium chloride. $^1$H NMR (D$_2$O) δ 4.16-3.98 (m, 4 H), 3.86 (s, 2 H), 3.78-3.58 (m, 4 H), 3.43 (s, 3 H), 1.66 (s, 6H); MS (ESI+) calculated for C$_9$H$_{19}$Cl$_2$N$_2$O$^+$: 241.09, Found: 241 (M$^+$).

Example 5

2-(4-(2-(Dichloroamino)propan-2-yl)-1H-1,2,3-triazol-1-yl)-N,N,N-trimethylethanaminium chloride (Compound 21-92)

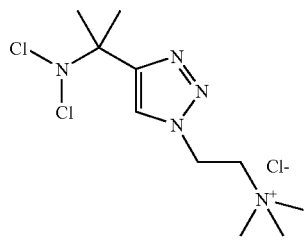

tert-Butyl-methylbut-3-yn-2-ylcarbamate

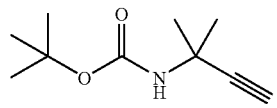

2-Methylbut-3-yn-2-amine (5.11 g, 61.5 mmol) and di-t-butyl dicarbonate (13.4 g, 61.5 mmol) were dissolved in tetrahydrofuran (100 ml). The reaction mixture was stirred at room temperature for 18 hours. The reaction mixture was concentrated in vacuo, and the crude material was dissolved in ethyl acetate. The solution was washed with aqueous sodium bicarbonate solution. The organic layer was dried over sodium sulfate and concentrated in vacuo to give 10.4 g (92%) of tert-butyl 2-methylbut-3-yn-2-ylcarbamate as a white solid. $^1$H NMR (CDCl$_3$) δ 4.69 (s, 1 H), 2.30 (s, 1 H), 1.58 (s, 6 H), 1.46 (s, 9 H); C$_{10}$H$_{18}$NO$_2$: 183.13. Found: 184.1 (M+H).

2-Azido-N,N,N-trimethylethanaminium bromide

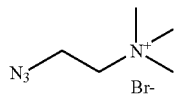

(2-Bromoethyl)trimethylammonium bromide (6.60 g, 26.7 mmole) and sodium azide (1.73 g, 26.6 mmole) were dissolved in water (150 ml). The mixture was stirred for 2 hours at 90° C. The reaction mixture was concentrated to give 8.20 g of crude 2-azido-N,N,N-trimethylethanaminium bromide, which contained a small amount of starting material and sodium bromide. The product was used in the next step without further purification. $^1$H NMR (D$_2$O) δ 3.97-3.95 (m, 2 H), 3.61-3.58 (m, 2 H), 3.21 (s, 9 H); MS (ESI+) calculated for C$_5$H$_{13}$N$_4^+$: 166.02, 168.02. Found: 166.0, 168.0 (M+, M2H+).

2-4-2-tert-Butoxycarbonylamino)propan-2-1-1H-1,2, 3-triazol-1-1-N,N,N-trimethylethanaminium bromide

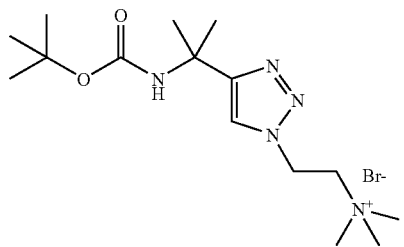

Crude 2-azido-N,N,N-trimethylethanaminium bromide (8.20 g), tert-butyl 2-methylbut-3-yn-2-ylcarbamate (3.78 g, 20.63 mmol), and N,N-diisopropylethylamine (5.7 ml, 35.0 mmol) were dissolved in methanol (300 ml). Copper iodide (330 mg, 1.72 mmol) was added to the solution, and the combined reaction mixture was stirred 18 hours at room temperature. The reaction mixture was concentrated, and the crude material was purified by prep-HPLC (5-95% gradient of water/methanol with 0.05% acetic acid) to give 6.20 g (59% for 2 steps) of 24442-(tert-butoxycarbonylamino)propan-2-yl)-1H-1,2,3-triazol-1-yl)-N,N,N-trimethylethanaminium bromide. $^1$H NMR (D$_2$O) δ 8.06 (s, 1 H), 5.04 (t, J=4.8 Hz, 2 H), 4.03 (t, J=5.0 Hz, 2 H), 3.19 (s, 9 H), 1.62 (s, 6 H), 1.37-1.30 (m, 9 H); MS (ESI+) calculated for C$_{15}$H$_{30}$N$_5$O$_2^+$: 312.24. Found: 312.3 (M+).

2-(4-(2-Aminopropan-2-yl)-1H-1,2,3-triazol-1-yl)-N,N,N-trimethylethanaminium hydrochloride

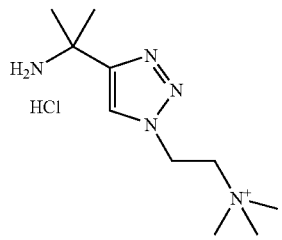

2-(4-(2-(tert-Butoxycarbonylamino)propan-2-yl)-1H-1,2, 3-triazol-1-yl)-N,N,N-trimethylethanaminium bromide (6.20 g, 15.8 mmol) was dissolved in methanol (15 ml). To the solution was added 4M hydrogen chloride in dioxane (150 ml), and the combined reaction mixture was stirred for 4 hours at room temperature. The reaction mixture was concentrated and dissolved in water. Silver oxide (6.0 g) was added to the aqueous solution and the mixture was stirred at room temperature for 30 minutes. The solution was filtered through Celite®, and concentrated hydrochloric acid (2 ml) was added to the solution. The solution was filtered through Celite® a second time, and the aqueous solution was concentrated in vacuo. The crude material was purified by prep-HPLC (5-95% gradient of water/methanol with 0.05% acetic acid) to give 3.29 g (84%) 2-(4-(2-aminopropan-2-yl)-1H-1, 2,3-triazol-1-yl)-N,N,N-trimethylethanaminium hydrochloride. $^1$H NMR (D$_2$O) δ 8.27 (s, 1H), 5.07 (t, J=5.0 Hz, 2 H), 4.03 (t, J=5.1 Hz, 2 H), 3.21 (s, 9 H), 1.78 (s, 6 H); MS (ESI+) calculated for C$_{10}$H$_{22}$N$_5^+$: 212.19. Found: 212.2 (M+).

2-(4(2-(Dichloroamino)propan-2-yl)-1H-1,2,3-triazol-1-yl)-N,N,N-trimethylethanaminium chloride

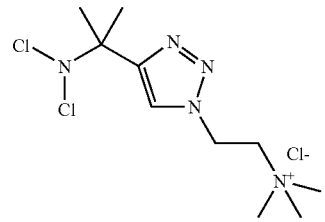

A solution of 2-(4-(2-aminopropan-2-yl)-1H-1,2,3-triazol-1-yl)-N,N,N-trimethylethanaminium hydrochloride (1.45 g, 5.8 mmol) in methanol (100 ml) was stirred at room temperature. t-Butyl hypochlorite (1.90 g, 17.5 mmol) was added to the mixture, and the combined mixture was stirred for 1 hour at room temperature. The reaction mixture was concentrated in vacuo, and purified by prep-HPLC to give 769 mg (42% yield) of 2-(4-(2-(dichloroamino)propan-2-yl)-1H-1,2,3-triazol-1-yl)-N,N,N-trimethylethanaminium chloride. $^1$H NMR (D$_2$O) δ 8.41 (s, 1 H), 5.10 (t, J=4.7, 2 H), 4.06 (t, J=4.7, 2 H), 3.18 (s, 9 H), 1.83 (s, 6H); MS (ESI+) calculated for C$_{10}$H$_{20}$Cl$_2$N$_5^+$: 280.11. Found: 280.1 (M+).

Example 6

1-(2-(3-(Dichloroamino)-3-methylbutanoyloxy) ethyl)-1-methylpiperidinium chloride (Compound 21-93)

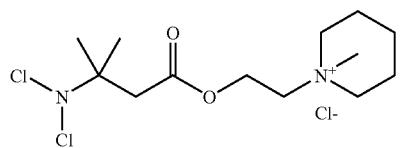

2-(Piperidin-1-yl)ethyl 3-(benzyloxycarbonylamino)-3-methylbutanoate

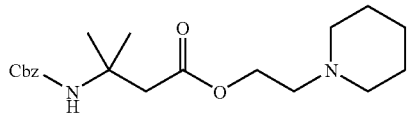

To a solution of 3-(benzyloxycarbonylamino)-3-methylbutanoic acid (reported in international publication number WO 2008/083347 A1) (9.18 g, 36.5 mmol) in N,N-dimethylformamide (200 ml) was added N,N-carbonyldiimidazole (6.52 g, 40.2 mmol). The reaction mixture was stirred for 1 hour at room temperature followed by the addition of 1-(2-hydroxyethyl)piperidine (36.3 ml, 47.4 mmol) was added was added to the reaction mixture. The mixture was stirred for an additional 18 hours at room temperature. The reaction mixture was poured into water and was extracted with ethyl acetate. The organic layer was washed two more times with water and dried over sodium sulfate. The dried organic layer was filtered and concentrated in vacuo. The crude product was purified column chromatography (0 to 10% methanol in dichloromethane) to give 9.45 g (71% yield) of 2-(piperidin-1-yl)ethyl 3-(benzyloxycarbonylamino)-3-methylbutanoate. $^1$H NMR (CDCl$_3$) δ 7.44-7.26 (m, 5 H), 5.47 (s, 1 H), 5.06 (s, 2 H), 4.19 (t, J=6.0 Hz, 2 H), 2.69 (s, 2 H), 2.50 (t, J=6.0 Hz, 2 H), 2.40-2.32 (m, 4 H), 1.60-1.48 (m, 4 H) 1.46-1.36 (m, 8 H); MS (ESI+) calculated for $C_{20}H_{31}N_2O_4$: 362.23, Found: 363.2 (M+H$^+$).

1-(2-(3-(Benzyloxycarbonylamino)-3-methylbutanoyloxy)ethyl)-1-methylpiperidinium iodide

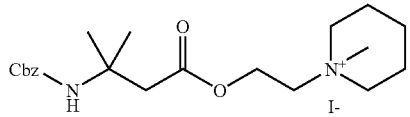

A batch of 2-(piperidin-1-yl)ethyl 3-(benzyloxycarbonylamino)-3-methylbutanoate (9.45 g, 26.1 mmol) was dissolved in a solution of dichloromethane (40 ml) and methyl iodide (16.3 ml, 262 mmole). The mixture was stirred at room temperature for 18 hours. The reaction mixture was concentrated in vacuo, and the crude material was purified by pre-HPLC to give 8.74 g (66%) of 1-(2-(3-(benzyloxycarbonylamino)-3-methylbutanoyloxy)ethyl)-1-methylpiperidinium iodide. $^1$H NMR (CD$_3$OD) δ 7.39-7.27 (m, 5 H), 5.05 (s, 2 H), 4.52-4.47 (m, 2 H), 3.70-3.64 (m, 2 H), 3.44-3.37 (m, 4 H), 3.09 (s, 3 H), 2.84 (s, 2 H), 1.92-1.86 (m, 4 H), 1.73-1.59 (m, 2 H), 1.39 (s, 6 H). MS (ESI+) calculated for $C_{21}H_{33}N_2O_4^+$: 377.24, Found: 377.2 (M$^+$).

1-(2-(3-Amino-3-methylbutanoyloxy)ethyl)-1-methylpiperidinium hydrochloride

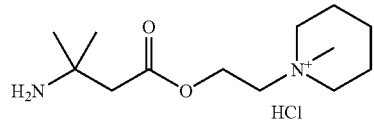

A batch of 1-(2-(3-(benzyloxycarbonylamino)-3-methylbutanoyloxy)ethyl)-1-methylpiperidinium iodide (2.00 g, 4.0 mmol) was dissolved in hydrogen bromide (33% in acetic acid, 30 ml) and stirred at room temperature for 3 hours. The reaction mixture was concentrated, and the oil was dissolved in water (100 ml). Silver (II) oxide (10.00 g) was added. The suspension was stirred for 30 minutes, and the solution was filtered through Celite®. The aqueous solution was acidified with concentrated hydrogen chloride (6 ml), and the mixture was filtered again through Celite®. The aqueous solution was concentrated to give 1.01 g (91%) of 1-(2-(3-amino-3-methylbutanoyloxy)ethyl)-1-methylpiperidinium hydrochloride. $^1$H NMR (D$_2$O) δ 4.67-4.60 (m, 2 H), 3.81-3.74 m, 2 H), 3.54-3.37 (m, 4 H), 3.14 (s, 3 H), 2.85 (s, 2 H), 1.96-1.85 (m, 4 H), 1.75-1.59 (m, 2 H), 1.44 (s, 6 H); calc. for $C_{11}H_{26}N_3O^+$: 243.21, Found: 243.1 (M$^+$).

1-(2-(3-(Dichloroamino)-3-methylbutanoyloxy)ethyl)-1-methylpiperidinium chloride

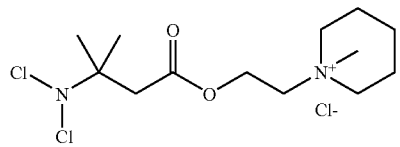

To a solution of 1-(2-(3-amino-3-methylbutanoyloxy)ethyl)-1-methylpiperidinium hydrochloride (1.01 g, 3.6 mmol) in methanol (40 ml) was added tert-butylhypochlorite (1.00 g, 9.2 mmol). The mixture was stirred for 1 hour at room temperature. The reaction mixture was concentrated in vacuo, and purified by prep-HPLC to give 560 mg (45%) of 14243-(dichloroamino)-3-methylbutanoyloxy)ethyl)-1-methylpiperidinium chloride. $^1$H NMR (CD$_3$OD) δ 4.62-4.54 (m, 2 H), 3.81-3.75 ☐m, 2 H), 3.55-3.46 (m, 4 H), 3.18 (s, 3 H), 2.89 (s, 2 H), 2.02-1.89 (m, 4 H), 1.80-1.64 (m, 2 H), 1.51 (s, 6 H); calc. for $C_{13}H_{25}Cl_2N_2O_2^+$: 311.13, Found: 311.0 (M$^+$).

Example 7

2-(Dichloroamino)-N,N-2-trimethyl-N-(2-sulfoethyl)propan-1-ammonium chloride (Compound 21-90)

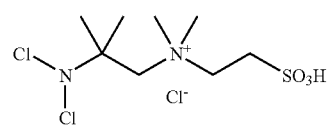

2-(Methyl(2-methyl-2-nitropropyl)amino)ethanol

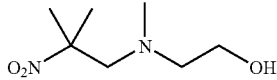

To a stirred solution of 2-nitropropane (20.0 g, 0.22 mol), 2-(methylamino)ethanol (19.7 mL, 1.1 equiv, 0.24 mol) and 5 N NaOH (0.24 mL, 0.005 equiv, 1.2 mmol) in a mixture of isopropanol (34 mL) and water (3.4 mL) was added dropwise a 37% solution of formaldehyde (18.2 mL, 1.1 equiv, 0.24 mol) over 15 min. The reaction was left to stir for 17 h then the solvent was removed in vacuo. 4 M HCl in dioxanes (66 mL, 0.26 mol) was added to the residue and the solvent removed in vacuo to give an oily residue. The oil was triturated with a mixture of isopropanol and anhydrous diethyl ether to give a hygroscopic white powder. The white powder was dissolved into water (100 mL) and 5 N NaOH (35 mL) was added to give a pale yellow green oil. The oil was extracted with DCM (150 mL) and the organic layer washed with water (2×100 mL), dried over anhydrous MgSO₄, filtered and concentrated to a pale yellow green oil (28.0 g, 71.6%). $^1$H NMR (CDCl₃, 400 MHz): δ 1.59 (s, 6H), 2.30 (s, 3H), 2.35-2.38 (t, J=11.2, 1H), 2.63-2.65 (t, J=5.6, 2H), 2.93 (s, 2H), 3.53-3.57 (q, J=5.3, 2H). LRMS (ESI+) for $C_7H_{16}N_2O_3$ (176.1); Found: 177 (MH+).

2-(Methyl(2-methyl-2-nitropropyl)amino ethyl methanesulfonate

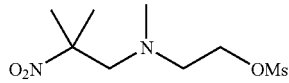

A solution of methanesulfonyl chloride (4.40 mL, 56.7 mmol, 1.0 equiv) in anhydrous DCE (50 mL) was added dropwise over 5 min to an ice cold solution of 2-(methyl(2-methyl-2-nitropropyl)amino)ethanol (10.0 g, 56.7 mmol) and TEA (8.0 mL, 56.7 mmol, 1.0 equiv) dissolved in anhydrous DCE (140 mL, 0.14 M). The ice bath was removed and the reaction stirred at room temperature for 30 min. The suspension was filtered and the filtrate was washed with water (3×50 mL), dried over anhydrous MgSO₄, filtered and concentrated to a viscous yellow oil (12.5 g, 86.7%). This material was used without further purification. LRMS (ESI+) for $C_8H_{18}N_2O_5S$ (254.1); Found: 255 (MH+).

S-2-(Methyl(2-methyl-2-nitropropyl)amino)ethyl ethanethioate

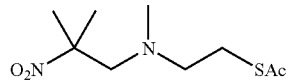

2-(Methyl(2-methyl-2-nitropropyl)amino)ethyl methanesulfonate (12.0 g, 47.2 mmol) was dissolved into anhydrous acetonitrile (200 mL) and solid potassium thioacetate (5.93 g, 1.1 equiv, 51.9 mmol) was added to flask in one portion. The suspension was heated at 50° C. for 4 h. The red slurry was filtered and the solid washed with ethyl acetate (3×150 mL). The filtrate was concentrated to a red brown oil and purified on an ISCO purification system using a 120 g SiO₂ column and the following gradient: isocratic 20% EA in hexanes (5 min) and a gradient to 60% EA in hexanes (15 min). The desired fractions were collected and concentrated to give a red oil (6.83 g, 61.8%). $^1$H NMR (CDCl₃, 400 MHz): δ 1.56 (s, 6H), 2.32 (s, 3H), 2.33 (s, 3H), 2.61-2.65 (m, 2H), 2.89-2.93 (m, 4H). LRMS (ESI+) for $C_9H_{18}N_2O_3S$ (234.1); Found: 235 (MH+).

N-(2-(Acetylthio)ethyl)-N,N-2-trimethyl-2-nitropropan-1-ammonium iodide

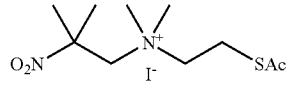

S-2-(Methyl(2-methyl-2-nitropropyl)amino)ethyl ethanethioate (6.83 g, 29.2 mmol), absolute ethanol (4.3 mL, 6.8 M) and methyl iodide (9.1 mL, 5 equiv, 0.15 mol) was added to a 48 mL pressure tube. The reaction was heated in an oil bath at 45° C. for 17 h. The reaction mixture was cooled to room temperature and the suspension was filtered and the solid rinsed with a small amount of ethanol (20 mL) and DCM (50 mL) to give a white solid (3.72 g, 34.0%).

N,N-2-Trimethyl-2-nitro-N-(2-sulfoethyl)propan-1-ammonium chloride

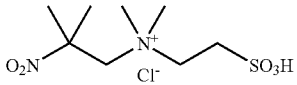

N-(2-(Acetylthio)ethyl)-N,N-2-trimethyl-2-nitropropan-1-ammonium iodide (3.72 g, 9.89 mmol) was dissolved into 88% formic acid (10 mL) and added in one portion to a premixed solution of 88% formic acid (20 mL) and 30% hydrogen peroxide (10 mL). The reaction was exothermic and the temperature rose to 60° C. A water bath was added to cool the reaction to room temperature. Iodine formed during the reaction. The reaction mixture was allowed to stand for 5 min and the supernatant decanted into another flask to leave iodine behind. Additional formic acid (5 mL) was poured into the reaction flask and stirred at room temperature for 17 h. The iodine was destroyed with sodium thiosulfate. The clear colorless solution was concentrated to a pale yellow gum. The gum was dissolved into water (100 mL) and reacted with Ag₂O (1.48 g, 0.65 equiv, 6.42 mmol) to give a red black suspension. The suspension was filtered through Celite® and rinsed with water (50 mL) and the filtrate was acidified with 6 N HCl (15 mL) to give a white precipitate. The solid was filtered through Celite® and the solid rinsed with water (2×50 mL). The filtrate was concentrated to a colorless oil which was purified on a Shimadzu prep-LC using acetonitrile and water with 0.05% acetic acid as modifier. The desired fractions were pooled and concentrated to a gum which was triturated with methanol to give a white solid. The solid was collected and dried under high vacuum to give the desired product (1.17 g, 40.8%). $^1$H NMR (D₂O, 400 MHz): δ 1.88 (s, 6H), 3.23 (s, 6H), 3.49-3.53 (m, 2H), 3.81-3.85 (m, 2H), 4.27 (s, 2H). LRMS (ESI+) for $C_8H_{19}N_2O_5S^+$ (255.1); Found: 255 (M+).

2-Amino-N,N-2-trimethyl-N-(2-sulfoethyl)propan-1-ammonium chloride

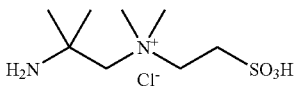

To a 100 mL wide mouth glass bottle was added N,N-2-trimethyl-2-nitro-N-(2-sulfoethyl)propan-1-ammonium chloride (1.07 g, 4.0 mmol), water (10 mL), a magnetic stir bar and Raney nickel (50% aqueous suspension, 0.5 mL). The bottle was placed into a steel pressure vessel, sealed and pressurized with hydrogen (100 psi). The suspension was stirred for 5 min and the hydrogen released until the pressure was just above 0 psi. This was repeated once more and the vessel was finally pressurized to 500 psi. The reaction was stirred at room temperature for 17 h. The hydrogen was released and the suspension was filtered through Celite®. The solid was washed with small portions of water (2×50 mL) and the combined filtrate was concentrated in vacuo to produce a white solid. The solid was dried under high vacuum over P₂O₅ to give the final product as a white powder (0.95 g, quantitative). $^1$H NMR (D₂O, 400 MHz): δ 1.38 (s, 6H), 3.29 (s, 6H), 3.43 (s, 2H), 3.47-3.52 (m, 2H), 3.84-3.88 (m, 2H). LRMS (ESI+) for $C_8H_{21}N_2O_3S^+$ (225.1); Found: 225 (M+).

2-(Dichloroamino)-N,N-2-trimethyl-N-(2-sulfoethyl)propan-1-ammonium chloride

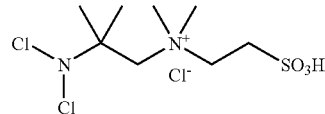

A solution of 2-amino-N,N-2-trimethyl-N-(2-sulfoethyl)propan-1-ammonium chloride (0.31 g, 1.2 mmol) in a mixture of methanol (10 mL) and water (5 mL) was cooled in an ice bath. t-BuOCl (0.34 mL, 2.5 equiv, 22.8 mmol) was added in one portion via syringe to the reaction mixture to give a deep yellow solution. It was stirred for 1 h at 0° C., then concentrated under reduced pressure to yield a white solid. This solid was suspended into DCM (30 mL) and filtered. This was repeated twice more and the solid dried under high vacuum to give a pale yellow solid (0.32 g, 82%). $^1$H NMR ($D_2O$, 400 MHz): δ 1.67 (s, 6H), 3.34 (s, 6H), 3.49-3.53 (m, 2H), 3.81 (s, 2H), 3.87-3.91 (m, 2H). LRMS (ESI+) for $C_8H_{19}Cl_2N_2O_3S^+$ (293.1); Found: 293, 295 (M+, M2H+).

Example 8

N,N-Dibutyl-3-(dichloroamino)-N-3-dimethylbutan-1-aminium chloride Compound (21-48)

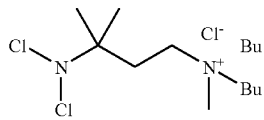

3-Azido-N,N-dibutyl-3-methylbutanamide

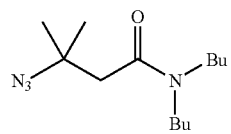

To a stirred ice cold solution of 3-azido-3-methylbutanoyl chloride (10.0 g, 61.8 mmol) in anhydrous DCE (150 mL) was added dibutylamine (21.5 mL, 2 equiv, 0.123 mol) in one portion. A white solid formed immediately and the suspension was stirred vigorously for 3 h at room temperature. DCE (200 mL) and water (200 mL) was added to the reaction mixture and the contents poured into a separatory funnel. The organic layer was separated and washed with water (2×200 mL) and brine (200 mL). It was dried over anhydrous $MgSO_4$, filtered, concentrated and dried under high vacuum to give a crude oil (15.7 g, quantitative). This material was used without further purification. $^1$H NMR ($CDCl_3$, 400 MHz): δ 0.91-0.97 (dt, J=7.2, 7.4, 12H), 1.21-1.38 (m, 4H), 1.46 (s, 6H), 1.47-1.57 (m, 4H), 2.47 (s, 4H), 3.25-3.32 (m, 4H). LRMS (ESI+) for $C_{13}H_{26}N_4O$ (254.2); Found: 255 (MH+)

$N^1,N^1$-Dibutyl-3-methylbutane-1,3-diamine

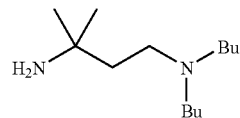

3-Azido-N,N-dibutyl-3-methylbutanamide (16.0 g, 61.8 mmol) was dissolved into anhdrous THF (100 mL, 0.2 M) and added dropwise to a suspension of LAH (4.60 g, 2.0 equiv, 0.124 mol) in anhydrous THF (150 mL) over 25 min. After complete addition, the flask was fitted with a condenser and the reaction heated in a 70° C. oil bath for 8 h. The reaction mixture was removed from the bath and stirred at room temperature for 17 h. The reaction mixture was cooled in an ice bath and water (4.6 mL) was added dropwise over 20 min. Then 15% NaOH solution (4.6 mL) was added dropwise over 10 min. The suspension was stirred for a further 10 min and water (9.0 mL) was added in one portion and the mixture stirred for 30 min to give a fine white suspension. The suspension was filtered through a pad of Celite® and the white cake was washed with isopropanol (3×150 mL) and the combined filtrate was concentrated on a rotovap and briefly dried under high vacuum give a pale yellow liquid (10.2 g, 76.9%). The crude product was used without further purification. LRMS (ESI+) for $C_{13}H_{30}N_2$ (214.2); Found: 215 (MH+).

Benzyl 4-(dibutylamino)-2-methylbutan-2-ylcarbamate

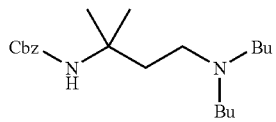

Crude $N^1,N^1$-dibutyl-3-methylbutane-1,3-diamine (10.18 g, 47.4 mmol) was dissolved into THF (237 mL, 0.2 M). To this solution was added CbzOSu (11.8 g, 1 equiv, 47.4 mmol) in one portion. The reaction was left to stir at room temperature for 17 h. The solvent was removed and the residue was taken up in a mixture of ethyl acetate (600 mL) and water (200 mL). The layers were separated and the organic layer washed with water (2×300 mL) and brine (100 mL). The organic layer was dried over anhydrous $MgSO_4$, filtered and concentrated to a pale yellow oil. The crude oil was purified on an ISCO purification system with gradient elution from 60-80% ethyl acetate in hexanes. The desired fractions were collected and concentrated to give a colorless oil (12.6 g, 76.3%). LRMS (ESI+) for $C_{21}H_{36}N_2O_2$ (348.3); Found: 349 (MH+).

3-(Benzyloxycarbonylamino)-N,N-dibutyl-N-3-dimethylbutan-1-ammonium iodide

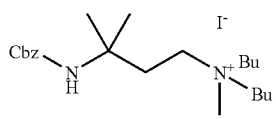

Benzyl 4-(dibutylamino)-2-methylbutan-2-ylcarbamate (6.0 g, 17.2 mmol) was placed into a 15 mL pressure tube. Methanol (2.5 mL, 6.8 M) and methyl iodide (5.4 mL, 5 equiv, 86.0 mmol) was added to the reaction. A stir bar was added and the pressure tube sealed. The reaction was heated in an oil bath at 45° C. for 17 h. The solution was concentrated and dried under high vacuum to give a dark red syrup (8.2 g, quantitative). The material was used without further purification. LRMS (ESI+) for $C_{22}H_{39}N_2O_2^+$ (363.3); Found: 363 (M+).

3-Amino-N,N-dibutyl-N-3-dimethylbutan-1-ammonium chloride hydrochloride

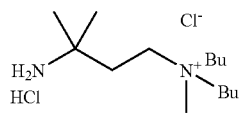

3-(Benzyloxycarbonylamino)-N,N-dibutyl-N-3-dimethylbutan-1-ammonium iodide (8.2 g, 16.7 mmol) was dissolved into a mixture of methanol (75 mL) and water (75 mL). Ag$_2$O (2.51 g, 0.65 equiv, 10.1 mmol) was added in one portion. The black suspension immediately changed to a cream colored suspension. The reaction was stirred at room temperature for 1 h. The red-black solid was filtered through a pad of Celite® and the solid was washed with water (50 mL) and methanol (50 mL). The filtrate was acidified with 6 N HCl to pH 2 and a white suspension formed. The suspension was filtered through Celite® and the solid rinsed with methanol (100 mL). The combined filtrate was concentrated and dried under high vacuum to give pale yellow oil (6.80 g, quantitative). The oil was placed into a flask and dissolved into a mixture of methanol (50 mL) and water (50 mL). The flask was flushed with nitrogen for 5 min and 10% Pd/C (350 mg) was added to the reaction in one portion. The flask was sealed and degassed with vacuum and flushed with hydrogen from a balloon (3 times). The reaction was stirred at room temperature for 17 h. The suspension was filtered through a pad of Celite® and the solid was washed with methanol (50 mL). The filtrate was concentrated and dried under high vacuum over P$_2$O$_5$ to give a pale yellow viscous oil (5.14 g, quantitative). $^1$H NMR (CDCl$_3$, 400 MHz): δ 0.79-0.87 (m, 6 H), 1.2-1.32 (m, 10 H), 1.56-1.62 (m, 4H), 1.94-1.98 (m, 2H), 2.93 (s, 3H), 3.17-3.21 (m, 4H), 3.27-3.32 (m, 2H). LRMS (ESI+) for $C_{14}H_{33}N_2^+$ (229.3); Found: 229 (M+).

N,N-Dibutyl-3-(dichloroamino)-N-3-dimethylbutan-1-ammonium chloride

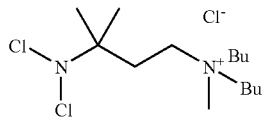

A solution of 3-amino-N,N-dibutyl-N,3-dimethylbutan-1-ammonium chloride hydrochloride (1.15 g, 3.81 mmol) in water (10 mL) was cooled in an ice bath for 15 min. 5% Bleach (14.0 mL, 2.5 equiv, 9.52 mmol) was acidified with 1 N HCl to pH 5 and added in one portion to the colorless solution to give a deep yellow solution. The reaction mixture was stirred at room temperature for 1 h, then concentrated under reduced pressure to give a white solid. This solid was suspended into 2-propanol (10 mL) and the solid filtered and rinsed with 2-propanol (2×10 mL). The combined filtrate was concentrated in vacuo to give a white gummy solid which was purified via reverse phase chromatography on a Shimadzu Prep-LC utilizing water/methanol and 0.05% acetic acid as modifier. Fractions were collected monitoring UV absorbance at 215 nm. Fractions were pooled and lyophilized to give a yellow semi-solid (0.61 g, 47.8%). $^1$H NMR (D$_2$O, 400 MHz): δ 0.94-0.98 (t, J=7.2, 6H), 1.34-1.43 (m, 4H), 1.461 (s, 6H), 1.68-1.77 (m, 4H), 2.18-2.22 (m, 2H), 3.03 (s, 3H), 2.25-3.31 (m, 4H), 3.33-3.43 (m, 2H). LRMS (ESI+) for $C_{14}H_{31}Cl_2N_2^+$ (297.2); Found: 297, 299 (M+, M2H+).

Example 9

1-(2-(dichloroamino)-2-methylpropyl)-1-methylpiperidinium chloride (Compound 21-78)

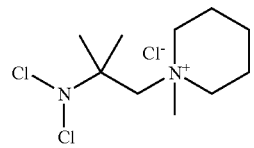

1-(2-Methyl-2-nitropropyl)piperidine

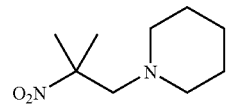

To a stirred ice cold solution of 2-nitropropane (10.0 g, 0.11 mol) and piperidine (11.1 mL, 1 equiv, 0.11 mol) was added dropwise a premixed solution of sodium hydroxide (0.5 mL, 5 N, 2 mol %) and a 37% aqueous solution of formaldehyde (8.4 mL g, 1 equiv, 0.11 mol) over 15 minutes maintaining an internal temperature between 10-15° C. The flask was removed from the ice bath and stirred at room temperature for 1 h. The reaction was then heated at 50° C. for 1 h. The biphasic mixture was cooled to room temperature and poured into a separatory funnel and diluted with ethyl acetate (150 mL) and water (50 mL). The layers were separated and the organic layer was washed with water (2×50 mL) and brine (50 mL). The organic layer was dried over anhydrous MgSO$_4$, filtered and concentrated to a yellow liquid (20.0 g). This material was used without further purification. $^1$H NMR (CDCl$_3$, 400 MHz): δ 1.35-1.38 (m, 2H), 1.46-1.51 (m, 4H), 1.53 (s, 6H), 2.43-2.46 (t, J=5.2, 4H), 3.10 (s, 3H), 3.42-3.51 (m, 4H), 4.20 (s, 2H).

1-Methyl-1-(2-methyl-2-nitropropyl)piperidinium iodide

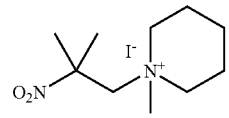

1-(2-Methyl-2-nitropropyl)piperidine (10.8 g, 57.9 mmol) was placed into a 48 mL pressure tube. Absolute ethanol (8.5 mL, 6.8 M) and methyl iodide (18.0 mL, 5 equiv, 0.29 mol) was added to the pressure tube. A stir bar was added and the pressure tube sealed. The reaction was left to stir at room temperature for 3 days. A thick yellow suspension had formed. The suspension was filtered and the solid washed with DCM to give a white powdery solid. The mother liquor was concentrated to deep yellow mushy solid. This solid was washed with DCM to give a white powdery solid. The two solids were combined and dried under high vacuum to give a white powder (10.4 g, 60%). $^1$H NMR (D$_2$O, 400 MHz): δ 1.54-1.64 (m, 1H), 1.72-1.78 (m, 1H), 1.87 (s, 6H), 1.86-2.01

(m, 4H), 3.10 (s, 3 H), 3.42-3.51 (m, 4H), 4.20 (s, 2H). LRMS (ESI+) for $C_{10}H_{21}N_2O_2^+$ (201.2); Found: 201 (M+).

1-(2-Amino-2-methylpropyl)-1-methylpiperidinium chloride hydrochloride

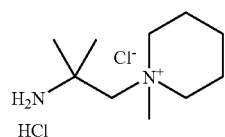

A solution of 1-methyl-1-(2-methyl-2-nitropropyl)piperidinium iodide (5.68 g, 48.8 mmol) in a mixture of methanol and water (25:75 mL) was added to a steel pressure vessel equipped with a magnetic stir bar. The vessel was flushed with nitrogen while Raney nickel (50% aqueous suspension, 2.0 mL) was added in one portion. The vessel was sealed and pressurized with hydrogen (100 psi). The suspension was stirred for 5 min and the hydrogen released until the pressure was just above 0 psi. This was repeated once more and the vessel was finally pressurized to 500 psi. The reaction was stirred at room temperature for 17 h. The hydrogen was released and the suspension was filtered through Celite®. The solid was washed with small portions of water (5×40 mL) to give a colorless filtrate. The filtrate was concentrated in vacuo to a yellow oil. The oil was vigorously stirred overnight with isopropyl alcohol (20 mL), acetonitrile (200 mL) and diethylether (100 mL) to give a tacky white solid. The solid was redissolved into water and Ag$_2$O (0.65 equiv, 18.8 mmol, 4.35 g) was added in one portion. The black suspension was stirred for 30 min at room temperature. The color of the solid gradually changes from black to white then back to grey. The suspension was filtered through Celite® and washed with water (100 mL). The filtrate (~pH 10-11) was acidified with 6 N HCl to ~pH 2. The suspension formed was filtered through Celite® and washed with water (100 mL). The filtrate was concentrated in vacuo to an oil which upon repeated dissolution and concentration from isopropyl alcohol formed a white hygroscopic solid, (6.32 g, 90%). Crude solid was used without further purification. $^1$H NMR (D$_2$O, 400 MHz): δ 1.60-1.65 (m, 1H), 1.74-1.7 (m, 1H), 1.69 (s, 6H), 1.89-2.00 (m, 4H), 3.29 (s, 3 H), 3.49-3.60 (m, 4H), 3.71 (s, 2H). LRMS (ESI+) for $C_{10}H_{23}N_2^+$171.2); Found: 171 (M+).

1-(2-(Dichloroamino)-2-methylpropyl)-1-methylperidinium chloride

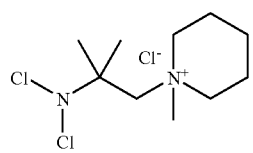

A solution of 2-amino-N,N,N-2-tetramethylpropan-1-ammonium chloride hydrochloride (1.00 g, 4.11 mmol) in a mixture of methanol (12 mL) and water (6 mL) was cooled in an ice bath for 15 min. t-BuOCl (1.45 mL, 3.0 equiv, 12.3 mmol) was added in one portion via syringe to the colorless solution to give a deep yellow solution. The reaction mixture was stirred for 30 min at 0° C. and room temperature for 1 h. The pale yellow solution was concentrated under reduced pressure to yield a pale yellow foam. This solid was dissolved into water and purified via reverse phase chromatography on a Shimadzu Prep-LC utilizing water/methanol and 0.05% acetic acid as modifier. Fractions were collected monitoring UV absorbance at 215 nm. Fractions were pooled and lyophilized to give a white solid, (0.98 g, 86.5%). $^1$H NMR (D$_2$O, 400 MHz): δ 1.52-1.63 (m, 1H), 1.71-1.79 (m, 1H), 1.66 (s, 6H), 1.86-2.01 (m, 4H), 3.2 (s, 3 H), 3.52-3.56 (m, 4H), 3.75 (s, 2H). LRMS (ESI+) for $C_{10}H_{21}Cl_2N_2^+$ (239.10); Found: 239, 241 (M+, M2H+).

Example 10

3-(Dichloroamino)-N,N,N-3-tetramethylbutan-1-ammonium chloride (Compound 21-80)

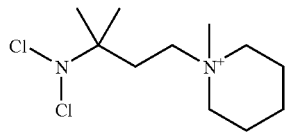

Benzyl 2-methyl-4-oxo-4-(piperidin-1-yl)butan-2-ylcarbamate

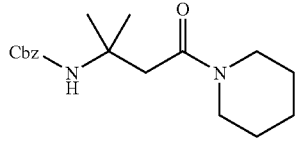

To a stirred solution of 3-(benzyloxycarbonylamino)-3-methylbutanoic acid (11.8 g, 46.8 mmol) in DMF (100 mL) was added CDI (7.60 g, 1 equiv, 46.8 mmol) in one portion and stirred at room temperature for 2 h. Piperidine (9.27 mL, 2 equiv, 93.6 mmol) was added and the reaction was left to stir for 17 h. The solvent was removed on a rotovap and the residue was dissolved into a mixture of ethyl acetate (300 mL) and water (100 mL). The organic layer was separated and washed with saturated NaHCO$_3$ solution (2×150 mL), 1 N HCl solution (150 mL) and brine (150 mL). It was dried over anhydrous MgSO$_4$, filtered and concentrated to an oil. The crude material was purified on an ISCO system using a 220 g column and ethyl acetate and hexanes as eluent. The desired fractions were collected and concentrated to a colorless oil (8.84 g, 60%). $^1$H NMR (CDCl$_3$, 400 MHz): δ 1.45 (s, 6H), 1.48-1.57 (m, 4H), 1.60-1.66 (m, 2H), 3.40-3.44 (m, 2H), 3.52-3.58 (m, 2H), 5.04 (s, 2H), 6.15 (s, 1H), 7.27-7.37 (m, 5H). LRMS (ESI+) for $C_{18}H_{26}N_2O_3$ (318.2); Found: 319 (MH+).

3-Amino-3-methyl-1-(piperidin-1-yl)butan-1-one

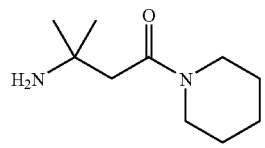

A solution of benzyl 2-methyl-4-oxo-4-(piperidin-1-yebutan-2-ylcarbamate (8.84 g, 27.7 mmol) in methanol (100 mL) was flushed with nitrogen for 5 min and 10% Pd/C (500 mg) was added to the reaction in one portion. The flask was sealed

Benzyl 2-methyl-4-(piperidin-1-yl)butan-2-ylcarbamate and degassed with vacuum and flushed with hydrogen from a balloon (3×). The reaction was stirred at room temperature for 17 h. The suspension was filtered through a pad of Celite® and the solid was washed with methanol (100 mL). The filtrate was concentrated to an oil and dried under vacuum to give a colorless oil (5.11 g, quant). The crude material was used without further purification. $^1$H NMR (CDCl$_3$, 400 MHz): δ 1.22 (s, 6H), 1.50-1.52 (m, 4H), 1.20-1.35 (m, 2H), 2.38 (s, 2H), 3.40-3.43 (m, 2H), 3.53-3.58 (m, 2H). LRMS (ESI+) for C$_{10}$H$_{20}$N$_2$O (184.2); Found: 185 (MH+).

Benzyl 2-methyl-4-(piperidin-1-yl)butan-2-ylcarbamate

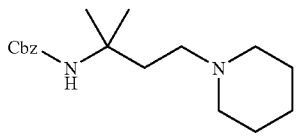

To a suspension of LAH (2.50 g, 2.0 equiv, 65.1 mmol) in anhydrous THF (200 mL) in a 1 L three neck flask fitted with a pressure equalizing dropping funnel and a condenser was added dropwise a solution of 3-amino-3-methyl-1-(piperidin-1-yl)butan-1-one (5.11 g, 27.7 mmol) in anhydrous THF (100 mL, 0.28 M) under an inert atmosphere. The reaction was then heated in a 70° C. oil bath for 9 h. The reaction was then left to reach room temperature and stood without stirring for 8 h. The reaction mixture was cooled in an ice bath and water (2.5 mL) was added dropwise over 20 min. Then 15% NaOH solution (2.5 mL) was added dropwise over 10 min. The suspension was stirred for a further 10 min and water (5.0 mL) was added in one portion followed by anhydrous MgSO$_4$ (50 g) and the mixture stirred for 1 h to give a fine white suspension. The suspension was filtered through a pad of Celite® and the white cake was re-suspended into diethyl ether (200 mL) to give a white granular solid. The suspension was filtered and the cake washed with isopropyl alcohol (3×200 mL) and the combined filtrate was concentrated in vacuo with the bath temperature set to 20° C. to give a pale yellow liquid which was briefly dried under high vacuum to give crude compound (5.56 g, quant).

To a solution of crude 2-methyl-4-(piperidin-1-yl)butan-2-amine in THF (100 mL) was added CbzOSu (8.10 g, 1.2 equiv, 33.2 mmol) in one portion. The reaction mixture was left to stir at room temperature for 17 h. The solvent was removed under reduced pressure and the residue was taken up in a mixture of ethyl acetate (300 mL) and water (100 mL). The layers were separated and the organic layer washed with saturated sodium bicarbonate (2×100 mL), water (100 mL) and brine (100 mL). The organic layer was dried over anhydrous MgSO$_4$, filtered and concentrated to a pale yellow oil. The crude oil was purified on an ISCO purification system with gradient elution from 5% ethyl acetate in hexanes to 100% ethyl acetate. The desired fractions were collected and concentrated to give a pale yellow oil (4.91 g, 49.6%). $^1$H NMR (CDCl$_3$, 400 MHz): δ 1.36 (s, 6H), 1.37-1.45 (m, 2H), 1.51-1.53 (m, 6H), 2.30-2.45 (m, 6H), 2.38 (s, 2H), 5.05 (s, 2H), 7.27-7.36 (m, 5H). LRMS (ESI+) for C$_{18}$H$_{28}$N$_2$O$_2$ (304.2); Found: 305 (MH+).

1-(3-(Benzyloxycarbonylamino)-3-methylbutyl)-1-methylpiperidinium iodide

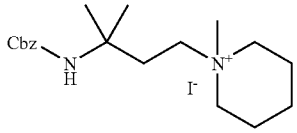

In a 15 mL pressure tube, methyl iodide (2.0 mL, 5 equiv, 31.3 mmol) was added to a stirred solution of benzyl 2-methyl-4-(piperidin-1-yl)butan-2-ylcarbamate (1.91 g, 6.27 mmol) in ethanol (2.0 mL, 3.1 M). The pressure tube was sealed and the reaction was left to stir for 3 days. The yellow solution was poured into a round bottomed flask and the tube rinsed with ethanol. The reaction mixture was concentrated in vacuo to a syrup. Repeated addition and evaporation of isopropyl alcohol (3×10 mL) from the flask followed by acetonitrile (50 mL) gave a white solid. This solid was recrystallized from isopropyl alcohol. The crystals were filtered and rinsed with a small amount of cold isopropyl alcohol and dried under high vacuum to give white crystals, (2.51 g, 89.6%). $^1$H NMR (D$_2$O, 400 MHz): δ 1.30 (s, 6H), 1.43-1.82 (m, 6H), 2.04-2.10 (m, 2H), 2.84 (s, 3H), 3.04-3.24 (m, 6H), 5.08 (s, 2H), 7.38-7.50 (m, 5H). LRMS (ESI+) for C$_{19}$H$_{31}$N$_2$O$_2$$^+$ (319.2); Found: 319 (M+).

1-(3-Amino-3-methylbutyl)-1-methylpiperidinium chloride

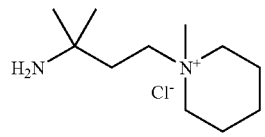

10% Pd/C (500 mg) was added in one portion to a solution of 1-(3-(benzyloxycarbonylamino)-3-methylbutyl)-1-methylpiperidinium iodide (2.00 g, 4.48 mmol) in water (50 mL). The flask was flushed with nitrogen and methanol (50 mL) was added in one portion. The flask was sealed and degassed with vacuum and flushed with hydrogen from a balloon (3×). The reaction was stirred at room temperature for 20 h. The suspension was filtered through a pad of Celite® and the solid was washed with water (2×50 mL) and methanol (2×50 mL). The solution was concentrated to a yellow oil. The crude material was redissolved into water (50 mL) and Ag$_2$O (0.67 g, 0.65 equiv, 2.91 mmol) was added in one portion. The black suspension immediately changed to a cream color suspension and stirred for 30 min. The red-black solid was filtered through a pad of Celite® and the solid was washed with water (50 mL). The filtrate was acidified to ~pH 2 with 6 N HCl to give a white suspension. The suspension was filtered through Celite® and the solid washed with water (50 mL). The filtrate was concentrated under reduced pressure to give yellow oil. (1.15 g, quant). $^1$H NMR (D$_2$O, 400 MHz): δ 1.44 (s, 6H), 1.60-1.77 (m, 2H), 1.89-2.02 (m, 4H), 2.16-2.20 (m, 2H), 3.09 (s, 3H), 3.34-3.42 (m, 4H), 3.48-3.52 (2H). LRMS (ESI+) for C$_{11}$H$_{25}$Cl$_2$N$_2$$^+$ (185.1); Found: 185 (M+).

1-(3-(Dichloroamino)-3-methylbutyl)-1-methylpiperidinium chloride

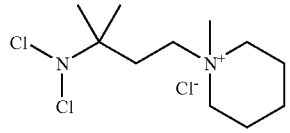

A solution of 1-(3-amino-3-methylbutyl)-1-methylpiperidinium chloride (1.00 g, 3.80 mmol) in a mixture of methanol (6 mL) and water (6 mL) was cooled in an ice bath for 15 min. t-BuOCl (1.3 mL, 3.0 equiv, 11.4 mmol) was added in one portion via syringe to the colorless solution to give a deep yellow solution. The reaction mixture was stirred for 30 min at 0° C. Then the methanol was removed under reduced pressure and the crude solid was purified via reverse phase chromatography on a Shimadzu Prep-LC utilizing water/methanol and 0.05% acetic acid as modifier. Fractions were collected monitoring UV absorbance at 215 nm. Fractions were pooled and concentrated under reduced pressure at 25° C. to give a white solid, (0.92 g, 83%). $^1$H NMR (D$_2$O, 400 MHz): δ 1.46 (s, 6H), 1.52-1.55 (m, 2H), 1.70-1.95 (m, 4H), 2.20-2.28 (m, 2H), 3.05 (s, 3H), 3.35-3.48 (m, 6H). LRMS (ESI+) for $C_{11}H_{23}Cl_2N_2^+$ (253.1); Found: 253, 255 (M+, M2H+).

Example 11

(2-(Dichloroamino)-2-methylpropyl)dimethylsulfonium chloride (Compound 21-86)

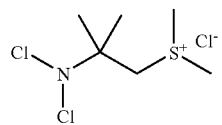

Benzyl 2-methyl-1-(methylthio)propan-2-ylcarbamate

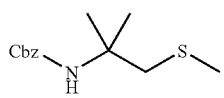

A solution of S-2-(Benzyloxycarbonylamino)-2-methylpropyl ethanethioate (4.75 g, 16.9 mmol) in methanol (35 mL) was mixed with a 5 N sodium hydroxide solution (3 equiv, 50 mL, 50.7 mmol) and stirred at RT for 15 min. TLC (20% ethyl acetate in hexanes) analysis of reaction mixture indicated all the starting material was consumed. The organic solvent was removed under reduced pressure and the resulting aqueous solution was made acidic (~pH 3) with 6 N HCl (9 mL) while cooled in an ice bath. The aqueous suspension was extracted with ethyl acetate (3×100 mL) and the combined organic layer dried over anhydrous MgSO$_4$, filtered and concentrated under reduced pressure to give benzyl 1-mercapto-2-methylpropan-2-ylcarbamate as a pale yellow oil, 4.6 g. This material was used without any further purification.

To a pressure tube was added a solution of benzyl 1-mercapto-2-methylpropan-2-ylcarbamate in methanol (5 mL), TEA (2.35 mL, 1 equiv) and methyl iodide (1.05 mL, 1 equiv). The tube was sealed and the reaction stirred for 17 h. The solvent was removed in vacuo and the crude material was purified on an ISCO purification system. The desired fractions were pooled and concentrated under reduced pressure to give a pale yellow oil (2.78 g, 65%). $^1$H NMR (CDCl$_3$, 400 MHz): δ 1.41 (s, 6H), 2.51 (s, 2H), 2.98 (s, 2 H). LRMS (ESI+) for $C_{13}H_{19}NO_2S$ (253.1); Found: 254 (MH+).

(2-(Benzyloxycarbonylamino)-2-methylpropyl)dimethylsulfonium iodide

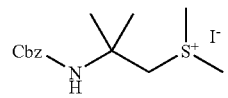

To a 15 mL pressure tube was added a solution of benzyl 2-methyl-1-(methylthio)propan-2-ylcarbamate in absolute ethanol (0.5 mL, 6.8 M) (1.00 g, 3.9 mmol) and methyl iodide (1.23 mL, 5 equiv, 19.7 mmol). The reaction mixture was covered with aluminum foil and left to stir for 3 days. The light yellow suspension was filtered and washed with diethyl ether (20 mL). The mother liquor was concentrated to a deep yellow solid. This solid was recrystallized from isopropyl alcohol and diethyl ether and combined with the first crop of product 1.29 g (83.6%). $^1$H NMR (D$_2$O, 400 MHz): δ 1.41 (s, 6H), 2.51 (s, 2H), 2.98 (s, 2 H). LRMS (ESI−) for $C_{14}H_{22}NO_2S^+$ (268.1); Found: 268 (M+).

(2-Amino-2-methylpropyl)dimethylsulfonium chloride hydrochloride

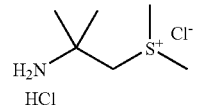

A solution of (2-(benzyloxycarbonylamino)-2-methylpropyl)dimethyl-sulfonium iodide (1.20 g, 3.03 mmol) in a mixture of water (25 mL), methanol (10 mL) and acetic acid (0.4 ml, 2 equiv, 6.06 mmol) was cooled in an ice bath for 5 min, then Ag$_2$O (0.46 g, 0.65 equiv, 1.97 mmol) was added in one portion. The black suspension immediately changed to a cream color suspension and stirred for 30 min. This suspension was filtered through a pad of Celite® and the solid was washed with water (30 mL). The filtrate was acidified to ~pH 2 with 6 N HCl and filtered through Celite® and the residue was washed with water (50 mL). The filtrate was concentrated on a rotovap to give a yellow oil. The crude hydrochloride salt was dissolved into water (20 mL) and 10% Pd/C (300 mg) was added to the reaction in one portion followed by 6 N HCl (1 mL, 2 equiv). The flask was sealed and degassed with vacuum and flushed with hydrogen from a balloon (3×). The reaction was stirred at room temperature for 20 h. The suspension was filtered through a pad of Celite® and the solid was washed with water (2×50 mL). The solution was concentrated in vacuo to a light yellow oil which upon repeated addition and evaporation of isopropyl alcohol (3×10 mL) provided the desired compound (0.62 g, quant). $^1$H NMR (D$_2$O, 400 MHz): δ 1.41 (s, 6H), 2.51 (s, 2H), 2.98 (s, 2 H). LRMS (ESI−) for C$_6$H$_{16}$NS$^+$ (134.1); Found: 134 (M+).

(2-(Dichloroamino)-2-methylpropyl)dimethylsulfonium chloride

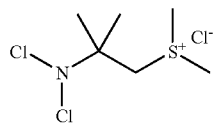

A solution of (2-amino-2-methylpropyl)dimethylsulfonium chloride hydrochloride (0.42 g, 2.0 mmol) in a mixture of methanol (10 mL) and water (10 mL) was cooled in an ice bath for 15 min. t-BuOCl (0.72 mL, 3.0 equiv, 6.1 mmol) was added in one portion via syringe to the colorless solution to give a deep yellow solution. The reaction mixture was stirred for 30 min at 0° C., then room temperature for 30 min. The methanol was removed under reduced pressure and the crude solid was purified via reverse phase chromatography on a Shimadzu Prep-LC utilizing water/methanol and 0.05% acetic acid as modifier. Fractions were collected monitoring UV absorbance at 215 nm. Fractions were pooled frozen and lyophilized to give a white solid, (0.26 g, 53.5%). $^1$H NMR (D$_2$O, 400 MHz): δ 1.41 (s, 6H), 2.51 (s, 2H), 2.98 (s, 2 H). LRMS (ESI−) for C$_6$H$_{14}$Cl$_2$NS$^+$ (202.0); Found: 203, 204 (M+, M2H+).

Example 12

(4-(Dichloroamino)-4-methylpentyl)trimethylphosphonium chloride (Compound 21-106)

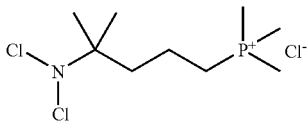

Methyl 4-methyl-4-nitropentanoate

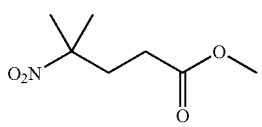

According to the method of R. B. Moffett, *Organic Syntheses*, Coll. Vol. 4, p. 652 (1963), a 250-mL three-necked flask was fitted with a dropping funnel, and a thermometer placed so that the bulb was near the bottom of the flask. A solution of 2-nitropropane (45.5 mL, 0.5 mol) in dioxane (25 mL) and a 40% aqueous solution of benzyltrimethylammonium hydroxide (Triton B, 5 mL, 0.013 mmol) were added to the flask. The flask was heated to 70° C. in an oil bath and methyl acrylate (45 mL, 0.5 mol) was added via a dropping funnel over 15 minutes. The temperature rose to about 100° C. during the addition then dropped to ~85° C. The mixture was then heated at 100° C. for 4 h. The reaction mixture was cooled to room temperature and acidified with 1 N hydrochloric acid (10 mL). Water (200 mL) and diethyl ether (400 mL) were added to the reaction flask. The mixture was poured into a separatory funnel and organic layer was washed with water (2×200 mL), brine (200 mL), dried over anhydrous MgSO$_4$, filtered and concentrated under reduced pressure to give a yellow liquid. The product was distilled through a short path distillation apparatus to give a pale yellow liquid (62.3 g, 71.1%). $^1$H NMR (CDCl$_3$, 400 MHz): δ 1.60 (s, 6H), 2.22-2.38 (m, 4H), 3.70 (s, 3H).

4-Methyl-4-nitropentanol

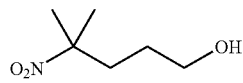

Methyl 4-methyl-4-nitropentanoate (15.5 g, 96.1 mmol) was added to a 1 L round bottomed flask, dissolved into denatured ethanol (300 ml) and cooled in an ice bath for 15 min. Sodium borohydride (7.27 g, 2 equiv, 190 mmol) was added in one portion. Hydrogen was liberated and slowly subsided. The reaction was stirred at 0° C. for 1 h then placed into a 70° C. water bath for 3 h. Water (150 ml) was poured into the flask and 6 N HCl (25 mL) was added dropwise to adjust the pH~3 while cooled in an ice bath. The ethanol was removed under reduced pressure to give a suspension. Water (150 mL) and EA (300 mL) were added to the flask and the mixture poured into a separatory funnel. The layers were separated and the organic layer was washed with brine (100 mL), dried over anhydrous MgSO$_4$, filtered and concentrated on a rotovap to give a pale yellow oil (12.0 g, 85.1%). $^1$H NMR (CDCl$_3$, 400 MHz): ±1.5 (m, 2H), 1.61 (s, 6H), 1.95-2.05 (m, 2H), 3.65 (t, 2H). LRMS (ESI+) for C$_6$H$_{13}$NO$_3$ (147.1); Found: 148 (MH+).

4-Methyl-4-nitropentyl methanesulfonate

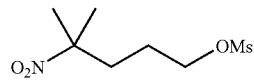

Anhydrous DCM (200 mL) was added via canula to a flask containing 4-methyl-4-nitropentanol (12.0 g, 81.8 mmol) under a nitrogen atmosphere. The solution was cooled in an ice bath for 15 minutes and triethylamine (17.1 mL, 1.5 equiv, 123 mmol) was added followed by the addition of methanesulfonyl chloride (8.23 mL, 1.3 equiv, 106 mmol) via syringe over one min. The mixture was stirred for 1 h at 0° C. Then water (100 mL) was added and the layers were separated. The organic layer was washed with 1 M HCl (100 mL), saturated NaHCO$_3$ solution (100 mL) and brine (100 ml). The organic layer was dried over anhydrous MgSO$_4$, filtered, and concentrated under reduced pressure to give a liquid which crystallized upon addition of a mixture of 20% EA in hexanes (50 mL). The solid was filtered and dried under high vacuum to give a white solid (14.3 g, 78%). $^1$H NMR (CDCl$_3$, 400 MHz): δ 1.61 (s, 6H), 1.73-1.77 (m, 2H), 2.02-206 (m, 2H), 3.02 (s, 3H), 4.23 (t, 2H). LRMS (ESI+) for C$_7$H$_{15}$NO$_5$S (225.1); Found: 226 (MH+).

4-Methyl-4-nitropentyl iodide

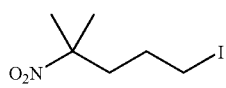

A solution of sodium iodide (17.41 g, 3.9 equiv, 116.6 mmol) in acetone (100 mL, 0.3 M) was added a flask which contained 4-methyl-4-nitropentyl methanesulfonate (6.73 g, 29.9 mmol). The flask was sealed with a septum and covered with aluminum foil and allowed to stir for 17 h. Water (20 ml) was added to the suspension and the acetone was removed by rotovap at reduced pressure. The aqueous solution was extracted with ethyl acetate (150 mL) and washed with 5% aqueous sodium thiosulfate solution (40 ml) and brine (40 ml). The organic layer was dried over anhydrous MgSO$_4$, filtered and concentrated to give a yellow oil (7.46 g, yield 92.0%). $^1$H NMR (CDCl$_3$, 400 MHz): δ 1.60 (s, 6H), 1.78-1.82 (m, 2H), 2.01-2.04 (m, 2H), 3.14-3.18 (t, 2H). LRMS (ESI+) for C$_6$H$_{12}$INO$_2$ (257.0); Found: 258 (MH+).

Trimethyl(4-methyl-4-nitropentyl)phosphonium iodide

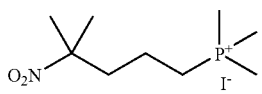

To a 100 mL round bottomed flask was added 4-methyl-4-nitropentyl iodide (2.0 g, 7.78 mmol), 2-butanone (20 mL) and a 1 M solution of trimethylphosphine in THF (15.5 mL, 2 equiv, 15.5 mmol). This flask was placed into a stainless steel pressure vessel, sealed and heated at 100° C. for 4 days. The vessel was cooled and opened in a fumehood. The flask was removed and contained a white solid. The steel vessel contained solvent. The white solid was suspended in ethyl acetate (100 mL), filtered, rinsed with EA (2×50 mL) and dried under high vacuum to give a pale yellow solid (2.39 g, 93%). $^1$H NMR (D$_2$O, 400 MHz): δ 1.62 (s, 6H), 1.84-1.88 (d, J=14.4, 9H), 2.10-2.14 (m, 2H), 2.20-2.28 (m, 2H). LRMS (ESI+) for C$_9$H$_{21}$NO$_2$P$^+$ (206.1); Found: 206 (M+).

(4-Amino-4-methylpentyl)trimethylphosphonium chloride hydrochloride

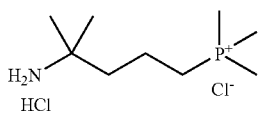

To a 100 mL wide neck bottle was added trimethyl(4-methyl-4-nitropentyl)phosphonium iodide (2.00 g, 6.0 mmol), water (30 mL), a magnetic stir bar and Raney nickel (50% aqueous suspension, 1.0 mL). The bottle was placed into a steel pressure vessel, sealed and pressurized with hydrogen (100 psi). The suspension was stirred for 5 min and the hydrogen released until the pressure was just above 0 psi. This was repeated once more and the vessel was finally pressurized to 500 psi. The reaction was stirred at room temperature for 17 h. The hydrogen was released and the suspension was filtered through Celite®. The solid was washed with small portions of water (2×50 mL) to give a colorless filtrate. Ag$_2$O (0.65 equiv, 3.9 mmol, 0.94 g) was added in one portion to the filtrate. The black suspension was stirred for 30 min at room temperature. The color of the solid gradually changes from black to white then back to grey. The suspension was filtered through Celite® and washed with water (2×50 mL). The filtrate (~pH 10-11) was acidified with 6 N HCl to pH~2 to give a white suspension. The white suspension was filtered through Celite® and washed with water (2×50 mL). The filtrate was concentrated in vacuo to an oil which upon repeated dissolution and concentration from isopropyl alcohol formed a white hygroscopic solid, (1.48 g, quant). The crude solid was used without further purification. $^1$H NMR (D$_2$O, 400 MHz): δ 1.57 (s, 6H), 1.66-1.84 (m, 4H), 1.86-1.89 (d, J=14.4, 9H), 2.22-2.29 (m, 2H). LRMS (ESI+) for C$_9$H$_{23}$NP$^+$ (176.2); Found: 176 (M+).

(4-(Dichloroamino)-4-methylpentyl)trimethylphosphonium chloride

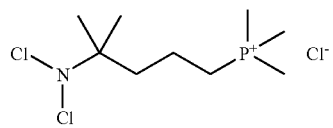

A solution of (4-amino-4-methylpentyl)trimethylphosphonium chloride hydrochloride (0.70 g, 2.82 mmol) in a mixture of methanol (20 mL) and water (10 mL) was cooled in an ice bath for 15 min. t-BuOCl (1.0 mL, 3.0 equiv, 8.5 mmol) was added in one portion via syringe to the colorless solution to give a deep yellow solution. The reaction mixture was stirred for 30 min at 0° C., then room temperature for 30 min. The methanol was removed under reduced pressure and the aqueous solution was purified via reverse phase chromatography on a Shimadzu Prep-LC utilizing water/methanol and 0.05% acetic acid as modifier. Fractions were collected using UV absorbance at 215 nm. Fractions were pooled frozen and lyophilized to give a pale yellow solid (0.654 g, 82.6%). $^1$H NMR (D$_2$O, 400 MHz): δ 1.40 (s, 6H), 1.65-1.69 (m, 2H), 1.85-1.89 (d, J=14.4, 9H), 1.89-1.92 (m, 2H), 2.19-2.27 (m, 2H). LRMS (ESI+) for C$_9$H$_{21}$Cl$_2$NP$^+$ (244.1); Found: 244, 246 (M+, M2H+)

Example 13

(4-(Dichloroamino)-N,N,N-4-tetramethylpentan-1-ammonium chloride (Compound 21-108)

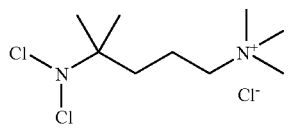

N,N-4-Trimethyl-4-nitropentanamide

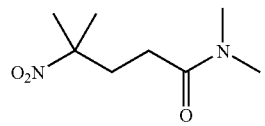

According to the method described in A. Studer et al., *Macromolecules*, 37, 27-34 (2004), a solution of 2-nitropropane (15.2 mL, 168 mmol) in 1,4-dioxane (100 mL) was heated to 70° C. in an oil bath. Triton B (2.3 mL, 13 mmol) and N,N-dimethylacrylamide (14.8 mL, 143 mmol) were each added dropwise to the stirred solution in three portions. The reaction mixture was stirred at 70° C. for 3 h, then cooled to room temperature. 1 N HCl (200 mL) was added to the reaction mixture and the aqueous layer was extracted with CH$_2$Cl$_2$ (3×200 mL). The combined organic layer was washed with brine (100 mL), dried over MgSO$_4$, filtered and concentrated to a pale green liquid (20.6 g, 76.3%). This material was used without further purification. $^1$H NMR (CDCl$_3$, 400 MHz): δ 1.61 (s, 6 H), 2.29 (s, 4 H), 2.95 (s, 3 H), 2.98 (s, 3 H).

N,N,N-4-Tetramethyl-4-nitropentan-1-ammonium iodide

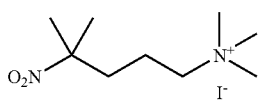

BH$_3$-THF (1 M, 200 mL, 0.2 mmol) was slowly added via canula to a solution of N,N-4-trimethyl-4-nitropentanamide (19.5 g, 0.10 mol) in THF (206 mL, 0.5 M) at room temperature and heated at 70° C. for 4 h. It was cooled and methanol (200 mL) was carefully added to the reaction mixture followed by 4 N HCl in dioxane (100 mL). The mixture was stirred for 3 h, and then the solvent was removed in vacuo. The residue was mixed with saturated K$_2$CO$_3$ (200 mL) and extracted with DCM (4×200 mL). The combined organic extracts were dried over anhydrous MgSO$_4$, filtered and concentrated to an oily residue (14.4, 80.2%). This material was used without further purification.

Methyl iodide (8.0 mL, 5 equiv, 0.13 mol) was added to a stirred ethanol (3.8 mL, 6.8 M) solution of N,N-4-trimethyl-4-nitropentan-1-amine (4.5 g, 25.8 mmol) in a 15 mL pressure tube. The temperature was not allowed to rise above 40° C. The pressure tube was sealed and the reaction was left to stir at room temperature for 3 days. The solution was poured into a round bottomed flask and concentrated to an oil. On standing overnight the oil solidified to a yellow waxy solid (8.16 g, quantitative). This material was used without further purification. $^1$H NMR (D$_2$O, 400 MHz): δ 1.64 (s, 6H), 1.78-1.84 (m, 2H), 1.99-2.03 (m, 2H), 3.13 (s, 9H), 3.33-3.38 (m, 2H). LRMS (ESI+ve) for C$_9$H$_{21}$N$_2$O$_2$$^+$ (189.2); Found: (M+) 189.

4-Amino-N,N,N-4-tetramethylpentan-1-ammonium chloride

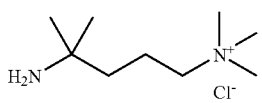

To a 100 mL wide mouth Nalgene bottle was added N,N,N-4-tetramethyl-4-nitropentan-1-ammonium iodide (3.16 g, 10.0 mmol), water (20 mL), a magnetic stir bar and Raney nickel (50% aqueous suspension, 2.0 mL). The bottle was placed into a steel pressure vessel, sealed and pressurized with hydrogen (200 psi). The suspension was stirred for 5 min and the hydrogen released until the pressure was just above 0 psi. This was repeated once more and the vessel was finally pressurized to 400 psi. The reaction was stirred at room temperature for 17 h. The hydrogen was released and the suspension was filtered through Celite®. The solid was washed with small portions of water (2×50 mL) to give a colorless filtrate. Ag$_2$O (1.50 g, 3.9 mmol, 0.65 equiv) was added in one portion to the filtrate. The black suspension was stirred for 30 min at room temperature. The color of the solid gradually changes from black to white then back to grey. The suspension was filtered through Celite® and washed with water (2×50 mL). The filtrate (pH~10-11) was acidified with 6 N HCl to pH~2 to give a white suspension. The white suspension was filtered through Celite® and washed with water (2×50 mL). The filtrate was concentrated in vacuo to an oil which upon repeated dissolution and concentration from isopropyl alcohol formed a white hygroscopic solid, (2.31 g, quantitative). The crude solid was used without further purification. $^1$H NMR (D$_2$O, 400 MHz): δ 1.40 (s, 6 H), 1.69 (t, 2 H, J=8.4 Hz), 1.90 (m, 2H), 3.16 (s, 9H), 3.38 (t, 2 H, J=8.4 Hz). LRMS (ESI+) for C$_9$H$_{23}$N$_2$$^+$ (159.2); Found: (M+) 159.

4-Dichloroamino-N,N,N-4-tetramethylpentan-1-ammonium chloride

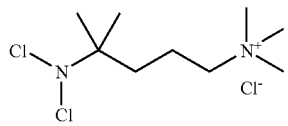

A solution of 4-amino-N,N,N-4-tetramethylpentan-1-ammonium chloride (1.00 g, 4.33 mmol) in methanol (20 mL) was cooled in an ice bath for 15 min. t-BuOCl (1.50 mL, 3.0 equiv, 13.0 mmol) was added in one portion via syringe to the colorless solution to give a deep yellow solution. The reaction mixture was stirred for 30 min at 0° C., then room temperature for 30 min. The methanol was removed under reduced pressure to give a pale yellow solid. This solid was suspended into DCM (20 mL) and filtered. This was repeated twice more and the solid dried under high vacuum to give a pale yellow solid (1.12 g, 98%). $^1$H NMR (D$_2$O, 400 MHz): δ 1.41 (s, 6 H), 1.76-1.87 (m, 4 H), 3.14 (s, 9 H), 3.34 (t, 2H, J=8.2 Hz). LRMS (ESI+) for C$_9$H$_{21}$Cl$_2$N$_2$+ (227.1); Found: (M+) 227.

Example 14

4-Acetyl-1-(2-(dichloroamino)-2-methylpropyl)-1-methylpiperazin-1-ium chloride (Compound 21-110)

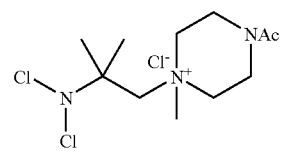

1-(4-(2-Methyl-2-nitropropyl)piperazin-1-yl)ethanone

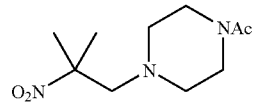

To a stirred ice cold solution of 2-nitropropane (3.5 mL, 38.9 mmol) and N-acetylpiperazine (5.0 g, 1 equiv, 39.6 mmol) was added dropwise a premixed solution of sodium hydroxide (156 μL, 5 N, 2 mol %) and a 37% aqueous solution of formaldehyde (2.9 mL, 1 equiv, 38.9 mmol) over 15 minutes maintaining an internal temperature between 10-15° C. The flask was removed from the ice bath and stirred at room temperature for 1 h. The reaction was then heated at 50° C. for 1 h. The biphasic mixture was cooled to room temperature and poured into a separatory funnel and diluted with ethyl acetate (150 mL) and water (50 mL). The layers were separated and the organic layer was washed with water (2×50 mL) and brine (50 mL). The organic layer was dried over anhydrous MgSO$_4$, filtered and concentrated to a yellow liquid (7.20 g, 81%). This material was used without further purification. $^1$H NMR (CDCl$_3$, 400 MHz): δ 1.57 (s, 6H), 2.06 (s, 3H), 2.50-2.55 (dt, J=5.6, 4H), 2.85 (s, 2H), 3.37-3.40 (t, J=5.0, 2H), 3.54-3.40 (t, J=4.8, 2H).

1-(4-(2-Amino-2-methylpropyl)piperazin-1-yl)ethanone dihydrochloride

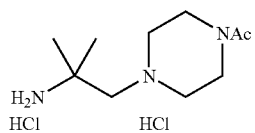

A solution of 1-(4-(2-methyl-2-nitropropyl)piperazin-1-yl)ethanone (7.2 g, 19.4 mmol) in a mixture of methanol and water (50:10 mL) was added to a steel pressure vessel equipped with a magnetic stir bar. The vessel was flushed with nitrogen while Raney nickel (50% aqueous suspension, 1.0 mL) was added in one portion. The vessel was sealed and pressurized with hydrogen (100 psi). The suspension was stirred for 5 min and the hydrogen released until the pressure was just above 0 psi. This was repeated once more and the vessel was finally pressurized to 500 psi. The reaction was stirred at room temperature for 17 h. The hydrogen was released and the suspension was filtered through Celite®. The solid was washed with small portions of water (5×40 mL) to give a colorless filtrate. The filtrate was brought to pH 2 with 6N HCl. The filtrate was concentrated in vacuo to a yellow oil. The oil was purified by Prep-LC utilizing a gradient of methanol and water with 0.05% acetic acid as a modifier. Fractions were pooled and concentrated to give foamy solid (6.91 g, 81%). $^1$H NMR (CDCl$_3$, 400 MHz): δ 1.33 (s, 6H), 2.12 (s, 3H), 2.58 (s, 2H), 2.63-2.72 (dt, J=4.8, 4H), 3.57-3.60 (m, 4H). LRMS (ESI+) for C$_{10}$H$_{21}$N$_3$O (199.1); Found: 200 (MH+).

Benzyl 1-(4-acetylpiperazin-1-yl)-2-methylpropan-2-ylcarbamate (3)

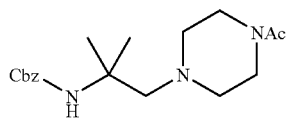

CbzOSu (4.92 g, 1 equiv, 19.7 mmol) and 5 N NaOH (11.8 mL) was added to a solution of 1-(4-(2-mino-2-methylpropyl)piperazin-1-yl)ethanone dihydrochloride (5.37 g, 19.7 mmol) in mixture of isopropanol/water (150:100 mL). The reaction was left to stir at room temperature overnight for 17 h. The solvent was removed and the residue was taken up in a mixture of ethyl acetate (300 mL) and water (100 mL). The layers were separated and the organic layer extracted with water (2×100 mL). The organic layer was dried over anhydrous MgSO$_4$, filtered and concentrated to an oil. The crude oil was purified on an ISCO purification system with gradient elution from 2% methanol in DCM to 30% methanol in DCM. The desired fraction was collected and concentrated to give a colorless oil (2.69 g, yield: 41%). $^1$H NMR (CDCl$_3$, 400 MHz): δ 1.30 (s, 6H), 2.06 (s, 3H), 2.47-2.52 (m, 6H), 3.35-3.38 (m, 2H), 3.52-3.57 (m, 2H), 5.05 (s, 2H), 7.30-7.37 (m, 5H). LRMS (ESI+) for C$_{18}$H$_{27}$N$_3$O$_3$ (333.2); Found: 334 (MH+).

4-Acetyl-1-(2-(benzyloxycarbonylamino)-2-methylpropyl)-1-methylpiperazin-1-ium iodide

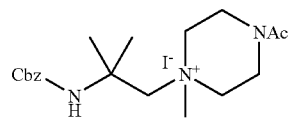

Benzyl 1-(4-acetylpiperazin-1-yl)-2-methylpropan-2-ylcarbamate (2.62 g, 7.86 mmol) was placed into a 15 mL pressure tube. Absolute ethanol (1.1 mL, 7.1 M) and methyl iodide (2.45 mL, 5 equiv, 39.3 mmol) was added to the pressure tube. A stir bar was added and the pressure tube sealed. The reaction was left to stir at room temperature for 7 days. The dark red solution was concentrated to a red oil which became a foam after drying under high vacuum. The foam was purified via Prep-LC using isocratic 95% water and 5% methanol for 5 min followed by a gradient to 95% methanol and 5% water over 16 min. Fraction were pooled to give recovered starting material (0.68 g, 20%) and product as a yellow foam (1.69 g, 45%). $^1$H NMR (D$_2$O, 400 MHz): δ 1.51 (s, 6H), 2.12 (s, 3H), 3.23 (s, 3H), 3.35-3.60 (m, 5H), 3.68-3.85 (m, 4H), 3.92-4.02 (m, 1H), 5.11 (s, 2H), 7.38-7.48 (m, 5H). LRMS (ESI+) for C$_{19}$H$_{30}$N$_3$O$_3$$^+$ (348.2); Found: 348 (M+).

4-Acetyl-1-1-(2-(dichloroamino-2-methylpropyl)-1-methylpiperazin-1-ium chloride

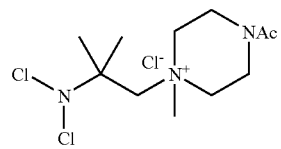

4-Acetyl-1-(2-(benzyloxycarbonylamino)-2-methylpropyl)-1-methylpiperazin-1-ium iodide (1.69 g, 3.6 mmol) was dissolved into 33% HBr in AcOH and left to stir at room temperature for 5 h. The solution was concentrated to an oily red residue. The residue was triturated with diethyl ether (50 mL) and the solid collected by filtration and rinsed with diethyl ether (2×50 mL). The solid was dissolved into water (50 mL) and reacted with Ag$_2$O (0.84 g, 1 equiv) for 30 min. The suspension was filtered through Celite® and the solid washed with water (2×50 mL). The filtrate was made acidic (pH 2) with 6 N HCl to give a white suspension. The suspension was filtered through Celite® and rinsed with water (2×50 mL). The filtrate was concentrated to a yellow residue (1.03 quantitative).

A solution of 4-acetyl-1-(2-amino-2-methylpropyl)-1-methylpiperazin-1-ium chloride hydrochloride (0.68 g, 2.38 mmol) in methanol (15 mL) was cooled in an ice bath for 15 min. t-BuOCl (0.84 mL, 3.0 equiv, 7.13 mmol) was added in one portion via syringe to the colorless solution to give a deep yellow solution. The reaction mixture was stirred for 30 min at 0° C. and room temperature for 1 h. The pale yellow solution was concentrated under reduced pressure to yield a pale yellow solid. This solid was dissolved into water and purified via reverse phase chromatography on a Shimadzu Prep-LC utilizing water/methanol and 0.05% acetic acid as modifier. Fractions were collected monitoring UV absorbance at 215 nm. Fractions were pooled, frozen and lyophilized to give a white solid, (248 mg, 33%). $^1$H NMR (D$_2$O, 400 MHz): δ 1.68 (s, 6H), 2.18 (s, 3H), 3.42 (s, 3H), 3.54-3.78 (m, 5H), 3.86 (s, 2H), 3.88-3.93 (m, 2H), 4.05-4.11 (m, 1H), 4.27-4.35 (m, 1H). LRMS (ESI+) for C$_{11}$H$_{22}$Cl$_2$N$_3$O$^+$ (282.1); Found: 282 (M+).

Example 15

S-3-(3-(Dichloroamino)-3-methylbutylsulfonyl)-N,N,N-trimethylpropan-1-ammonium chloride (Compound 21-112)

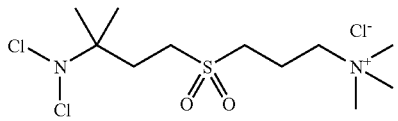

3-(3-(Benzyloxycarbonylamino)-3-methylbutylthio)-N,N,N-trimethylpropan-1-ammonium bromide

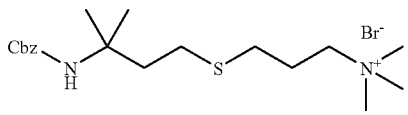

3-(Benzyloxycarbonylamino)-3-methylbutyl ethanethioate (5.00 g, 16.9 mmol, prepared as described in WO 2008/083347) was dissolved into deoxygenated methanol (50 mL) and 5 N Sodium hydroxide solution (3 equiv, 10.1 mL, 50.8 mmol) was added to the solution in one portion to give a slightly exothermic reaction. The reaction was stirred for 15 min and TLC (40% ethyl acetate in hexanes) analysis of reaction mixture indicated all the starting material was consumed. The reaction was made acidic with 6 N HCl (15 mL) then the organic solvent was removed in vacuo and the resulting aqueous suspension was extracted with DCM (3×50 mL). The combined organic layer was dried over anhydrous MgSO$_4$, filtered and concentrated to a pale yellow oil (4.3 g, quant). This material was used without further purification.

The crude benzyl 4-mercapto-2-methylbutan-2-ylcarbamate (4.3 g, 13.4 mmol) from the previous reaction was dissolved into DMF (100 mL). Cesium carbonate (8.25 g, 1.5 equiv, 25.3 mmol) and 3-bromo-N,N,N-trimethylpropan-1-ammonium bromide (4.82 g, 1.1 equiv, 18.6 mmol) was added in one portion to the solution to give a suspension. The suspension was dissolved with water (20 mL). The flask was sealed with a septum, vigorously stirred under a nitrogen atmosphere at 70° C. in an oil bath for 16 h. The reaction was concentrated to an oily solid which was suspended into methanol (100 mL). The suspension was filtered and the solid rinsed with methanol (50 mL). The filtrate was concentrated to an oily residue. This material was purified on an ISCO system through silica gel (120 g) using 5% MeOH in DCM (isocratic) as eluent. Fractions were pooled and concentrated to give a sticky foam (2.33 g, 32%). $^1$H NMR (D$_2$O, 400 MHz): δ 1.26 (s, 6H), 1.92-1.98 (m, 4H), 2.47-2.52 (m, 4H), 3.07 (s, 9 H), 3.31-3.35 (m, 2H), 5.07 (s, 2H), 7.35-7.48 (m, 5H). LRMS (ESI+) for C$_{19}$H$_{33}$N$_2$O$_2$S$^+$ (353.2); Found: 353 (M+).

3-(3-(Benzyloxycarbonylamino)-3-methylbutylsulfonyl)-N,N,N-trimethylpropan-1-ammonium formate

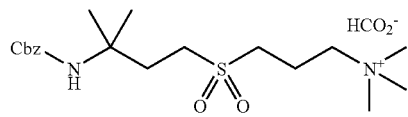

A solution of 3-(3-(benzyloxycarbonylamino)-3-methylbutylthio)-N,N,N-trimethylpropan-1-ammonium bromide (2.33 g, 5.37 mmol) in 88% formic acid (11 mL) was placed into a room temperature water bath and a premixed solution of 88% formic acid (5 mL) and 30% hydrogen peroxide (5 mL) was added in one portion. The reaction was stirred for 5 min and the internal temperature rose to 85° C. The color of solution changed from pale yellow to dark orange upon addition of the oxidant. After the temperature rose to 85° C. the color had changed back to pale yellow. The bromine formed from bromide oxidation was boiled off during the reaction. After the reaction cooled LCMS analysis indicated complete conversion to the product. The solvent was removed to give a thick light brown oil (2.27 g, quant). $^1$H NMR (D$_2$O, 400 MHz): δ 1.30 (s, 6H), 2.16-2.22 (m, 2H), 2.25-2.30 (m, 2H), 2.47-2.52 (m, 4H), 3.15 (s, 9 H), 3.16-3.24 (m, 2H), 3.42-3.47 (m, 2H), 5.08 (s, 2H), 7.38-7.48 (m, 5H), 8.44 (s, 1H). LRMS (ESI+) for C$_{19}$H$_{33}$N$_2$O$_4$S$^+$ (385.2); Found: 385 (M+).

3-(3-Amino-3-methylbutylsulfonyl)-N,N,N-trimethylpropan-1-ammonium chloride hydrochloride

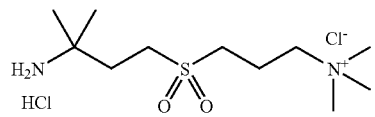

3-(3-(Benzyloxycarbonylamino)-3-methylbutylsulfonyl)-N,N,N-trimethylpropan-1-ammonium formate (1.41 g, 3.5 mmol) was dissolved into methanol (50 mL). The flask was flushed with nitrogen for 5 min, then 10% Pd/C (500 mg) was added to the solution in one portion. The reaction mixture was degassed under vacuum and flushed with hydrogen (3×). The reaction was then stirred under atmospheric pressure with a balloon filled with hydrogen for 3 h. The suspension was filtered through a pad of Celite® wetted with methanol and the solid was rinsed with methanol (2×50 mL). The filtrate was concentrated to give a colorless oil. The oil was reacted with 4 M HCl in dioxanes (4 mL). The solvent was removed to give an oil which solidified on standing in a −20° C. freezer. The solid was suspended into DCM (3×20 mL) and evaporated. The yellow solid was dried under high vacuum to give a yellow powder (1.04 g, quant). This material was used without further purification. $^1$H NMR (D$_2$O, 400 MHz): δ 1.41 (s, 6H), 2.17-2.21 (m, 2H), 2.34-2.42 (m, 2H), 3.15 (s, 9 H), 3.93-3.48 (m, 4H), 3.52-3.56 (m, 2H). LRMS (ESI+) for $C_{11}H_{27}N_2O_2S^+$ (251.2); Found: 251 (M+).

3-(3-(Dichloroamino-3-methylbutylsulfonyl)-N,N,N-trimethylpropan-1-ammonium chloride

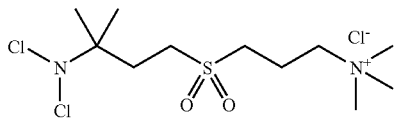

A solution of 3-(3-amino-3-methylbutylsulfonyl)-N,N,N-trimethylpropan-1-ammonium chloride hydrochloride (0.50 g, 1.56 mmol) in a mixture of methanol (15 mL) and water (5 mL) was cooled in an ice bath for 15 min. t-BuOCl (0.55 mL, 3 equiv, 4.64 mmol) was added in one portion via syringe to the colorless solution to give a deep yellow solution. The reaction mixture was stirred for 30 min at 0° C., then concentrated under reduced pressure to yield a pale yellow foam. This solid was repeatedly dissolved into water (3×20 mL) and concentrated to and oil. The oil was dissolved into water (4 mL) and transferred to a vial and the solution lyophilized to a pale yellow solid (0.51 g, quant). $^1$H NMR (D$_2$O, 400 MHz): δ 1.44 (s, 6H), 2.23-2.28 (m, 2H), 2.33-2.42 (m, 2H), 3.19 (s, 9 H), 3.36-3.4 (m, 4H), 3.50-3.55 (m, 2H). LRMS (ESI+) for $C_{11}H_{25}Cl_2N_2O_2S^+$ (319.1); Found: 319 (M+).

Example 16

3-(3-(Dichloroamino)-3-methylbutylsulfonyl)-N,N,N-trimethylpropan-1-ammonium chloride (Compound 21-02)

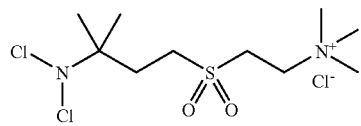

2-(3-(Benzyloxycarbonylamino)-3-methylbutylthio)-N,N,N-trimethylethan ammonium bromide

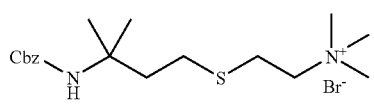

S-3-(Benzyloxycarbonylamino)-3-methylbutyl ethanethioate (2.00 g, 6.8 mmol) (prepared as described in R. Najafi et al., WO 2008/083347) was dissolved in deoxygenated methanol (32 mL) and 5 N Sodium hydroxide solution (3 equiv, 4.1 mL, 20.3 mmol) was added to the solution in one portion to give a slightly exothermic reaction. The reaction was stirred for 15 min and TLC (40% ethyl acetate in hexanes) analysis of reaction mixture indicated all the starting material was consumed. The reaction was made acidic with 6 N HCl (15 mL) then the organic solvent was removed in vacuo and the resulting aqueous suspension was extracted with DCM (3×50 mL). The combined organic layer was dried over anhydrous MgSO$_4$, filtered and concentrated to a pale yellow oil. This material was used without further purification.

The crude benzyl 4-mercapto-2-methylbutan-2-ylcarbamate from the previous reaction was dissolved into DMF (32 mL). DIEA (1.20, 1.0 equiv, 6.8 mmol) and 3-bromo-N,N,N-trimethylpropan-1-ammonium bromide (2.0 g, 1.2 equiv, 8.04 mmol) was added in one portion to the solution to give a suspension. The suspension was dissolved with water (4 mL). The flask was sealed with a septum, vigorously stirred under a nitrogen atmosphere at 70° C. in an oil bath for 2 h. The reaction was concentrated to an oily residue. This material was purified via reverse phase chromatography on a Shimadzu Prep-LC utilizing water/acetonitrile and 0.05% acetic acid as modifier. Fractions were collected using UV absorbance at 215 mm. Fractions were pooled and concentrated by rotovap to give a pale yellow solid (2.14 g, 75.6%). $^1$H NMR (D$_2$O, 400 MHz): δ 1.27 (s, 6H), 1.94-1.99 (m, 2H), 2.52-2.57 (m, 2H), 2.83-2.87 (m, 2H), 3.08 (s, 9 H), 3.42-3.46 (m, 2H), 5.08 (s, 2H), 7.40-7.50 (m, 5H). LRMS (ESI+) for $C_{18}H_{31}N_2O_2S^+$ (339.2); Found: 339 (M+).

2-(3-(Benzyloxycarbonylamino)-3-methylbutylsulfonyl)-N,N,N-trimethylethan ammonium formate

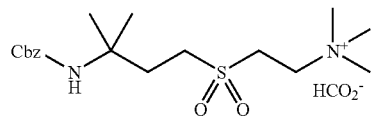

A solution of 2-(3-(benzyloxycarbonylamino)-3-methylbutylthio)-N,N,N-trimethylethan ammonium bromide (2.14 g, 5.10 mmol) in 88% formic acid (11 mL) was placed into a room temperature water bath. Silver(I) oxide (Ag$_2$O, 0.77 g, 0.65 equiv, 3.32 mmol) was added in one portion to the colorless solution to give a white suspension which gradually became darker until it was black after 30 min. A premixed solution of 88% formic acid (5 mL) and 30% hydrogen peroxide (5 mL) was added dropwise over 2 min to the suspension. The reaction was stirred for 2 h at room temperature. LCMS analysis indicated all the starting material had been converted to product. The suspension was filtered through Celite® and concentrated to a grey oily solid. The crude material was suspended into methanol and filtered through a 0.45 µm Teflon cartridge and concentrated to a colorless oil. $^1$H NMR (D$_2$O, 400 MHz): δ 1.31 (s, 6H), 2.21-2.25 (m, 2H), 3.19 (s, 9 H), 3.28-3.32 (m, 2H), 3.77-3.84 (m, 4H), 5.10 (s, 2H), 7.38-7.49 (m, 5H). LRMS (ESI+) for $C_{18}H_{31}N_2O_4S^+$ (371.2); Found: 371 (M+).

2-(3-Amino-3-methylbutylsulfonyl)-N,N,N-trimethylethanammonium chloride hydrochloride

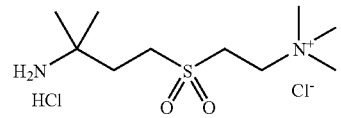

2-(3-(Benzyloxycarbonylamino)-3-methylbutylsulfonyl)-N,N,N-trimethylethan ammonium formate (crude from previous reaction) was mixed with 33% HBr/AcOH (15 mL) and stirred for 17 h. The reaction was concentrated by rotovap to a viscous oil. The oil was triturated with Et$_2$O to give a deep yellow solid. The solid was dissolved into 88% formic acid (40 mL) and Ag$_2$O (1.20 g, 5.10 mmol) was added in one portion to the solution and stirred for 30 min. The suspension was filtered through Celite® and the solid rinsed with 88% formic acid (10 mL). The filtrate was mixed with 6 N HCl (5 mL) and a precipitate formed. The suspension was stirred for 30 min and filtered through a 0.45 μm Teflon cartridge. The filtrate was concentrated to a pale yellow solid (1.10 g, 70%). $^1$H NMR (D$_2$O, 400 MHz): δ 1.42 (s, 6H), 2.20-2.25 (m, 2H), 3.25 (s, 9 H), 3.50-3.55 (m, 2H), 3.96 (s, 4H). LRMS (ESI+) for $C_{10}H_{25}N_2O_2S^+$ (237.2); Found: 237 (M+).

2-(3-(Dichloroamino)-3-methylbutylsulfonyl)-N,N,N-trimethylethanammonium chloride

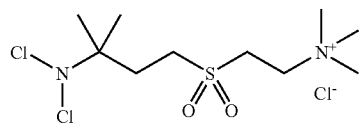

A solution of 2-(3-amino-3-methylbutylsulfonyl)-N,N,N-trimethylethanammonium chloride hydrochloride (0.612 g, 2.0 mmol) in methanol (20 mL) was cooled in an ice bath for 15 min. t-BuOCl (0.55 mL, 3 equiv, 4.64 mmol) was added in one portion via syringe to the colorless solution to give a deep yellow solution. The reaction mixture was stirred for 30 min at 0° C., then concentrated under reduced pressure to yield a pale yellow oil. This oil was dissolved into water and purified via reverse phase chromatography on a Shimdazu Prep-LC utilizing water/acetonitrile and 0.05% acetic acid as modifier. Fractions were collected using UV absorbance at 215 nm. Fractions were pooled frozen and lyophilized to give a pale yellow solid (0.59 g, 87%). $^1$H NMR (D$_2$O, 400 MHz): δ 1.45 (s, 6H), 2.26-2.30 (m, 2H), 3.24 (s, 9 H), 3.43-3.48 (m, 2H), 3.93 (s, 4H). LRMS (ESI+) for $C_{10}H_{23}Cl_2N_2O_2S^+$ (305.1); Found: 305 (M+).

Example 16

3-(Dichloroamino)-N,N-diethyl-N-3-dimethylbutan-1-ammonium chloride (Compound 21-114)

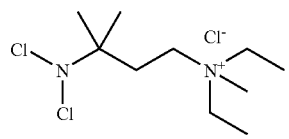

3-Azido-N,N-diethyl-3-methylbutanamide

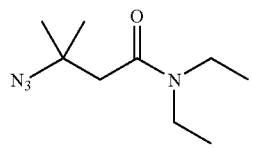

To a stirred ice cold solution of 3-azido-3-methylbutanoyl chloride (8.00 g, 49.5 mmol) in anhydrous DCE (160 mL) was added diethylamine (15.4 mL, 3 equiv, 0.148 mol) in one portion. The reaction was left to stir at 0° C. for 1 h. Water (200 mL) was added to the reaction mixture and the contents poured into a separatory funnel. The organic layer was separated and washed with water (3×100 mL) and brine (100 mL). It was dried over anhydrous MgSO$_4$, filtered, concentrated and dried under high vacuum to give a crude oil (9.80 g, quant). This material was used without further purification.

Benzyl 4-(diethylamino)-2-methylbutan-2-ylcarbamate

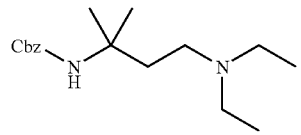

3-Azido-N,N-diethyl-3-methylbutanamide (12.0 g, 60.5 mmol) was dissolved into anhdrous THF (100 mL, 0.2 M) and added dropwise to an ice cold suspension of LAH (4.60 g, 2.0 equiv, 0.12 mol) in anhydrous THF (200 mL) over 30 min. After complete addition, the flask was fitted with a condenser and the reaction heated in a 70° C. oil bath for 6 h. The reaction mixture was cooled in an ice bath and water (4.5 mL) was added dropwise over 20 min. Then 15% NaOH solution (4.5 mL) was added dropwise over 10 min. The suspension was stirred for a further 10 min and water (4.5 mL) was added in one portion and the mixture stirred for 30 min to a give fine white suspension. The suspension was filtered through a pad of Celite® and washed with diethyl ether (3×200 mL). The combined filtrate was carefully concentrated on a rotovap with the bath temperature set to 20° C. to give a pale yellow liquid which was briefly dried under high vacuum to give 7.0 g (yield: 73%,). The crude amine was not dried completely to minimize loss of product due to its low b.p. and used without further purification.

Crude N$^1$,N$^1$-diethyl-3-methylbutane-1,3-diamine (7.00 g, 44.2 mmol) was dissolved into THF (100 mL). To this solution was added CbzOSu (11.0 g, 1 equiv, 44.2 mmol) in one portion. The reaction was left to stir at room temperature for 2 d. The solvent was removed and the residue was taken up in a mixture of ethyl acetate (150 mL) and water (100 mL). The layers were separated and the organic layer washed with saturated sodium bicarbonate (2×100 mL), water (100 mL) and brine (100 mL). The organic layer was dried over anhydrous MgSO$_4$, filtered and concentrated to a pale yellow oil. The crude oil was purified on an ISCO purification system with gradient elution from 1-5% methanol in DCM. The desired fraction was collected and concentrated to give a colorless oil (6.7 g, yield: 37.8%). $^1$H NMR (CDCl$_3$, 400 MHz): δ 1.00-1.04 (t, J=7.0, 6H),1.37 (s, 6H), 1.57-1.61 (t, J=6.2, 2H), 2.45-2.51 (q, J=7.0, 4H), 2.52-2.56 (t, J=6.0, 2 H), 5.04 (s, 2H), 7.27-7.36 (m, 5H), 7.57 (bs, 1H). LRMS (ESI+) for $C_{17}H_{28}N_2O_2$ (292.2); Found: 293 (MH+).

3-(Benzyloxycarbonylamino)-N,N-diethyl-N-3-dimethylbutan-1-ammonium iodide

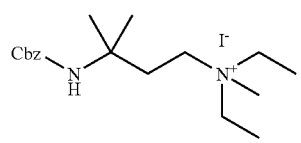

Benzyl 4-(diethylamino)-2-methylbutan-2-ylcarbamate (2.0 g, 6.8 mmol) was placed into a 15 mL pressure tube. Methyl iodide (6.0 mL, 14.6 equiv, 96.8 mmol) was added to the reaction in one portion. Heat evolved and the tube was cooled in a water bath. A stir bar was added and the pressure tube sealed. The reaction was left to stir at 50° C. for 3 d. The solution had become a solid cake. The solid was filtered, rinsed with a small amount of isopropanol (5×10 mL) and dried under high vacuum to give a white crystalline solid (1.65 g, 55%). ¹H NMR (D₂O, 400 MHz): δ 1.16-1.20 (t, J=7.4, 6H),1.29 (s, 3H), 1.30 (s, 3H), 2.05-2.12 (m, 2H), 2.79 (s, 3H), 3.00-3.14 (m, 4H), 3.16-3.22 (q, J=7.2, 2 H), 5.08 (s, 2H), 7.38-7.48 (m, 5H), 7.57 (bs, 1H). LRMS (ESI+) for $C_{18}H_{31}N_2O_2^+$ (307.2); Found: 307 (M+).

3-Amino-N,N-diethyl-N-3-dimethylbutan-1-ammonium chloride hydrochloride

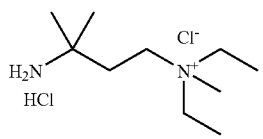

3-(Benzyloxycarbonylamino)-N,N-diethyl-N-3-dimethylbutan-1-ammonium iodide (1.65 g, 3.78 mmol) was dissolved into water (100 mL) and Ag₂O (0.57 g, 0.65 equiv, 2.46 mmol) was added in one portion. The black suspension immediately changed to a cream color suspension. The reaction was stirred at room temperature for 30 min. Aqueous 6 N HCl (5 mL) was added to the flask in one portion to give a white cloudy suspension. The suspension was stirred for 15 min, then filtered through a pad of Celite® and the solid was washed with water (2×30 mL). 10% Pd/C (300 mg) was added to the combined filtrate and the flask sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to a pale blue viscous oil which became a light blue foam after being dried under high vacuum (0.97 g, quant). ¹H NMR (D₂O, 400 MHz): δ 1.31-1.35 (t, J=7.2, 3H), 1.43 (s, 6H), 2.11-2.15 (m, 2H), 3.02 (s, 3 H), 3.37-3.43 (dt, J=7.2, 4H). LRMS (ESI+) for $C_{10}H_{25}N_2^+$ (173.2); Found: 173 (M+).

3-(Dichloroamino)-N,N-diethyl-N-3-dimethylbutan-1-ammonium chloride

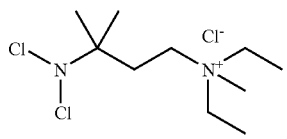

A solution of 3-amino-N,N-diethyl-N-3-dimethylbutan-1-ammonium chloride hydrochloride (0.49 g, 2.0 mmol) in methanol (15 mL) was cooled in an ice bath for 15 min. t-BuOCl (0.72 mL, 3 equiv, 6.0 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a white solid, (0.44 g, 80.2%). ¹H NMR (D₂O, 400 MHz): δ 1.31-1.35 (t, J=7.2, 3H), 1.46 (s, 6H), 2.18-2.22 (m, 2H), 2.99 (s, 3 H), 3.33-3.40 (m, 6H). LRMS (ESI+) for $C_{10}H_{23}Cl_2N_2^+$ (241.1); Found: 241 (M+).

Example 17

1-(3-(Dichloroamino)-3-methylbutyl)-4,4-difluoro-1-methylpiperidinium chloride (Compound 21-116)

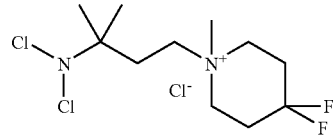

Benzyl 4-(4,4-difluoropiperidin-1-yl)-2-methylbutan-2-ylcarbamate

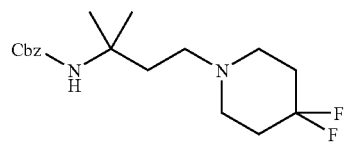

To a stirred ice cold solution of 4,4-difluoropiperidine (5.85 g, 1 equiv, 37.1 mmol) and DIEA (19.9 mL, 3.0 equiv, 0.11 mol) in anhydrous DCE (150 mL) was added 3-azido-3-methylbutanoyl chloride (6.00 g, 37.1 mmol) in small portions. The reaction was stirred and left at 0° C. for 1 h. Aqueous 1 M HCl (100 mL) was added to the reaction mixture and the contents poured into a separatory funnel. The organic layer was separated and washed with 1 M NaHCO₃ (2×100 mL) and brine (100 mL). It was dried over anhydrous MgSO₄, filtered, concentrated and dried under high vacuum to give a crude oil (9.10 g, quant). This material was used without further purification.

3-Azido-1-(4,4-difluoropiperidin-1-yl)-3-methylbutan-1-one (9.10 g, 36.9 mmol) was dissolved into anhydrous THF (50 mL) and added dropwise to a suspension of LAH (2.82 g, 2.0 equiv, 73.9 mmol) in anhydrous THF (50 mL) to maintain the reaction at reflux (30 min). After complete addition, the flask was fitted with a condenser and the reaction heated in a 70° C. oil bath for 6 h. The reaction mixture was cooled in an ice bath and water (3.0 mL) was added dropwise over 20 min. The reaction mixture was cooled in an ice bath and water (3.0 mL) was added dropwise over 20 min. Then 15% NaOH solution (3.0 mL) was added dropwise over 10 min. The suspension was stirred for a further 10 min and water (3.0 mL) was added in one portion and the mixture stirred for 30 min to a give fine white suspension. The suspension was filtered through a pad of Celite® and washed with diethyl ether (3×200 mL). The combined filtrate was carefully concentrated on a rotovap with the bath temperature set to 20° C. to give a pale yellow liquid which was briefly dried under high vacuum to give a liquid (6.56 g, 86.1%). The crude amine was not dried completely to minimize loss of product due to its low b.p. and used without further purification.

Crude 4-(4,4-difluoropiperidin-1-yl)-2-methylbutan-2-amine (6.56 g, 31.8 mmol) was dissolved into THF (100 mL). To this solution was added CbzOSu (7.93 g, 1 equiv, 31.8 mmol) in one portion. The reaction was left to stir at room temperature for 1 d. The solvent was removed and the residue was taken up in a mixture of ethyl acetate (150 mL) and water (100 mL). The layers were separated and the organic layer washed with 1 M sodium carbonate (2×50 mL), 1M HCl (50 mL), and brine (100 mL). The organic layer was dried over anhydrous MgSO$_4$, filtered and concentrated to a colorless oil which solidified on standing. The crude solid was purified on an ISCO purification system with gradient elution from 0-6% methanol. The desired fractions were collected and concentrated to give a white solid (7.54 g, 69.7%). $^1$H NMR (CDCl$_3$, 400 MHz): δ 1.35 (s, 6H), 1.68-1.72 (t, J=6.8, 4H), 1.92-2.05 (m, 4H), 2.16-2.20 (m, 2H), 2.48-2.52 (t, J=6.8, 4H), 2.53-2.58 (m, 4H), 5.04 (s, 2H), 6.70 (s, 1H), 7.27-7.40 (m, 5H). LRMS (ESI+) for C$_{18}$H$_{26}$F$_2$N$_2$O$_2$ (340.1); Found: 341 (MH+).

1-(3-(Benzyloxycarbonylamino)-3-methylbutyl)-4,4-difluoro-1-methylpiperidinium chloride

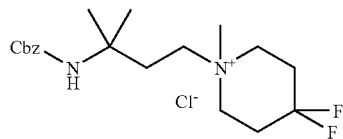

Benzyl 4-(4,4-difluoropiperidin-1-yl)-2-methylbutan-2-ylcarbamate (2.04 g, 5.87 mmol) was placed into a 15 mL pressure tube. Methyl iodide (1.1 mL, 3.0 equiv, 17.6 mmol) was added to the reaction in one portion. Heat evolved and the tube was cooled in a water bath. The reaction was left to stir at 50° C. for 16 h. The solution had become a solid cake. The solid was filtered, rinsed with a small amount of diethyl ether (4×15 mL) and dried under high vacuum to give a white crystalline solid. This solid was immediately dissolved into water (80 mL), then acetic acid (0.5 mL) and Ag$_2$O (1.40 g, 1 equiv, 6.0 mmol). The suspension was stirred for 30 min, then filtered through a pad of Celite® and the solid was washed with water (2×30 mL). The filtrate was acidified with 6 N HCl until the pH was 2. The suspension that formed was stirred for 30 min then filtered through Celite® was washed with water (2×30 mL). The filtrate was concentrated to an oil. (1.76 g, 76.7%). $^1$H NMR (D$_2$O, 400 MHz): δ 1.30 (s, 6H), 2.16-2.25 (m, 2H), 1.92-2.05 (m, 4H), 2.25-2.50 (m, 4H), 2.97 (s, 3H), 3.30-3.38 (m, 2H), 3.40-3.50 (m, 4H), 5.08 (s, 2H), 7.38-7.48 (m, 5H). LRMS (ESI+) for C$_{19}$H$_{29}$F$_2$N$_2$O$_2$$^+$ (355.2); Found: 355 (M+).

1-(3-Amino-3-methylbutyl)-4,4-difluoro-1-methylpiperidinium chloride hydrochloride

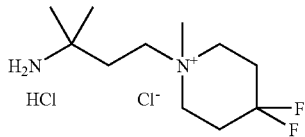

1-(3-(Benzyloxycarbonylamino)-3-methylbutyl)-4,4-difluoro-1-methylpiperidinium chloride (1.78 g, 4.49 mmol) was dissolved into water (100 mL) and 10% Pd/C (300 mg) was added to the flask. It was sealed and degassed with vacuum and flushed with hydrogen from a balloon (3 times). The reaction was stirred at room temperature for 17 h. The suspension was filtered through a pad of Celite® and the solid was washed with water (2×50 mL). The filtrate was concentrated to a viscous oil which became a white foam after being dried under high vacuum (1.30 g, quant). LRMS (ESI+) for C$_{11}$H$_{23}$F$_2$N$_2$$^+$ (221.1); Found: 221 (M+).

1-(3-(Dichloroamino)-3-methylbutyl)-4,4-difluoro-1-methylpiperidinium chloride

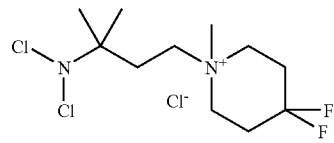

A solution of 1-(3-Amino-3-methylbutyl)-4,4-difluoro-1-methylpiperidinium chloride hydrochloride (0.57 g, 1.94 mmol) in methanol (15 mL) was cooled in an ice bath for 15 min. t-BuOCl (0.69 mL, 3 equiv, 5.82 mmol) was added in one portion via syringe to the colorless solution to give a deep yellow solution. The reaction mixture was stirred for 30 min at 0° C., and then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a white solid, (0.52 g, 83.1%). $^1$H NMR (D$_2$O, 400 MHz): δ 1.47 (s, 6H), 2.27-2.32 (m, 2H), 2.422-2.56 (m, 4H), 3.10 (s, 3H), 3.55-3.61 (m, 2H), 3.65-3.69 (m, 4H). LRMS (ESI+) for C$_{11}$H$_{21}$Cl$_2$F$_2$N2$^+$ (289.1); Found: 289 (M+).

Example 18

1-(3-(Dichloroamino)-3-methylbutyl)-1-methylazepanium chloride (Compound 21-118)

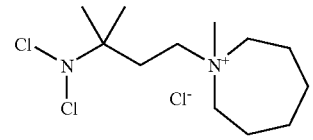

1-(Azepan-1-yl)-3-azido-3-methylbutan-1-one

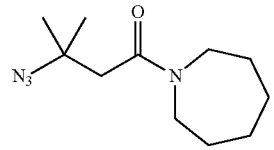

To a stirred ice cold solution of 3-azido-3-methylbutanoyl chloride (8.00 g, 49.5 mmol) in anhydrous DCE (160 mL) was added azepane (12.6 mL, 3 equiv, 0.11 mol) in one portion. The reaction was stirred and left at 0° C. for 15 min and room temperature for 45 min. Aqueous 1 M HCl (100 mL) was added to the reaction mixture and the contents poured into a separatory funnel. The organic layer was separated and washed with 1 M HCl (100 mL) and saturated NaHCO$_3$ (150 mL). It was dried over anhydrous MgSO$_4$, filtered, concentrated and dried under high vacuum to give a crude oil (8.24 g, quant). This material was used without further purification. LRMS (ESI+) for C$_{11}$H$_{20}$N$_4$O (224.1); Found: 225 (MH+).

Benzyl 4-(azepan-1-yl)-2-methylbutan-2-ylcarbamate

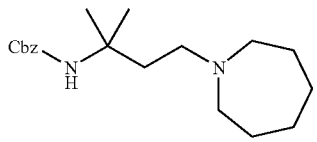

1-(Azepan-1-yl)-3-azido-3-methylbutan-1-one (6.76 g, 36.7 mmol) was dissolved into anhydrous THF (50 mL) and added dropwise to a suspension of LAH (2.82 g, 2.0 equiv, 73.4 mmol) in anhydrous THF (50 mL) to maintain the reaction at reflux (30 min). After complete addition, the flask was fitted with a condenser and the reaction heated in a 70° C. oil bath for 6 h. The reaction mixture was cooled in an ice bath and water (2.80 mL) was added dropwise over 20 min. The reaction mixture was cooled in an ice bath and water (2.80 mL) was added dropwise over 20 min. Then 15% NaOH solution (2.80 mL) was added dropwise over 10 min. The suspension was stirred for a further 10 min and water (3.5 mL) was added in one portion and the mixture stirred for 30 min to a give fine white suspension. The suspension was filtered through a pad of Celite® and washed with diethyl ether (3×200 mL). The combined filtrate was carefully concentrated on a rotovap with the bath temperature set to 20° C. to give a pale yellow liquid which was briefly dried under high vacuum to give a liquid (4.54 g, 67.0%). The crude amine was not dried completely to minimize loss of product due to its low b.p. and used without further purification.

Crude 4-(Azepan-1-yl)-2-methylbutan-2-amine (4.54 g, 24.6 mmol) was dissolved into DCM (120 mL). To this solution was added CbzOSu (6.13 g, 1 equiv, 24.6 mmol) in one portion. The reaction was left to stir at room temperature for 2 d. The solvent was removed and the residue was taken up in a mixture of ethyl acetate (150 mL) and water (100 mL). The layers were separated and the organic layer washed with saturated sodium bicarbonate (2×100 mL), water (100 mL) and brine (100 mL). The organic layer was dried over anhydrous MgSO$_4$, filtered and concentrated to a pale yellow oil (8.33 g). The crude oil was purified on an ISCO purification system with gradient elution from 1-5% methanol in DCM. The desired fraction was collected and concentrated to give a colorless oil (3.69 g, yield: 47.1%). LRMS (ESI+) for $C_{19}H_{30}N_2O_2$ (318.2); Found: 319 (MH+).

1-(3-(Benzyloxycarbonylamino)-3-methylbutyl)-1-methylazepanium chloride

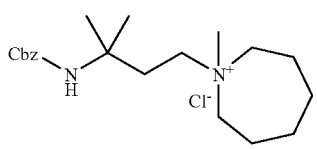

Benzyl 4-(azepan-1-yl)-2-methylbutan-2-ylcarbamate (1.99 g, 6.23 mmol) was placed into a 15 mL pressure tube. Methyl iodide (2.0 mL, 5 equiv, 31.3 mmol) was added to the reaction in one portion. Heat evolved and the tube was cooled in a water bath. A stir bar was added and the pressure tube sealed. The reaction was left to stir at 50° C. for 3 d. The solution had become a solid cake. The solid was filtered, rinsed with a small amount of diethyl ether (4×15 mL) and dried under high vacuum to give a white crystalline solid (1.65 g, 55%). This solid was immediately dissolved into water (80 mL), then acetic acid (0.5 mL) and Ag$_2$O (1.40 g, 1 equiv, 6.0 mmol). The suspension was stirred for 30 min, then filtered through a pad of Celite® and the solid was washed with water (2×30 mL). The filtrate was acidified with 6 N HCl until the pH was 2. The suspension that formed was stirred for 30 min then filtered through Celite® was washed with water (2×30 mL). The filtrate was concentrated to an oil. (1.21 g, 52.6%). $^1$H NMR (D$_2$O, 400 MHz): δ 1.29 (s, 6H), 1.53-1.80 (m, 8H), 2.12-2.20 (m, 2H), 2.83 (s, 3H), 3.15-3.35 m, 6H), 5.08 (s, 2H), 7.40-7.48 (m, 5H). LRMS (ESI+) for $C_{20}H_{33}N_2O_2^+$ (333.2); Found: 333 (M+).

1-3-Amino-3-methylbutyl)-1-meth laze anium chloride hydrochloride

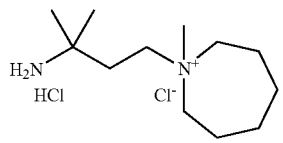

1-(3-(Benzyloxycarbonylamino)-3-methylbutyl)-1-methylazepanium chloride (1.21 g, 3.28 mmol) was dissolved into water (100 mL) and 10% Pd/C (300 mg) was added to the flask. It was sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to a viscous oil which became a white foam after being dried under high vacuum (0.55 g, 62.2%). $^1$H NMR (D$_2$O, 400 MHz): δ 1.43 (s, 6H), 1.67-1.72 (m, 4H), 1.87-1.95 (m, 4H), 2.16-2.20 (m, 2H), 3.06 (s, 3H), 3.41-3.55 (m, 6H). LRMS (ESI+) for $C_{12}H_{27}N_2^+$ (199.2); Found: 199 (M+).

1-3-Dichloroamino-3-1-methyllazepanium chloride

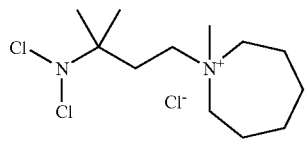

A solution of 1-(3-amino-3-methylbutyl)-1-methylazepanium chloride hydrochloride (0.35 g, 1.48 mmol) in methanol (20 mL) was cooled in an ice bath for 15 min. t-BuOCl (0.52 mL, 3 equiv, 4.42 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a white solid, (0.32 g, 80.0%). $^1$H NMR (D$_2$O, 400 MHz): δ 1.45 (s, 6H), 1.66-1.74 (m, 4H), 1.85-1.95 (m, 4H), 2.22-2.28 (m, 2H), 3.03 (s, 3H), 3.38-3.53 (m, 6H). LRMS (ESI+) for $C_{12}H_{25}Cl_2N_2^+$ (267.1); Found: 267 (M+).

Example 19

1-(3-(Dichloroamino)-3-methylbutyl)-1-azoniabicyclo[2.2.2]octane methanesulfonate (Compound 21-120)

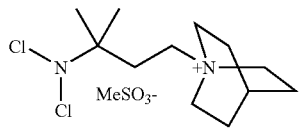

3-Azido-3-methylbutan-1-ol

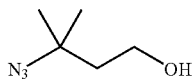

Borane dimethylsulfide complex (2 M, 15 mL, 30 mmol) was added over 20 min to 3-azido-3-methylbutanoic acid (4.25 g, 30 mmol) in THF (15 mL) at room temperature. The reaction was stirred for 16 h. The reaction mixture was cooled in an ice bath and methanol (50 mL) was added dropwise to the solution over 15 min. Then 4 M HCl in dioxanes (7.5 mL, 30 mmol) was added to the reaction mixture and stirred for 30 min. The reaction mixture was concentrated on a rotovap to a colorless liquid (3.33 g, 91%). This material was used without further purification. $^1$H NMR (CDCl$_3$, 400 MHz): δ 1.35 (s, 6H), 1.74-1.78 (t, J=6.4, 2H), 3.75-3.80 (t, J=6.4, 2H). LRMS (ESI+) for $C_5H_{11}N_3O$ (129.1); Found: did not ionize.

3-Azido-3-methylbutyl methanesulfonate

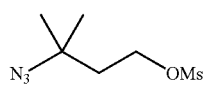

To a stirred ice cold solution of 3-azido-3-methylbutan-1-ol (3.33 g, 25.8 mmol) and DIEA (9.0 mL, 2 equiv, 51.6 mmol) in anhydrous DCM (200 mL) was added methanesulfonyl chloride (2.99 mL, 1.5 equiv, 38.7 mmol) over 5 min. The reaction was stirred and left at 0° C. for 1.5 h. The reaction mixture was extracted with 1 N HCl (2×200 mL), saturated NaHCO$_3$ (2×200 mL) and brine (200 mL). The organic layer was dried over anhydrous MgSO$_4$, filtered, and concentrated to give a colorless liquid. The crude oil was purified on an ISCO purification system with gradient elution from 5-40% ethyl acetate in hexanes. The desired fractions were collected and concentrated to give a colorless liquid (4.45 g, 83.4). $^1$H NMR (CDCl$_3$, 400 MHz): δ 1.36 (s, 6H), 1.93-1.98 (t, J=6.8, 2H), 3.32-4.36 (t, J=6.8, 2H).

1-(3-Azido-3-methylbutyl)-1-azoniabicyclo[2.2.2]octane methanesulfonate

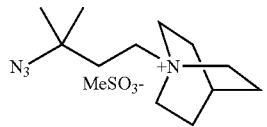

In a 1 dram vial, a solution of 3-azido-3-methylbutyl methanesulfonate (0.45 g, 2.19 mmol) and quinuclidine (0.21 g, 1.9 mmol) in 2-pentanone (2.0 mL) was heated on a heat block at 110° C. for 16 h. The suspension was cooled, filtered, and rinsed with diethyl ether (50 mL). The filtrate was discarded and the solid was dried under high vacuum to give a white solid. (052 g, 74.7%). $^1$H NMR (D$_2$O, 400 MHz): δ 1.35 (s, 6H), 1.95-2.05 (m, 8H), 2.18-2.22 (pent, J=3.6, 1H), 2.82 (s, 3H), 3.24-3.30 (m, 2H), 3.38-3.45 (m, 6H). LRMS (ESI+) for $C_{12}H_{23}N_4^+$(223.2); Found: 223 (M+).

1-(3-Amino-3-methylbutyl)-1-azoniabicyclo[2.2.2]octane methanesulfonate hydrochloride

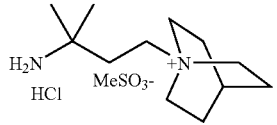

1-(3-Azido-3-methylbutyl)-1-azoniabicyclo[2.2.2]octane methanesulfonate (0.52 g, 1.48 mml) was dissolved into a mixture of methanol (10 mL) and water (10 mL). The flask was flushed with nitrogen for 5 min, then 10% Pd/C (100 mg) was added to the flask which was sealed and degassed with vacuum and flushed with hydrogen from a balloon (3 times). The reaction was stirred at room temperature for 17 h. The suspension was filtered through a pad of Celite® and the solid was washed with water (2×50 mL). The filtrate was concentrated to a viscous oil which became a white foam after being dried under high vacuum (0.63 g, quant). $^1$H NMR (D$_2$O, 400 MHz): δ 1.39 (s, 6H), 1.97-2.02 (m, 6H), 2.09-2.13 (m, 2H), 2.18-2.21 (pent, J=3.2, 1H), 2.80 (s, 3H), 3.26-3.31 (m, 2H), 3.40-3.46 (m, 6H). LRMS (ESI+) for $C_{12}H_{25}N_2^+$(197.2); Found: 197 (M+).

1-(3-(Dichloroamino)-3-methylbutyl)-1-azoniabicyclo[2.2.2]octane methanesulfonate

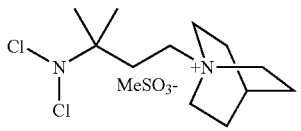

A solution of 1-(3-amino-3-methylbutyl)-1-azoniabicyclo[2.2.2]octane methanesulfonate hydrochloride (0.31 g, 1.2 mmol) in methanol (4.5 mL) was cooled in an ice bath for 15 min. t-BuOCl (0.41 mL, 3 equiv, 3.48 mmol) was added in one portion via syringe to the colorless solution to give a deep yellow solution. The reaction mixture was stirred for 30 min at 0° C., and then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a white solid, (0.21 g, 58.9%). $^1$H NMR (D$_2$O, 400 MHz): δ 1.43 (s, 6H), 1.96-2.03 (m, 6H), 2.16-2.25 (m, 3H), 2.82 (s, 3 H), 3.21-3.29 (m, 2H), 3.40-3.46 (m, 6H). LRMS (ESI+) for C$_{12}$H$_{23}$Cl$_2$N$_2$$^+$ (265.1); Found: 265, 267 (M+, M2H+).

Example 20

1-(3-(Dichloroamino)-3-methylbutyl)-1,4,4-trimethylpiperidinium chloride (Compound 21-122)

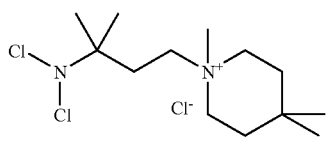

3-Azido-1-(4,4-dimethylpiperidin-1-yl)-3-methylbutan-1-one

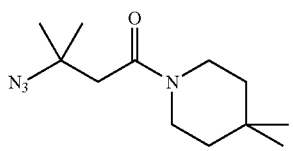

To a stirred ice cold solution of 4,4-dimethylpiperidine (4.21 g, 1 equiv, 37.2 mmol) and DIEA (9.73 mL, 1.5 equiv, 55.9 mmol) in anhydrous DCE (65 mL) was added 3-azido-3-methylbutanoyl chloride (6.02 g, 37.2 mmol) in small portions. The reaction was stirred and left at 0° C. for 1 h. Aqueous 1 M HCl (100 mL) was added to the reaction mixture and the contents poured into a separatory funnel. The organic layer was separated and washed with 1 M HCl (100 mL). It was dried over anhydrous MgSO$_4$, filtered, concentrated and dried under high vacuum to give a crude oil (7.72 g, 87.1%). The crude oil was purified on an ISCO purification system with gradient elution from 20-50% ethyl acetate in hexanes. The desired fractions were collected and concentrated to give a colorless oil (6.00 g, yield: 67.7%). $^1$H NMR (CDCl$_3$, 400 MHz): δ 0.98 (s, 6H), 1.32-1.39 (m, 4H), 1.45 (s, 6H), 2.52 (s, 2H), 3.42-3.47 (m, 2H), 3.55-3.60 (m, 2H). LRMS (ESI+) for C$_{12}$H$_{22}$N$_4$O (238.2); Found: 239 (M+).

Benzyl 4-(4,4-dimethylpiperidin-1-yl)-2-methylbutan-2-ylcarbamate

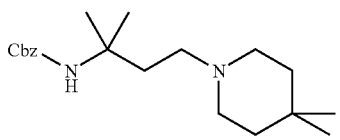

3-Azido-1-(4,4-dimethylpiperidin-1-yl)-3-methylbutan-1-one (5.5 g, 23.1 mmol) was dissolved into anhydrous THF (50 mL) and added dropwise to a suspension of LAH (1.75 g, 2.0 equiv, 46.2 mmol) in anhydrous THF (100 mL) to maintain the reaction at reflux (30 min). After complete addition, the flask was fitted with a condenser and the reaction heated in a 70° C. oil bath for 8 h. The reaction mixture was cooled in an ice bath and water (3.5 mL) was added dropwise over 20 min. Then 15% NaOH solution (1.75 mL) was added dropwise over 10 min. The suspension was stirred for a further 10 min and water (3.5 mL) was added in one portion and the mixture stirred for 30 min to a give fine white suspension. The suspension was filtered through a pad of Celite® and washed with isopropanol (2×75 mL). The combined filtrate was carefully concentrated on a rotovap with the bath temperature set to 20° C. to give a pale yellow liquid which was briefly dried under high vacuum to give a liquid (5.86 g, quant). The crude amine was not dried completely to minimize loss of product due to its low B.P. and used without further purification.

Crude 4-(4,4-dimethylpiperidin-1-yl)-2-methylbutan-2-amine (5.80 g, 29.2 mmol) was dissolved into THF (100 mL). To this solution was added CbzOSu (7.29 g, 1 equiv, 29.2 mmol) in one portion. The reaction was left to stir at room temperature for 3 d. The solvent was removed and the residue was taken up in a mixture of diethyl ether (150 mL) and water (50 mL). The layers were separated and the organic layer washed with 1 M sodium carbonate (2×50 mL), 1M HCl (50 mL), and brine (100 mL). The organic layer was dried over anhydrous MgSO$_4$, filtered and concentrated to a pale yellow oil. The crude oil was purified on an ISCO purification system with gradient elution from 10-80% ethyl acetate in hexanes. The desired fractions were collected and concentrated to give a white solid (4.75 g, yield: 49.0%). $^1$H NMR (CDCl$_3$, 400 MHz): δ 0.92 (s, 6H), 1.35-1.40 (bm, 10H), 1.58-1.63 (t, J=10.8, 2 H), 2.40 (bs, 4H), 2.44-2.52 (t, J=10.8, 2H), 5.03 (s, 2H), 7.27-38 (m, 5H). LRMS (ESI+) for C$_{20}$H$_{32}$N$_2$O$_2$ (332.2); Found: 333 (MH+).

1-(3-(Benzyloxycarbonylamino)-3-methylbutyl)-1,4,4-trimethylpiperidinium iodide

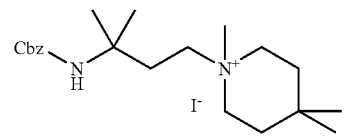

Benzyl 4-(4,4-dimethylpiperidin-1-yl)-2-methylbutan-2-ylcarbamate (2.25 g, 6.76 mmol) was placed into a 15 mL pressure tube. Absolute ethanol (2 mL) and Methyl iodide (5.0 mL, 11.8 equiv, 80.1 mmol) was added in one portion. A stir bar was added and the pressure tube sealed. The reaction was left to stir at 50° C. for 16 h. The solution was concentrated to a pale yellow solid. The crude solid was dissolved into isopropanol (5 mL) and ethyl acetate (25 mL) and the solution cooled in an ice bath to give a gel. The product was filtered, washed with fresh ethyl acetate and dried under high vacuum to give a white solid (2.06 g, 64.0%). $^1$H NMR (D$_2$O, 400 MHz): δ 0.98 (s, 3H), 1.03 (s, 3H), 1.30 (s, 6H), 1.50-1.70 (m, 4 H), 2.10-2.18 (m, 2H), 2.85 (s, 3H), 3.15-3.28 (m, 6 H), 5.09 (s, 2H), 7.38-7.50 (m, 5H). LRMS (ESI+) for C$_{21}$H$_{35}$N$_2$O$_2$$^+$ (347.3); Found: 347 (M+).

3-Amino-3-methylbutyl)-1,4,4-trimethylpiperidinium chloride hydrochloride

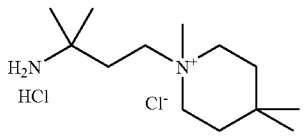

Ag$_2$O (0.57 g, 0.65 equiv, 2.46 mmol) was added in one portion to a solution of 1-(3-(benzyloxycarbonylamino)-3-methylbutyl)-1,4,4-trimethylpiperidinium iodide (1.81 g, 3.81 mmol) in a mixture of methanol (100 mL), water (200 mL) and acetic acid (0.68 mL). The black suspension immediately changed to a cream color suspension. The reaction was stirred at room temperature for 30 min. Aqueous 6 N HCl (2.5 mL) was added to the flask in one portion to give a white cloudy suspension. The suspension was stirred for 15 min, then filtered through a pad of Celite® and the solid was washed with water (2×30 mL). 10% Pd/C (300 mg) was added to the combined filtrate. The flask was sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to an oil which was dissolved into methanol (25 mL) and filtered through a 0.45 micron PTFE frit. The filtrate was concentrated to an oil, dried under high vacuum to give a foam (1.12 g, quant). $^1$H NMR (D$_2$O, 400 MHz): δ 1.05 (s, 3H), 1.06 (s, 3H), 1.42 (s, 6H), 1.63-1.83 (m, 4H), 2.15-2.21 (m, 2H), 3.07 (s, 3 H), 3.38-3.43 (m, 4H), 3.46-3.52 (m, 2H). LRMS (ESI+) for C$_{13}$H$_{29}$N$_2$$^+$ (213.2); Found: 213 (M+).

1-(3-(Dichloroamino)-3-methylbutyl)-1,4,4-trimethylpiperidinium chloride

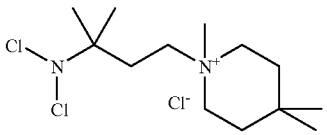

A solution of 1-(3-amino-3-methylbutyl)-1,4,4-trimethylpiperidinium chloride hydrochloride (0.50 g, 1.73 mmol) in a mixture of methanol (10 mL) and water (8 mL) was cooled in an ice bath for 15 min. t-BuOCl (0.62 mL, 3 equiv, 5.21 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a pale yellow foam, (0.373 g, 67.8%). $^1$H NMR (D$_2$O, 400 MHz): δ 1.06 (s, 3H), 1.07 (s, 3H), 1.46 (s, 6H), 1.64-1.80 (m, 4H), 2.21-2.27 (m, 2H), 3.05 (s, 3 H), 3.35-3.45 (m, 6H). LRMS (ESI+) for C$_{13}$H$_{27}$Cl$_2$N$_2$$^+$ (281.1); Found: 281, 283 (M+, M2H+).

Example 21

N-Butyl-3-(dichloroamino)-N,N,3-trimethylbutan-1-ammonium chloride (Compound 21-124)

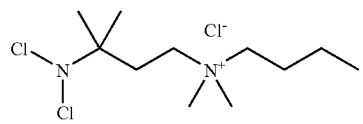

3-Azido-N-butyl-N,3-dimethylbutanamide

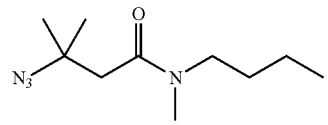

To a stirred ice cold solution of N-methylbutan-1-amine (8.88 mL, 2 equiv, 74.4 mmol) in anhydrous DCE (65 mL) was added 3-azido-3-methylbutanoyl chloride (6.02 g, 37.2 mmol) in small portions over 5 min. The reaction was removed from the ice bath and stirred at room temperature for 1 h. The reaction mixture was poured into a separatory funnel and washed with 1 M HCl (2×100 mL). The organic layer was separate and dried over anhydrous MgSO$_4$, filtered, concentrated and dried under high vacuum to give a yellow oil (7.11 g, 90.1%). This material was used without further purification. $^1$HNMR (CDCl$_3$, 400 MHz): δ 0.91-0.98 (m, 3H), 1.27-1.37 (m, 2H), 1.46 (s, 6H), 1.47-1.57 (m, 2H), 2.49 (s, 2H), 2.92 (s, 1.35H), 3.02 (s, 1.48H) methyl rotamers, 3.28-3.39 (m, 2H). LRMS (ESI+) for C$_{10}$H$_{20}$N$_4$O (212.2); Found: 213 (MH+).

Benzyl 4-(butyl(methyl)amino)-2-methylbutan-2-ylcarbamate

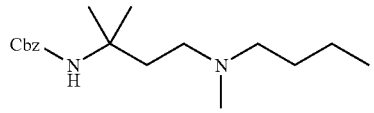

3-Azido-N-butyl-N,3-dimethylbutanamide (6.5 g, 30.6 mmol) was dissolved into anhydrous THF (50 mL) and added dropwise to a suspension of LAH (2.32 g, 2.0 equiv, 61.2 mmol) in anhydrous THF (100 mL) to maintain the reaction at reflux (30 min). After complete addition, the flask was fitted with a condenser and the reaction heated in a 70° C. oil bath for 8 h. The reaction mixture was cooled in an ice bath and water (1.75 mL) was added dropwise over 20 min. Then 15% NaOH solution (1.75 mL) was added dropwise over 10 min. The suspension was stirred for a further 10 min and water (3.5 mL) was added in one portion and the mixture stirred for 30 min to a give fine white suspension. The suspension was filtered through a pad of Celite® and washed with isopropanol (2×75 mL). The combined filtrate was carefully concentrated on a rotovap with the bath temperature set to 20° C. to give a pale yellow liquid which was briefly dried under high vacuum to give a liquid (5.12 g, quant). The crude amine was not dried completely to minimize loss of product due to its low b.p. and used without further purification.

Crude $N^1$-butyl-$N^1$,3-dimethylbutane-1,3-diamine (5.00 g, 29.0 mmol) was dissolved into THF (100 mL). To this solution was added CbzOSu (7.23 g, 1 equiv, 29.0 mmol) in one portion. The reaction was left to stir at room temperature for 3 d. The solvent was removed and the residue was taken up in a mixture of diethyl ether (150 mL) and water (50 mL). The layers were separated and the organic layer washed with 1 M sodium carbonate (2×50 mL), 1M HCl (50 mL), and brine (100 mL). The organic layer was dried over anhydrous $MgSO_4$, filtered and concentrated to a pale yellow oil. The crude oil was purified on an ISCO purification system with gradient elution from 10-80% ethyl acetate in hexanes. The desired fractions were collected and concentrated to give a white solid (3.55 g, yield: 40.0%). $^1$H NMR (CDCl$_3$, 400 MHz): δ 0.83-0.87 (t, J=7.2, 3H), 1.25-1.35 (m, 2H), 1.40 (s, 6H), 1.41-1.45 (m, 2H), 1.59-1.62 (t, J=6.4, 2H), 2.18 (s, 3H), 2.28-2.32 (t, J=6.4, 2H), 2.43-2.47 (t, J=6.4, 2H), 5.04 (s, 2H), 7.27-7.37 (m, 5H). LRMS (ESI+) for $C_{18}H_{30}N_2O_2$ (306.2); Found: 307 (MH+).

3-(Benzyloxycarbonylamino)-N-butyl-N,N,3-trimethylbutan-1-ammonium iodide

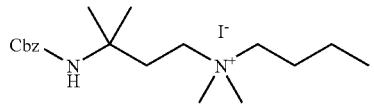

Benzyl 4-(butyl(methyl)amino)-2-methylbutan-2-ylcarbamate (2.25 g, 6.76 mmol) was placed into a 15 mL pressure tube. Absolute ethanol (2 mL) was added to tube to give a solution. Methyl iodide (5.0 mL, 10.7 equiv, 80.1 mmol) was added to the reaction in one portion. A stir bar was added and the pressure tube sealed. The reaction was left to stir at 50° C. for 16 h. The thick suspension was filtered and washed with diethyl ether (3×100 mL) to give a pale yellow powder which was dried under high vacuum (2.47 g, 73.6%). $^1$H NMR (D$_2$O, 400 MHz): δ 0.90-0.95 (t, J=7.2, 3H), 1.30 (s, 6H), 1.30-1.38 (m, 2H), 1.54-1.62 (m, 2H), 2.10-2.18 (m, 2H), 2.89 (s, 6H), 3.11-3.21 (m, 4H), 5.09 (s, 2H), 7.38-7.50 (m, 5H). LRMS (ESI+) for $C_{19}H_{33}N_2O_2^+$ (321.3); Found: 321 (M+).

3-Amino-N-butyl-N,N,3-trimethylbutan-1-ammonium chloride hydrochloride

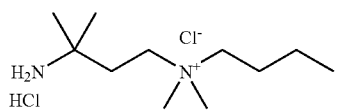

Ag$_2$O (1.18 g, 1.0 equiv, 5.06 mmol) was added in one portion to a solution of 3-(benzyloxycarbonylamino)-N-butyl-N,N,3-trimethylbutan-1-ammonium iodide (2.27 g, 5.06 mmol) into a mixture of methanol (150 mL), water (100 mL) and acetic acid (0.87 mL). The black suspension immediately changed to a cream color suspension. The reaction was stirred at room temperature for 30 min. Aqueous 6 N HCl (5 mL) was added to the flask in one portion to give a white cloudy suspension. The suspension was stirred for 15 min, then filtered through a pad of Celite® and the solid was washed with water (2×30 mL). 10% Pd/C (300 mg) was added to the combined filtrate and the flask sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to an oil which was dissolved into methanol (25 mL), filtered through a 0.45 micron PTFE frit. The filtrate was concentrated to an oil, dried under high vacuum to give a foam (1.35 g, quant). $^1$H NMR (D$_2$O, 400 MHz): δ 0.94-0.99 (t, J=7.6, 3H), 1.35-1.43 (s, 8H), 1.71-1.80 (m, 2H), 2.12-2.19 (m, 2H), 3.11 (s, 3 H), 3.32-3.38 (m, 2H), 3.44-3.49 (2 H). LRMS (ESI+) for $C_{11}H_{27}N_2^+$ (187.2); Found: 187 (M+).

N-Butyl-3-(dichloroamino)-N,N,3-trimethylbutan-1-ammonium chloride

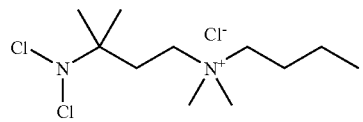

A solution of 3-amino-N-butyl-N,N,3-trimethylbutan-1-ammonium chloride hydrochloride (0.51 g, 1.96 mmol) in a mixture of methanol (10 mL) and water (8 mL) was cooled in an ice bath for 15 min. t-BuOCl (0.70 mL, 3 equiv, 5.89 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a pale yellow foam, (0.468 g, 82.0%). $^1$H NMR (D$_2$O, 400 MHz): δ 0.93-0.98 (t, J=7.6, 3H), 1.34-1.44 (sext, J=7.6, 2H), 1.46 (s, 6H), 1.71-1.81 (m, 2H), 2.20-2.60 (m, 2H), 3.09 (s, 3 H), 3.29-3.34 (m, 2H), 3.40-3.45 (2 H). LRMS (ESI+) for $C_{11}H_{25}Cl_2N_2^+$ (255.1); Found: 255, 257 (M+, M+2).

Example 22

N-(3-(Dichloroamino)-3-methylbutyl)-N,N-dimethylcyclohexanammonium chloride (Compound 21-126)

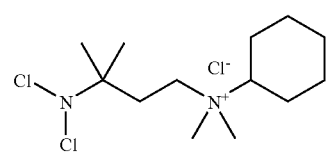

c) 3-Azido-N-cyclohexyl-N-3-dimethylbutanamide (3)

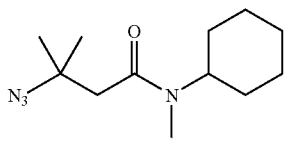

To a stirred ice cold solution of N-methylcyclohexylamine (5.59 g, 1 equiv, 49.4 mmol) and DIEA (12.9 mL, 1.5 equiv, 74.4 mmol) in anhydrous DCE (250 mL) was added 3-azido-3-methylbutanoyl chloride (7.98 g, 49.4 mmol) in small portions. The reaction was stirred at 0° C. for 1 h. Water (200 mL) was added to the reaction mixture and the contents poured into a separatory funnel. The organic layer was separated and washed with 1 M HCl (2×150 mL) and 1 M NaOH (2×150 mL). It was dried over anhydrous $MgSO_4$, filtered, concentrated and dried under high vacuum to give a crude oil (12.3 g, quant). This material was used without further purification.

Benzyl 4-(cyclohexyl(methyl)amino)-2-methylbutan-2-ylcarbamate

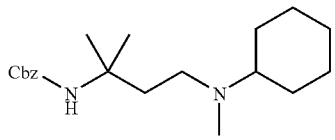

3-Azido-N-cyclohexyl-N-3-dimethylbutanamide (11.0 g, 46.1 mmol) was dissolved into anhydrous THF (100 mL) and added dropwise to a suspension of LAH (3.50 g, 2.0 equiv, 92.2 mmol) in anhydrous THF (200 mL) to maintain the reaction at reflux (30 min). After complete addition, the flask was fitted with a condenser and the reaction heated in a 70° C. oil bath for 8 h. The reaction mixture was cooled in an ice bath and water (3.5 mL) was added dropwise over 20 min. Then 15% NaOH solution (3.5 mL) was added dropwise over 10 min. The suspension was stirred for a further 10 min and water (7 mL) was added in one portion and the mixture stirred for 30 min to a give fine white suspension. The suspension was filtered through a pad of Celite® and washed with isopropyl alcohol (2×100 mL). The combined filtrate was carefully concentrated on a rotovap with the bath temperature set to 20° C. to give a pale yellow liquid. Aqueous acid (6 N HCl, 17.0 mL) was added to the liquid and concentrated to a semi solid which was dried under high vacuum to give 14.0 g (yield: quant).

Sodium hydrogen carbonate (15.0 g, 0.18 mol) dissolved in water (200 mL) was added to reaction containing crude $N^1$-cyclohexyl-$N^1$,3-dimethylbutane-1,3-diamine (14.0 g, 46.1 mmol) was dissolved into THF (200 mL). CbzOSu (11.0 g, 1 equiv, 44.2 mmol) was added in one portion to the reaction and left to stir at room temperature for 16 h. The organic solvent was removed and the aqueous residue was extracted with DCM (3×150 mL). The organic layer was dried over anhydrous $MgSO_4$, filtered and concentrated to a pale yellow oil (12.7 g). The crude oil was purified on an ISCO purification system with gradient elution from 20-100% ethyl acetate then 1-10% methanol in ethyl acetate. The desired fraction was collected and concentrated to give a colorless oil (5.27 g, yield: 34.4%). $^1$H NMR ($CDCl_3$, 400 MHz): δ 1.0-1.49 (m, 5H), 1.37 (s, 6H), 1.55 (t, 2H), 1.6-1.64 (m, 1H), 1.76 (bs, 4H), 2.21 (s, 3H), 2.32-2.4 (m, 1H), 2.60 (t, 2H), 5.03 (s, 2H), 7.2-7.4 (m, 5H), 7.96 (s, 1H). LRMS (ESI+) for $C_{20}H_{32}N_2O_2$ (332.3); Found: 333 (MH+).

N-(3-(Benzyloxycarbonylamino)-3-methylbutyl)-N,N-dimethylcyclohexan-ammonium Iodide

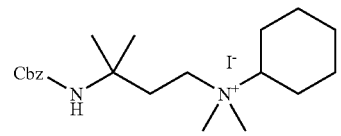

Benzyl 4-(cyclohexyl(methyl)amino)-2-methylbutan-2-ylcarbamate (2.69 g, 8.08 mmol) was placed into a 15 mL pressure tube. Methyl iodide (5.0 mL, 10 equiv, 80.8 mmol) and absolute ethanol (2.0 mL) was added to the reaction. Heat evolved and the tube was cooled in a water bath. A stir bar was added and the pressure tube sealed. The reaction was left to stir at 50° C. for 16 h. The solution was transferred to a round bottomed flask and concentrated to a dark red oil. The oil partially solidified on standing. The crude was recrystallized from a mixture of ether (20 mL) and hexanes (20 mL). A solid formed on standing overnight and was collected on a Buchner funnel, rinsed with small amounts of 10% ether in hexanes (5×20 mL) and dried under high vacuum to give a yellow solid (1.84 g, 48%). $^1$H NMR ($D_2O$, 400 MHz): δ 1.1-1.2 (m, 1H), 1.30 (s, 6H), 1.25-1.43 (m, 4H), 1.60-1.68 (m, 1H), 1.87-2.00 (dt, 4H), 2.10-2.15 (m, 2 H), 2.83 (s, 6H), 3.15-3.25 (m, 2H), 5.08 (s, 2H), 7.41-7.46 (m, 5H), LRMS (ESI+) for $C_{21}H_{35}N_2O_2^+$ (347.3); Found: 347 (M+).

N-(3-Amino-3-methylbutyl)-N,N-dimethylcyclohexanammonium chloride hydrochloride

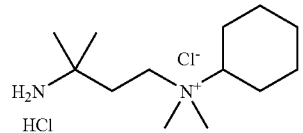

$Ag_2O$ (0.78 g, 1.0 equiv, 3.34 mmol) was added to a solution of N-(3-(benzyloxycarbonylamino)-3-methylbutyl)-N,N-dimethylcyclohexan-ammonium Iodide (1.63 g, mmol) in a mixture of methanol (20 mL), water (40 mL) and acetic acid (0.2, mL, 1.0 equiv). The black suspension immediately changed to a cream colored suspension. The reaction was stirred at room temperature for 30 min. Aqueous 6 N HCl (2.3 mL) was added to the suspension in one portion. The reaction was stirred for 15 min, then filtered through a pad of Celite® and the solid was washed with water (2×30 mL). 10% Pd/C (200 mg) was added to the combined filtrate and the flask sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to a colorless viscous oil which became a colorless foam after being dried under high vacuum (0.98 g, quant). $^1$H NMR ($D_2O$, 400 MHz): δ 1.30-1.40 (m, 2H), 1.43 (s, 6H), 1.50-1.63 (dq, 2H), 1.64-1.72 (m, 1H), 1.95-2.02 (bd, 2H), 2.10-2.20 (m, 4H), 3.06 (s, 6H), 3.35-3.44 (tt, 1H), 3.45-3.50 (m, 2H). LRMS (ESI+) for $C_{13}H_{29}N_2^+$ (213.2); Found: 213 (M+).

N-(3-(Dichloroamino)-3-methylbutyl)-N,N-dimethylcyclohexanammonium chloride

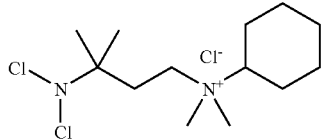

A solution of N-(3-amino-3-methylbutyl)-N,N-dimethylcyclohexanammonium chloride hydrochloride (0.542 g, 1.90 mmol) in methanol (20 mL) was cooled in an ice bath for 15 min. t-BuOCl (0.67 mL, 3 equiv, 5.7 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and lyophilized to give a pale yellow solid, (0.216 g, 35.0%). $^1$H NMR (D$_2$O, 400 MHz): δ 1.10-1.23. (tq, 1H), 1.42 (s, 6H), 1.48-1.60 (dq, 2H), 1.63-1.70 (m, 1H), 1.90-2.00 (bd, 2H), 2.12-2.19 (2H), 2.19-2.25 (m, 2 H), 3.02 (s, 6H), 3.30-3.40 (tt, 1H), 3.40-3.48 (m, 2H). LRMS (ESI+) for $C_{13}H_{27}Cl_2N_2^+$ (281.2); Found: 281, 283 (M+, M2H+).

Example 23

$N^1$-(3-(Dichloroamino)-3-methylbutyl)-$N^1$,$N^1$,$N^3$,$N^3$,$N^3$-pentamethylpropane-1,3-diammonmium chloride (Compound 21-128)

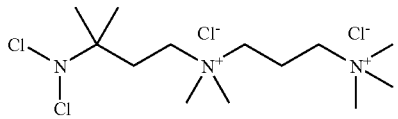

3-Azido-N-(3-(dimethylamino)propyl)-N,3-dimethylbutanamide

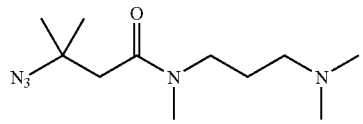

To a stirred ice cold solution of $N^1$,$N^1$,$N^3$-trimethylpropane-1,3-diamine (5.0 g, 1 equiv, 43.0 mmol) and DIEA (11.2 mL, 1.5 equiv, 64.5 mmol) in anhydrous DCE (200 mL) was added 3-azido-3-methylbutanoyl chloride (6.95 g, 43.0 mmol) in small portions. The reaction was stirred and left at 0° C. for 1 h. Aqueous NaOH (5N, 4 equiv, 34.5 mmol) was added to the reaction mixture. The solvent and DIEA was removed via rotovap to give an oily aqueous mixture. The contents of the flask were poured into a separatory funnel and extracted with DCM (2×100 mL). The organic layer was dried over anhydrous MgSO$_4$, filtered, concentrated and dried under high vacuum to give a crude oil (8.71 g, 84.0%). This material was used without further purification. $^1$H NMR (D$_2$O, 400 MHz): δ 1.34 (t, J=7.2, 3H), 1.43 (s, 6H), 2.11-2.15 (m, 2H), 3.09 (s, 3 H), 3.35 (s, 2H), 3.41 (dt, J=7.2, 4H). LRMS (ESI+) for $C_{11}H_{23}N_5O$ (241.2); Found: 241 (M+).

Benzyl 4-((3-(dimethylamino)propyl)(methyl)amino)-2-methylbutan-2-ylcarbamate

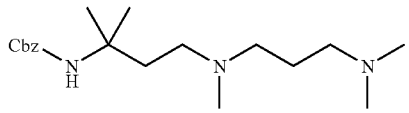

3-Azido-N-(3-(dimethylamino)propyl)-N,3-dimethylbutanamide (7.71 g, 39.1 mmol) was dissolved into anhydrous THF (100 mL) and added dropwise to a suspension of LAH (2.42 g, 2.0 equiv, 63.8 mmol) in anhydrous THF (200 mL) to maintain the reaction at reflux (30 min). After complete addition, the flask was fitted with a condenser and the reaction heated in a 70° C. oil bath for 8 h. The reaction mixture was cooled in an ice bath and water (2.5 mL) was added dropwise over 20 min. Then 15% NaOH solution (2.5 mL) was added dropwise over 10 min. The suspension was stirred for a further 10 min and water (5 mL) was added in one portion and the mixture stirred for 30 min to a give fine white suspension. The suspension was filtered through a pad of Celite® and washed with isopropyl alcohol (2×100 mL). The combined filtrate was acidified with aqueous acid (6 N HCl, 17.0 mL) was added to the liquid and concentrated to a semi solid on a rotovap which was further dried under high vacuum to give 18.0 g.

Crude $N^1$-(3-(Dimethylamino)propyl)-$N^1$,3-dimethylbutane-1,3-diamine (18.0 g, 31.9 mmol) was dissolved into THF (200 mL). Sodium hydrogen carbonate (14.0 g, 0.167 mol) dissolved in water (200 mL) was added to reaction to give a solution. CbzOSu (7.95 g, 1 equiv, 31.9 mmol) was added in one portion to the reaction and left to stir at room temperature for 16 h. The organic solvent was removed via rotovap and the aqueous concentrated to ~100 mL. The aqueous was extracted with DCM (2×200 mL). The organic layer was dried over anhydrous MgSO$_4$, filtered and concentrated to a pale yellow oil. The crude oil was purified on a Shimadzu Prep-LC utilizing water/acetonitrile and 0.05% acetic acid as modifier. Fractions were collected monitoring UV absorbance at 215 nm. The desired fractions were collected and lyophilized to give a colorless oil (5.57 g, yield: 52.1%). LRMS (ESI+) for $C_{19}H_{33}N_3O_2$ (335.3); Found: 336 (MH+).

$N^1$-(3-(Benzyloxycarbonylamino)-3-methylbutyl)-$N^1$,$N^1$,$N^3$,$N^3$,$N^3$-pentamethylpropane-1,3-diammonium chloride

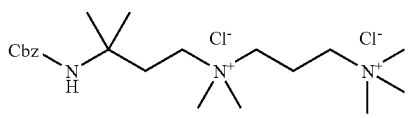

Benzyl 4-((3-(dimethylamino)propyl)(methyl)amino)-2-methylbutan-2-ylcarbamate (2.75 g, 8.2 mmol) was placed into a 75 mL pressure vessel. Methyl iodide (15.0 mL, 5.6 equiv, 46.4 mmol) was added to the reaction in one portion. No heat was evolved and absolute EtOH (15 mL) was added to the vessel. The reaction was left to stir at 50° C. for 16 h. The solution was transferred to a round bottomed flask and concentrated to a dark red oil. The oil was dissolved into water (100 mL), acetic acid (0.49 mL) and Ag$_2$O (1.90 g, 1.0 equiv, 8.2 mmol) were added to the red solution to give a black suspension. The black suspension immediately changed to a cream color suspension. The reaction was stirred at room temperature for 30 min. Aqueous 6 N HCl (4 equiv, 5.5 mL) was added to the flask in one portion and stirred for 30 min. The suspension was filtered through a pad of Celite® and the solid was washed with water. The filtrate was concentrated to a small volume and filtered through a 0.45 micron PTFE frit. The filtrate was concentrated to a small volume and purified on a Shimadzu Prep-LC utilizing water/acetonitrile and 0.05% acetic acid as modifier. Fractions were collected monitoring UV absorbance at 215 nm. The fractions were pooled and lyophilized to give a white foam (1.68 g, 46.9%). $^1$H NMR (D$_2$O, 400 MHz): δ 1.31 (s, 6H), 2.15-2.25 (m, 4H), 3.03 (s, 6H), 3.14 (s, 9 H), 3.25-3.35 (m, 6H), 5.09 (s, 2H), 7.40-7.47 (m, 5H). LRMS (ESI+) for C$_{21}$H$_{39}$N$_3$O$_2$$^{2+}$ (365.3); Found: 183 (M$^{2+}$/2).

N$^1$-(3-Amino-3-methylbutyl)-N$^1$,N$^1$N$^3$,N$^3$,N$^3$-pentamethylpropane-1,3-diammonium chloride hydrochloride

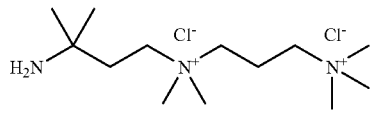

N$^1$-(3-(Benzyloxycarbonylamino)-3-methylbutyl)-N$^1$,N$^1$, N$^3$,N$^3$,N$^3$-pentamethylpropane-1,3-diammonium chloride (1.60 g, 3.67 mmol) was dissolved into water (50 mL) and 10% Pd/C (200 mg) was added to the solution and the flask was sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to a viscous oil via rotovap and transferred to vials which were lyophilized to give a white solid (1.25 g, quant). $^1$H NMR (D$_2$O, 400 MHz): δ 1.44 (s, 6H), 2.20-2.27 (m, 2H), 2.32-2.43 (m, 2H), 3.20 (s, 6H), 3.21 (s, 9H), 3.42-3.51 (q, 4H), 3.55-3.63 (m, 2H). LRMS (ESI+) for C$_{13}$H$_{33}$N$_3$$^{+2}$ (231.3); Found: 116 (M$^{2+}$/2).

N$^1$-(3-Dichloroamino-3-methylbutyl)-N$^1$,N$^1$,N$^3$,N$^3$, N$^3$-pentamethylpropane-1,3-diammonium chloride

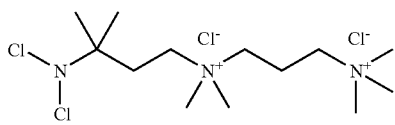

A solution of N$^1$-(3-amino-3-methylbutyl)-N$^1$,N$^1$,N$^3$,N$^3$, N$^3$-pentamethylpropane-1,3-diammonium chloride hydrochloride (0.634 g, 1.87 mmol) in a mixture of methanol (15 mL) and water (15 mL) was cooled in an ice bath for 15 min. t-BuOCl (0.66 mL, 3 equiv, 5.62 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and lyophilized to give a yellow solid, (0.44 g, 62.7%). $^1$H NMR (D$_2$O, 400 MHz): δ 1.46 (s, 6H), 2.24-2.29 (m, 2H), 2.30-2.41 (m, 2H), 3.17 (s, 6H), 3.21 (s, 9H), 3.40-3.48 (m, 2H), 3.50-3.55 (m, 2H). 1.46 (s, 6H), 2.18-2.22 (m, 2H), 2.99 (s, 3 H), 3.33-3.40 (m, 6H). LRMS (ESI+) for C$_{13}$H$_{31}$Cl$_2$N$_3$$^{2+}$(299.2); Found: 149 (M$^{2+}$/2).

Example 24

Synthesis of 1-(3-(Dichloroamino)-3-methylbutyl)-1-methylpyrrolidinium chloride Compound (21-130)

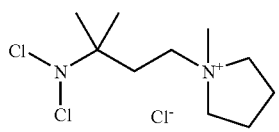

3-Azido-3-methyl-1-(pyrrolidin-1-yl)butan-1-one

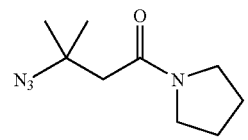

To a stirred ice cold solution of 3-azido-3-methylbutanoyl chloride (6.00 g, 37.1 mmol) in anhydrous DCE (100 mL) was added pyrrolidine (6.19 mL, 2 equiv, 74.2 mmol) in one portion. The reaction was stirred and left at 0° C. for 1 h. Water (100 mL) was added to the reaction mixture and the contents poured into a separatory funnel. The organic layer was separated and washed with water (3×100 mL) and brine (100 mL). It was dried over anhydrous MgSO$_4$, filtered, concentrated and dried under high vacuum to give a crude oil (6.23 g, 85.6%). This material was used without further purification. $^1$H NMR (CDCl$_3$, 400 MHz): δ 1.47 (s, 6H), 1.82-1.90 (q, J=6.8, 2H), 1.92-2.00 (q, J=6.8, 2H), 2.45 (s, 2H), 3.44-3.50 (t, J=6.8, 4H). 1.43 (s, 6H), 2.11-2.15 (m, 2H), 3.09 (s, 3 H), 3.35 (s, 2H), 3.41 (dt, J=7.2, 4H). LRMS (ESI+) for C$_9$H$_{16}$N$_4$O (196.1); Found: 197 (MH+).

2-Methyl-4-(pyrrolidin-1-yl)butan-2-amine

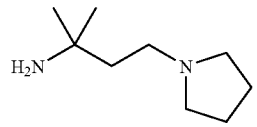

3-Azido-3-methyl-1-(pyrrolidin-1-y0butan-1-one (6.23 g, 31.7 mmol) was placed into an ice cooled 500 mL round bottomed flask. A solution of BH$_3$.THF (200 mL, 6.3 equiv, 0.2 mol) was added dropwise to the flask over 30 min. The flask was removed from the ice bath and stirred at room temperature for 30 min. The flask was fitted with a condenser and the reaction heated in a 70° C. oil bath for 8 h. The reaction mixture was cooled in an ice bath and methanol (50 mL) was added dropwise over 20 min. Then, 4 M HCl in dioxanes (50 mL) was added in one portion. The solution was stirred for 1 h at room temperature then concentrated to an oily residue. The residue was dissolved into DCM (150 mL) and 2.5 N NaOH solution (50 mL, 4 equiv) was added in one portion and the mixture stirred for 30 min. The mixture was poured into a separatory funnel and the layers separated. The organic layer was dried over anhydrous MgSO$_4$, filtered and concentrated to a pale yellow liquid (5.7 g, quant). The crude amine was not dried completely to minimize loss of product due to its low b.p. and used without further purification. LRMS (ESI+) for C$_9$H$_{20}$N$_2$ (156.2); Found: 157 (MH+).

Benzyl 2-methyl-4-(pyrrolidin-1-yl)butan-2-ylcarbamate

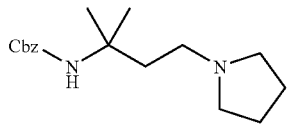

Crude 2-methyl-4-(pyrrolidin-1-yl)butan-2-amine (5.70 g, 31.7 mmol) was dissolved into THF (200 mL). To this solution was added CbzOSu (7.92 g, 1 equiv, 31.7 mmol) in one portion. The reaction was left to stir at room temperature for 16 h. The solvent was removed and the residue was taken up in a mixture of ethyl acetate (150 mL) and water (50 mL). The layers were separated and the organic layer washed with 1 M sodium carbonate (2×50 mL), 1 M HCl (50 mL) and brine (50 mL). The organic layer was dried over anhydrous MgSO$_4$, filtered and concentrated to a pale yellow oil (9.0 g). The crude oil was purified on an ISCO purification system with gradient elution from 5-90% ethyl acetate in hexanes. The desired fraction was collected and concentrated to give a pale yellow oil (5.76 g, yield: 62.5%). $^1$H NMR (CDCl$_3$, 400 MHz): δ 1.34 (s, 6H), 1.76-1.84 (m, 6H), 2.58-2.66 (m, 6H), 5.04 (s, 2H), 6.36 (bs, 1H), 7.27-7.39 (m, 5H). LRMS (ESI+) for C$_{17}$H$_{26}$N$_2$O$_2$ (290.2); Found: 291 (MH+).

1-(3-(Benzyloxycarbonylamino)-3-methylbutyl)-1-methylpyrrolidinium iodide

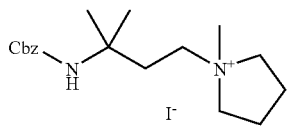

Benzyl 2-methyl-4-(pyrrolidin-1-yl)butan-2-ylcarbamate (4.81 g, 16.6 mmol) was placed into a 48 mL pressure vessel. Methyl iodide (10 mL, 10 equiv, 0.16 mol) was added to the reaction in one portion. No heat was evolved during addition, absolute ethanol (5 mL) was added to the vessel then it was sealed. The reaction was left to stir at 50° C. for 16 h. The blood red solution was concentrated to a dark red oil. The crude product was dissolved into a small amount of water and filtered through a 0.45 micron PTFE frit, then this solution was purified on a Shimadzu Prep-LC utilizing water/acetonitrile and 0.05% acetic acid as modifier. Fractions were collected monitoring UV absorbance at 215 nm. The fractions were pooled and lyophilized to give a colorless oil (5.24 g, 73.2%). $^1$H NMR (CDCl$_3$, 400 MHz): δ 1.29 (s, 6H), 2.02-2.25 (m, 6H), 2.88 (s, 3H), 3.15-3.30 (m, 4H), 3.32-3.45 (m, 2H), 5.08 (s, 2H), 7.38-7.50 (m, 5H). LRMS (ESI+) for C$_{18}$H$_{29}$N$_2$O$_2{}^+$ (305.2); Found: 305 (M+).

1-(3-Amino-3-methylbutyl)-1-methylpynolidinium chloride hydrochloride

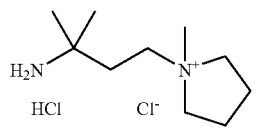

1-(3-(Benzyloxycarbonylamino)-3-methylbutyl)-1-methylpyrrolidinium iodide (5.24 g, 12.1 mmol) was dissolved into a mixture of methanol (100 mL) and water (200 mL) and Ag$_2$O (1.82 g, 0.65 equiv, 7.86 mmol) was added in one portion. The black suspension immediately changed to a cream color suspension. The reaction was stirred at room temperature for 30 min. Aqueous 6 N HCl (5.25 mL, 2.6 equiv, 31.4 mmol) was added to the flask in one portion to give a white cloudy suspension. The suspension was stirred for 15 min, then filtered through a pad of Celite® and the solid was washed with water (2×30 mL). 10% Pd/C (300 mg) was added to the combined filtrate and the flask sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated via rotovap to pale yellow foam (2.61 g, 88.6%). $^1$H NMR (D$_2$O, 400 MHz): δ 1.42 (s, 6H), 2.19-2.38 (m, 6H), 3.09 (s, 3H), 3.48-3.75 (m, 4H), 3.75-3.65 (m, 2H). LRMS (ESI+) for C$_{10}$H$_{23}$N$_2{}^+$ (171.2); Found: 171 (M+).

1-(3-(Dichloroamino)-3-methylbutyl)-1-methylpyrrolidinium chloride

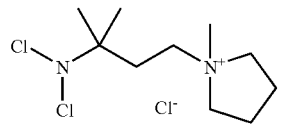

A solution of 1-(3-amino-3-methylbutyl)-1-methylpyrrolidinium chloride hydrochloride (1.07 g, 4.4 mmol) in a mixture of methanol (15 mL) and water (10 mL) was cooled in an ice bath for 15 min. t-BuOCl (1.56 mL, 3 equiv, 13.2 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and lyophilized to give a pale yellow foam, (0.94 g, 77.6%). $^1$H NMR (D$_2$O, 400 MHz): δ 1.44 (s, 6H), 2.17 (m, 4H), 2.17-2.32 (m, 2H), 3.06 (s, 3 H), 3.45-3.60 (m, 6H). LRMS (ESI+) for C$_{10}$H$_{21}$Cl$_2$N$_2{}^+$ (239.1); Found: 239, 241 (M+, M2H+).

Example 25

3-(Dichloroamino)-N,N,3-trimethyl-N-(2,2,2-trifluoroethyl)butan-1-ammonium chloride (Compound 21-132)

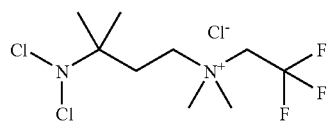

3-Azido-3-methyl-N-(2,2,2-trifluoroethyl)butanamide

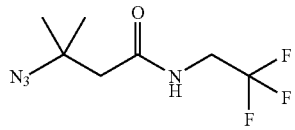

To a stirred ice cold solution of 2,2,2-trifluoroethanamine hydrochloride (7.10 g, 1 equiv, 52.4 mmol) and DIEA (18.0 mL, 2.0 equiv, 0.103 mol) in anhydrous DCE (150 mL) was added 3-azido-3-methylbutanoyl chloride (8.46 g, 52.4 mmol) in small portions. The ice bath was removed and the reaction was stirred and left at room temperature for 3 h. Water (150 mL) was added to the reaction mixture and the contents poured into a separatory funnel. The organic layer was separated and washed with 1 M HCl (2×150 mL) and brine (150 mL). It was dried over anhydrous MgSO₄, filtered, concentrated and dried under high vacuum to give a crude oil (10.9 g, 94.4). This material was used without further purification. ¹H NMR (CDCl₃, 400 MHz): δ 1.42 (s, 6H), 2.40 (s, 2H), (dq, J=2.4 & 8.8, 2H). LRMS (ESI+) for $C_7H_{11}F_3N_4O$ (224.1); Found: 225 (MH+).

3-Methyl-$N^1$-(2,2,2-trifluoroethyl)butane-1,3-diamine

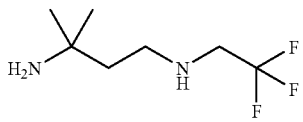

3-Azido-3-methyl-N-(2,2,2-trifluoroethyl)butanamide (10.9 g, 48.4 mmol) was dissolved into anhydrous THF (50 mL) and added dropwise to a suspension of LAH (3.67 g, 2.0 equiv, 96.8 mmol) in anhydrous THF (200 mL) to maintain the reaction at reflux (30 min). After complete addition, the flask was fitted with a condenser and the reaction heated in a 70° C. oil bath for 8 h. The reaction mixture was cooled in an ice bath and water (4 mL) was added dropwise over 20 min. Then 15% NaOH solution (4 mL) was added dropwise over 10 min. The suspension was stirred for a further 10 min and water (4 mL) was added in one portion and the mixture stirred for 30 min to a give fine white suspension. The suspension was filtered through a pad of Celite® and washed with isopropyl alcohol (2×200 mL). Aqueous acid (6 N HCl, 10.0 mL) was added to the combined filtrate and concentrated on a rotovap to an oily residue. The residue was partitioned between DCM (100 mL) and water (100 mL). The aqueous layer was adjusted to pH ~14 and the organic layer was separated and the aqueous phase was extracted with DCM (2×50 mL). The combined organic layers were combined and dried over anhydrous MgSO₄, filtered and concentrated with a bath temperature between 10-13° C. to an orange liquid (8.84 g, quant). ¹H NMR (CDCl₃, 400 MHz): δ 1.15 (s, 6H), 1.55-1.62 (t, J=7.2, 2H), 2.81-2.86 (t, J=7.2, 2H) 3.15-3.22 (q, J=9.6, 2H). LRMS (ESI+) for $C_7H_{15}F_3N_2$ (184.1); Found: 185 (MH+).

Benzyl 2-methyl-4-(2,2,2-trifluoroethylamino)butan-2-ylcarbamate

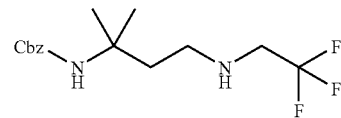

Crude 3-methyl-$N^1$-(2,2,2-trifluoroethyl)butane-1,3-diamine (3.86 g, 21.0 mmol) was dissolved into THF (200 mL) and cooled in an ice bath. A THF (50 mL) solution of CbzOSu (5.22 g, 1 equiv, 21.0 mmol) was added to the reaction dropwise over 5 min. The reaction was left to stand in an ice chest for 16 h. The solvent was removed and the residue was taken up in a mixture of ethyl acetate (150 mL) and water (50 mL). The layers were separated and the organic layer washed with 1 M sodium carbonate (2×50 mL), 1 M HCl (50 mL) and brine (50 mL). The organic layer was dried over anhydrous MgSO₄, filtered and concentrated to a pale yellow oil (6.15 g). The crude oil was purified on an ISCO purification system with gradient elution from 0-6% methanol in DCM. The desired fractions were collected and concentrated to give a pale yellow oil (4.57 g, yield: 68.5%). ¹H NMR (CDCl₃, 400 MHz): δ 1.33 (s, 6H), 1.75-1.83 (t, J=7.2, 2H), 2.74-2.85 (t, J=7.2, 2H) 3.10-3.18 (q, J=9.4, 2H), 5.04 (s, 2H), 7.27-7.38 (m, 5H). LRMS (ESI+) for $C_{15}H_{21}F_3N_2O_2$ (318.2); Found: 319 (MH+).

3-(Benzyloxycarbonylamino)-N,N,3-trimethyl-N-(2,2,2-trifluoroethyl)butan-1-ammonium iodide

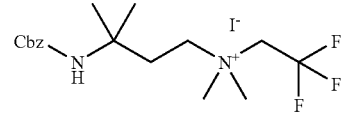

Benzyl 2-methyl-4-(2,2,2-trifluoroethylamino)butan-2-ylcarbamate (4.0 g, 12.6 mmol) was added to a 500 mL round bottomed flask and dissolved into DMF (150 mL). Cesium carbonate (4.10 g, 1 equiv, 12.6 mmol) and methyl iodide (7.8 mL, 10 equiv, 0.13 mol) was added to the reaction and the flask was fitted with a condenser. The system was sealed and vented through a bubbler. The reaction was left to stir at 48° C. for 16 h. The suspension was filtered through a sintered glass funnel. The solid was washed with ethyl acetate (50 mL) and the filtrate was concentrated to a dark red semi solid. The crude product was dissolved into DCM (50 mL) and filtered through 0.45 micron PTFE frit. The solution was concentrated and redissolved into water (15 mL). This solution was purified on a Shimadzu Prep-LC utilizing water/acetonitrile and 0.05% acetic acid as modifier. Fractions were collected monitoring UV absorbance at 215 nm. Fractions were pooled lyophilized to give a pale yellow oil (4.67 g, 78.0%). $^1$H NMR (D$_2$O, 400 MHz): δ 1.31 (s, 6H), 2.22-2.30 (m, 2H), 3.20 (s, 6H), 3.48-3.55 (m, 2H), 4.20-4.28 (q, J=8.4, 2H), 5.08 (s, 2H), 7.40-7.49 (m, 5H). LRMS (ESI+) for $C_{17}H_{26}F_3N_2O_2^+$ (347.2); Found: 347 (M+).

3-Amino-N,N,3-trimethyl-N-(2,2,2-trifluoroethyl) butan-1-ammonium chloride hydrochloride

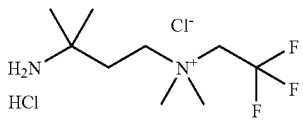

3-(Benzyloxycarbonylamino)-N,N,3-trimethyl-N-(2,2,2-trifluoroethyl)butan-1-ammonium iodide (4.46 g, 9.4 mmol) was placed into 500 mL round bottomed flask and dissolved into 33% HBr in acetic acid (20 mL). The flask was sealed with a latex septum and vented through an 18 gauge needle during the reaction. The reaction was stirred vigorously for 30 min and another 10 mL of 33% HBr in acetic acid was added the reaction and stirred for an additional hour. The reaction was concentrated on a rotovap to give a dark yellow residue. The residue was repeatedly dissolved in water (3×15 mL) and concentrated to give a yellow oil. The oil was redissolved into water (50 mL) then, acetic acid (3.4 mL, 6.0 equiv, 56.4 mmol) and Ag$_2$O (6.54 g, 3.0 equiv, 28.2 mmol) was added sequentially. The black suspension immediately changed to a cream color suspension. The reaction was stirred at room temperature for 30 min. Aqueous 6 N HCl (3.0 equiv 4.7 mL) was added to the flask in one portion to give a white cloudy suspension. The suspension was stirred for 15 min, then filtered through a pad of Celite® and the solid was washed with water (2×30 mL). The filtrate was concentrated to a white foam via rotovap. The foam was transferred to vials and dried on a lyophilizer to white foam. (2.61 g, 97.3). $^1$H NMR (D$_2$O, 400 MHz): δ 1.43 (s, 6H), 2.22-2.30 (m, 2H), 3.42 (s, 6H), 3.73-3.80 (m, 2H), 4.40-4.50 (q, J=8.4, 2H). LRMS (ESI+) for $C_9H_{20}F_3N_2^+$ (213.2); Found: 213 (M+).

3-(Dichloroamino)-N,N,3-trimethyl-N-(2,2,2-trifluoroethyl)butan-1-ammonium chloride

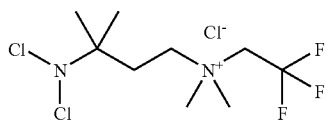

A solution of 3-amino-N,N,3-trimethyl-N-(2,2,2-trifluoroethyl)butan-1-ammonium chloride hydrochloride (1.30 g, 4.55 mmol) in a mixture of methanol (20 mL) and water 15 mL) which was cooled in an ice bath for 15 min. t-BuOCl (1.61 mL, 3 equiv, 13.7 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a pale yellow solid, (1.24 g, 85.3%). $^1$H NMR (D$_2$O, 400 MHz): δ 1.47 (s, 6H), 2.30-2.40 (m, 2H), 3.39 (s, 6H), 3.70-3.80 (m, 2H), 4.35-4.50 (q, J=8.4, 2H). LRMS (ESI+) for $C_9H_{18}F_3Cl_2N_2^+$ (281.1); Found: 281, 283 (M+, M2H+).

Example 26

3-(Dichloroamino)-N-ethyl-N,N,3-trimethylbutan-1-ammonium chloride Compound (21-134)

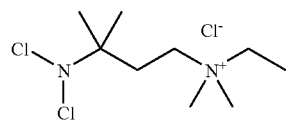

3-Azido-N-ethyl-N,3-dimethylbutanamide

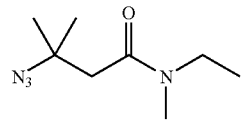

To a stirred ice cold solution of N-methylethanamine (2.65 mL, 1 equiv, 30.9 mmol) and DIEA (7.0 mL, 1.3 equiv, 40.2 mmol) in anhydrous DCM (150 mL) was added 3-azido-3-methylbutanoyl chloride (5.0 g, 30.9 mmol) in small portions. The ice bath was removed and the reaction was stirred and left at room temperature for 3 h. The contents of the reaction were poured into a separatory funnel. The organic layer was washed with 1 M HCl (3×100 mL) and saturated NaHCO$_3$ (2×100 mL). It was dried over anhydrous MgSO$_4$, filtered, concentrated and dried under high vacuum to give a crude oil (7.14 g, 96.1%). This material was purified on an ISCO flash chromatography system with ethyl acetate and hexanes as eluent. The desired fractions were collected and concentrated to give a pale yellow oil (5.09 g, 89.4%). $^1$H NMR (CDCl$_3$, 400 MHz): δ 1.42 (s, 6H), 2.40 (s, 2H), (dq, J=2.4 & 8.8, 2H). LRMS (ESI+) for $C_8H_{16}N_4O$ (184.1); Found: 185 (MH+).

N$^1$-Ethyl-N$^1$,3-dimethylbutane-1,3-diamine

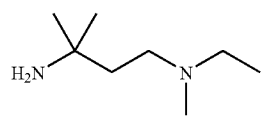

3-Azido-N-ethyl-N,3-dimethylbutanamide (5.09 g, 27.6 mmol) was dissolved into anhydrous THF (50 mL) and added dropwise to a suspension of LAH (2.10 g, 2.0 equiv, 55.2 mmol) in anhydrous THF (100 mL) to maintain the reaction at reflux (30 min). After complete addition, the flask was fitted with a condenser and the reaction heated in a 70° C. oil bath for 8 h. The reaction mixture was cooled in an ice bath and water (2.1 mL) was added dropwise over 20 min. Then 15% NaOH solution (2.1 mL) was added dropwise over 10 min. The suspension was stirred for a further 10 min and water (2.1 mL) was added in one portion and the mixture stirred for 30 min to a give fine white suspension. The suspension was filtered through a pad of Celite® and washed with diethyl ether (2×100 mL). The combined filtrate was concentrated with a bath temperature between 10-13° C. to an orange liquid (1.87 g, 47%). LRMS (ESI+) for $C_8H_{20}N_2$ (144.1); Found: 145 (MH+).

Benzyl 4-(ethyl(methyl)amino)-2-methylbutan-2-ylcarbamate

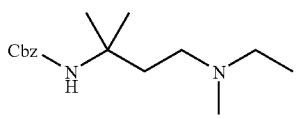

Crude $N^1$-ethyl-$N^1$,3-dimethylbutane-1,3-diamine (1.87 g, 12.9 mmol) was dissolved into THF (100 mL) and cooled in an ice bath. Solid CbzOSu (3.23 g, 1 equiv, 12.9 mmol) was added to the reaction in one portion. The reaction was left to stir at room temperature for 16 h. The solvent was removed and the residue was taken up in a mixture of ethyl acetate (150 mL) and water (50 mL). The layers were separated and the organic layer washed with 1 M sodium carbonate (2×50 mL) and brine (50 mL). The organic layer was dried over anhydrous MgSO₄, filtered and concentrated to a pale yellow oil (3.29 g). The crude oil was purified on an ISCO purification system with gradient elution from 15 to 100% ethyl acetate in hexanes. The desired fractions were collected and concentrated to give a pale yellow oil (1.81 g, yield: 55.5%). $^1$H NMR (CDCl₃, 400 MHz): δ 1.05-1.09 (t, J=8, 3H), 1.38 (s, 6H), 1.64-1.67 (t, J=6, 2H), 2.22 (s, 3H), 2.39-2.44 (q, J=6.6, 2H), 2.46-2.49 (t, J=6, 2H), 5.07 (s, 2H), 7.16 (bs, 1H), 7.28-7.41 (m, 5H). LRMS (ESI+) for $C_{16}H_{26}N_2O_2$ (278.2); Found: 279 (MH+).

3-(Benzyloxycarbonylamino)-N-ethyl-N,N,3-trimethylbutan-1-ammonium iodide

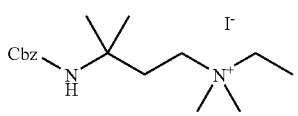

Benzyl 4-(ethyl(methyl)amino)-2-methylbutan-2-ylcarbamate (1.7 g, 6.11 mmol) was was placed into a 50 mL round bottom flask. Methyl iodide (5.7 mL, 10 equiv, 92.7 mmol) was added to the reaction in one portion. A stir bar was added and the flask sealed with a wired down septum. The reaction was left to stir at 50° C. for 16 h. The thick suspension was filtered and washed with diethyl ether (3×100 mL) to give a pale yellow powder which was dried under high vacuum. (2.40 g, 93.8%). $^1$H NMR (D₂O, 400 MHz): δ 1.07-1.18 (t, J=7.2, 3H), 1.19, (s, 6H), 2.00-2.04 (m, 2H), 2.77 (s, 6H), 3.04-3.13 (m, 4H), 4.97 (s, 2H), 7.30-7.37 (m, 5H). LRMS (ESI+) for $C_{17}H_{29}N_2O_2^+$ (293.2); Found: 293 (M+).

3-Amino-N-ethyl-N,N,3-trimethylbutan-1-ammonium chloride hydrochloride

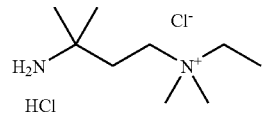

Ag₂O (1.21 g, 1.0 equiv, 5.39 mmol) was added in one portion to a solution of 3-(Benzyloxycarbonylamino)-N-ethyl-N,N,3-trimethylbutan-1-ammonium iodide (2.20 g, 5.23 mmol) in a mixture of methanol (35 mL), water (80 mL) and acetic acid (1.0 mL). The black suspension immediately changed to a cream color suspension. The reaction was stirred at room temperature for 30 min. Aqueous 6 N HCl (5 mL) was added to the flask in one portion to give a white cloudy suspension. The suspension was stirred for 15 min, then filtered through a pad of Celite® and the solid was washed with water (2×30 mL). 10% Pd/C (300 mg) was added to the combined filtrate and the flask sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to an oil which was dissolved into methanol (25 mL), filtered through a 0.45 micron PTFE frit. The filtrate was concentrated to an oil, dried under high vacuum to give a yellow oil (1.70 g, 140%). $^1$H NMR (D₂O, 400 MHz): δ 1.24-1.28 (t, J=8, 3H), 1.32 (s, 6H), 2.04-2.08 (m, 2H), 2.99 (s, 6H), 3.30-3.36 (m, 4H). LRMS (ESI+) for $C_9H_{23}N_2^+$ (159.2); Found: 159 (M+).

3-(Dichloroamino)-N-ethyl-N,N,3-trimethylbutan-1-ammonium chloride

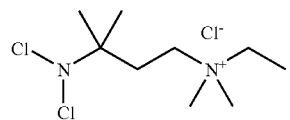

A solution of 3-amino-N-ethyl-N,N,3-trimethylbutan-1-ammonium chloride hydrochloride (1.70 g, 7.35 mmol) in a mixture of methanol (30 mL) and water (15 mL) was cooled in an ice bath for 15 min. t-BuOCl (2.60 mL, 3 equiv, 22.1 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a pale yellow solid, (0.79 g, 40.8%). $^1$H NMR (D₂O, 400 MHz): δ 1.25-1.28 (t, J=8, 3H), 1.36 (s, 6H), 2.12-2.16 (m, 2H), 2.97 (s, 6H), 3.28-3.34 (m, 4H). LRMS (ESI+) for $C_9H_{21}Cl_2N_2^+$ (227.1); Found: 227, 229 (M+, M2H+).

Example 27

N-Hexyl-3-(dichloroamino)-N,N,3-trimethylbutan-1-ammonium chloride Compound (21-136)

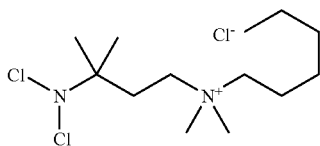

3-Azido-N-hexyl-N,3-dimethylbutanamide

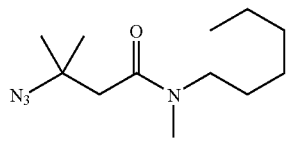

To a stirred ice cold solution of N-methylhexan-1-amine (4.69 mL, 1.0 equiv, 30.9 mmol) and DIEA (7.0 mL, 1.3 equiv, 40.2 mmol) in anhydrous DCE (150 mL) was added 3-azido-3-methylbutanoyl chloride (5.0 g, 30.9 mmol) in small portions over 5 min. The reaction was removed from the ice bath and stirred at room temperature for 1 h. The reaction mixture was poured into a separatory funnel and washed with 1 M HCl (3×100 mL) and saturated sodium hydrogen carbonate (2×100 mL). The organic layer was separate and dried over anhydrous MgSO$_4$, filtered, concentrated and dried under high vacuum to give a yellow oil (5.14 g, 72.0%). This material was used without further purification. $^1$H NMR (CDCl$_3$, 400 MHz): δ 0.88-0.94 (m, 3H), 1.2-1.35 (m, 6H), 1.47 (d, 6H), 1.47-1.66 (m, 2H), 2.51 (s, 2H), 2.94-3.04 (d, J=40 Hz, 3 H), 3.30-3.40 (m, 2H). LRMS (ESI+) for C$_{12}$H$_{24}$N$_4$O (240.2); Found: 241 (MH+).

Benzyl 4-(hexyl(methyl)amino)-2-methylbutan-2-ylcarbamate

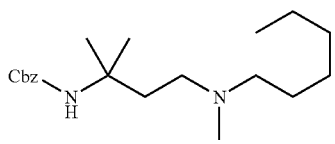

3-Azido-N-hexyl-N,3-dimethylbutanamide (5.0 g, 20.8 mmol) was dissolved into anhydrous THF (50 mL) and added dropwise to a suspension of LAH (1.57 g, 2.0 equiv, 41.6 mmol) in anhydrous THF (100 mL) to maintain the reaction at reflux (30 min). After complete addition, the flask was fitted with a condenser and the reaction heated in a 70° C. oil bath for 8 h. The reaction mixture was cooled in an ice bath and water (3.5 mL) was added dropwise over 20 min. Then 15% NaOH solution (1.75 mL) was added dropwise over 10 min. The suspension was stirred for a further 10 min and water (3.5 mL) was added in one portion and the mixture stirred for 30 min to a give fine white suspension. The suspension was filtered through a pad of Celite® and washed with isopropanol (2×75 mL). The combined filtrate was carefully concentrated on a rotovap with the bath temperature set to 20° C. to give a pale yellow liquid which was briefly dried under high vacuum to give a liquid (2.48 g, 60%).

Crude N$^1$-Hexyl-N$^1$-3-dimethylbutane-1,3-diamine (2.48 g, 12.3 mmol) was dissolved into THF (100 mL). To this solution was added CbzOSu (3.08 g, 1 equiv, 12.3 mmol) in one portion. The reaction was left to stir at room temperature for 3 d. The solvent was removed and the residue was taken up in a mixture of diethyl ether (150 mL) and water (50 mL). The layers were separated and the organic layer washed with 1 M sodium carbonate (2×50 mL), 1M HCl (50 mL), and brine (100 mL). The organic layer was dried over anhydrous MgSO$_4$, filtered and concentrated to a pale yellow oil. The crude oil was purified on an ISCO purification system with gradient elution from 10-80% ethyl acetate in hexanes. The desired fractions were collected and concentrated to give a white solid (3.23 g, yield: 78.5%). $^1$H NMR (CDCl$_3$, 400 MHz): δ 0.87-0.90 (t, J=6, 3H), 1.26-1.35 (m, 6H), 1.39 (s, 6H), 1.43-1.47 (m, 2H), 1.62-1.68 (m, 4H), 2.21 (s, 3H), 2.30-2.34 (t, J=8, 2H), 2.46-2.49 (t, J=6, 2H), 5.06 (s, 2H), 7.29-7.36 (m, 5H). LRMS (ESI+) for C$_{20}$H$_{34}$N$_2$O$_2$ (334.3); Found: 335 (MH+).

3-(Benzyloxycarbonylamino)-N-hexyl-N,N,3-trimethylbutan-1-ammonium iodide

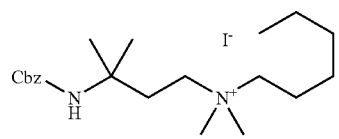

Benzyl 4-(hexyl(methyl)amino)-2-methylbutan-2-ylcarbamate (3.10 g, 9.27 mmol) was placed into a 50 mL round bottom flask. Methyl iodide (5.7 mL, 10 equiv, 92.7 mmol) was added to the reaction in one portion. A stir bar was added and the flask sealed with a wired down septum. The reaction was left to stir at 50° C. for 16 h. The thick suspension was filtered and washed with diethyl ether (3×100 mL) to give a pale yellow powder which was dried under high vacuum (4.23 g, 95.6%). $^1$H NMR (D$_2$O, 400 MHz): δ 0.90-0.95 (t, J=7.2, 3H), 1.30 (s, 6H), 1.30-1.38 (m, 2H), 1.54-1.62 (m, 2H), 2.10-2.18 (m, 2H), 2.89 (s, 6H), 3.11-3.21 (m, 4H), 5.09 (s, 2H), 7.38-7.50 (m, 5H). LRMS (ESI+) for C$_{21}$H$_{37}$N$_2$O$_2^+$ (349.3); Found: 349 (M+).

3-Amino-N-hexyl-N,N,3-trimethylbutan-1-ammonium chloride hydrochloride

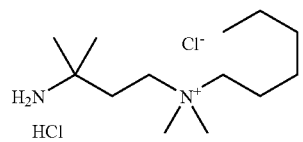

Ag$_2$O (1.94 g, 1.0 equiv, 8.39 mmol) was added in one portion to a solution of 3-(benzyloxycarbonylamino)-N-hexyl-N,N,3-trimethylbutan-1-ammonium iodide (4.0 g, 8.39 mmol) in a mixture of methanol (75 mL), water (125 mL) and acetic acid (1.0 mL). The black suspension immediately changed to a cream color suspension. The reaction was stirred at room temperature for 30 min. Aqueous 6 N HCl (5 mL) was added to the flask in one portion to give a white cloudy suspension. The suspension was stirred for 15 min, then filtered through a pad of Celite® and the solid was washed with water (2×30 mL). 10% Pd/C (300 mg) was added to the combined filtrate and the flask sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to an oil which was dissolved into methanol (25 mL), filtered through a 0.45 micron PTFE frit. The filtrate was concentrated to an oil, dried under high vacuum to give a yellow oil (2.54 g, 105%). $^1$H NMR (D$_2$O, 400 MHz): δ 0.75-0.79 (t, J=8, 3H), 1.21-1.27 (m, 6H), 1.32 (s, 6H), 1.62-1.70 (m, 2H), 2.03-2.08 (m, 2 H), 3.01 (s, 6H), 3.21-3.25 (m, 2H), 3.34-3.39 (m, 2 H). LRMS (ESI+) for $C_{13}H_{31}N_2^+$ (215.2); Found: 215 (M+).

N-Hexyl-3-(dichloroamino)-N,N,3-trimethylbutan-1-ammonium chloride

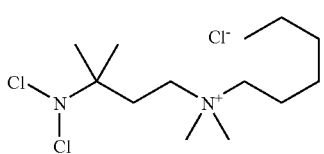

A solution of 3-Amino-N-hexyl-N,N,3-trimethylbutan-1-ammonium chloride hydrochloride (1.19 g, 4.15 mmol) in a mixture of methanol (75 mL) and water 40 mL) was cooled in an ice bath for 15 min. t-BuOCl (1.47 mL, 3 equiv, 12.5 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a pale yellow solid, (1.25 g, 94.3%). $^1$H NMR (D$_2$O, 400 MHz): δ 0.76-0.8 (t, J=8, 3H), 1.20-1.30 (m, 6H), 1.35 (s, 6H), 1.62-1.72 (m, 2H), 2.10-2.15 (m, 2 H), 2.99 (s, 6H), 3.19-3.23 (m, 2H), 3.30-3.34 (m, 2 H). LRMS (ESI+) for $C_{13}H_{29}N_2^+$ (283.2); Found: 283, 285 (M+, M2H+).

Example 28

N-(3-(Dichloroamino)-3-methylbutyl)-N,N-dimethyldodecan-1-ammonium chloride Compound (21-138)

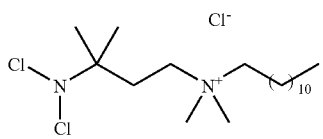

3-Azido-N-dodecyl-N,3-dimethylbutanamide

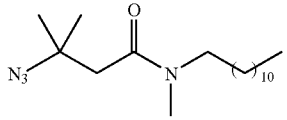

To a stirred ice cold solution of N-methyldodecanamine (5.0 g, 25.1 mmol) and DIEA (5.70 mL, 1.3 equiv, 32.6 mmol) in anhydrous DCM (150 mL) was added 3-azido-3-methylbutanoyl chloride (4.05 g, 1 equiv, 25.1 mmol) in small portions. The ice bath was removed and the reaction was stirred and left at room temperature for 3 h. The content of the reaction was poured into a separatory funnel. The organic layer was washed with 1 M HCl (3×100 mL) and saturated NaHCO$_3$ (2×100 mL). It was dried over anhydrous MgSO$_4$, filtered, concentrated and dried under high vacuum to give a crude oil (8.08 g, quant). This material was purified on an ISCO flash chromatography system with a gradient from 10-40% ethyl acetate and hexanes as eluent. The desired fractions were collected and concentrated to give a pale yellow oil (7.28 g, 89.3%). $^1$H NMR (CDCl$_3$, 400 MHz): δ 0.88-0.94 (m, 3H), 1.26-1.35 (m, 6H), 1.47-1.48 (d, J=4, 6H), 1.50-1.59 (m, 2H), 2.51 (s, 2H), 2.94-3.04 (d, J=40, 3H), 3.30-3.40 (m, 2H). LRMS (ESI+) for $C_{18}H_{36}N_4O$ (324.3); Found: 325 (MH+).

N$^1$-Dodecyl-N$^1$,3-dimethylbutane-1,3-diamine

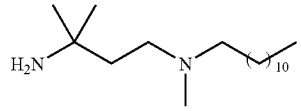

3-Azido-N-dodecyl-N,3-dimethylbutanamide (7.28 g, 22.4 mmol) was dissolved into anhydrous THF (50 mL) and added dropwise to a suspension of LAH (1.70 g, 2.0 equiv, 44.8 mmol) in anhydrous THF (100 mL) to maintain the reaction at reflux (30 min). After complete addition, the flask was fitted with a condenser and the reaction heated in a 70° C. oil bath for 8 h. The reaction mixture was cooled in an ice bath and water (1.7 mL) was added dropwise over 20 min. Then 15% NaOH solution (1.7 mL) was added dropwise over 10 min. The suspension was stirred for a further 10 min and water (1.7 mL) was added in one portion and the mixture stirred for 30 min to a give fine white suspension. The suspension was filtered through a pad of Celite® and washed with diethyl ether (2×100 mL). The combined filtrate was concentrated with a bath temperature between 10-13° C. to an orange liquid (5.61 g, 88.0%). LRMS (ESI+) for $C_{18}H_{40}N_2$ (284.3); Found: 285 (MH+).

Benzyl 4-(dodecyl(methyl)amino)-2-methylbutan-2-ylcarbamate

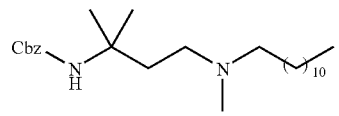

Crude N$^1$-dodecyl-N$^1$,3-dimethylbutane-1,3-diamine (5.61 g, 19.7 mmol) was dissolved into THF (100 mL) and cooled in an ice bath. Solid CbzOSu (4.91 g, 1 equiv, 19.7 mmol) was added to the reaction in one portion. The reaction was left to stir at room temperature for 16 h. The solvent was removed and the residue was taken up in a mixture of ethyl acetate (150 mL) and water (50 mL). The layers were separated and the organic layer washed with 1 M sodium carbonate (2×50 mL) and brine (50 mL). The organic layer was dried over anhydrous MgSO$_4$, filtered and concentrated to a pale yellow oil (8.08 g). The crude oil was purified on an ISCO purification system with gradient elution from 25-100% ethyl acetate in hexanes. The desired fractions were collected and concentrated to give a pale yellow oil (5.71 g, yield: 69.2%). $^1$H NMR (CDCl$_3$, 400 MHz): δ 0.89-0.92 (t, J=6, 3H), 1.21-1.36 (m, 17H), 1.39 (s, 6H), 1.56-1.66 (m, 4H), 2.21 (s, 3H), 2.30-2.34 (t, J=8, 2H), 2.46-2.49 (t, J=6, 2H), 5.06 (s, 2H), 7.28-7.41 (m, 5H). LRMS (ESI+) for C$_{26}$H$_{46}$N$_2$O$_2$ (418.4); Found: 419 (MH+).

N-(3-(Benzyloxycarbonylamino)-3-methylbutyl)-N,N-dimethyldodecan-1-ammonium iodide

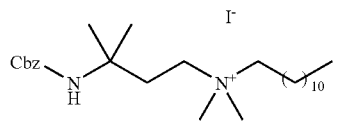

Benzyl 4-(dodecyl(methyl)amino)-2-methylbutan-2-yl-carbamate (4.70 g, 11.2 mmol) was placed into a 50 mL round bottom flask. Methyl iodide (7.0 mL, 10 equiv, 0.112 mol) was added to the reaction in one portion. A stir bar was added and the flask sealed with a wired down septum. The reaction was left to stir at 50° C. for 16 h. The thick suspension was filtered and washed with diethyl ether (3×100 mL) to give a pale yellow powder which was dried under high vacuum (5.71 g, 90.8%). $^1$H NMR (DMSO-d6, 400 MHz): δ 0.84-0.87 (t, J=7, 3H), 1.15-1.30 (m, 24H), 1.53-1.61 (m, 2H), 2.03-2.07 (m, 2H), 2.97 (s, 6H), 3.17-3.21 (m, 4H), 3.33 (s, 3H), 5.00 (s, 2H), 7.16 (bs, 1H), 7.30-7.40 (m, 5H). LRMS (ESI+) for C$_{27}$H$_{49}$N$_2$O$_2^+$ (433.4); Found: 433 (M+).

N-(3-Amino-3-methylbutyl)-N,N-dimethyldodecan-1-ammonium chloride hydrochloride

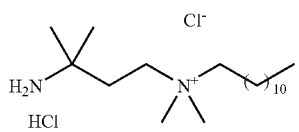

Ag$_2$O (2.25 g, 9.81 mmol) was added in one portion to a solution of N-(3-(benzyloxycarbonylamino)-3-methylbutyl)-N,N-dimethyldodecan-1-ammonium iodide (5.50 g, 1.0 equiv, 9.81 mmol) in a mixture of methanol (75 mL), water (125 mL) and acetic acid (2.0 mL). The black suspension immediately changed to a cream color suspension. The reaction was stirred at room temperature for 30 min. Aqueous 6 N HCl (5 mL) was added to the flask in one portion to give a white cloudy suspension. The suspension was stirred for 15 min, then filtered through a pad of Celite® and the solid was washed with water (2×30 mL). 10% Pd/C (300 mg) was added to the combined filtrate and the flask sealed and degassed with vacuum and flushed with hydrogen from a balloon (3×). The reaction was stirred at room temperature for 17 h. The suspension was filtered through a pad of Celite® and the solid was washed with water (2×50 mL). The filtrate was concentrated to an oil which was dissolved into methanol (25 mL), filtered through a 0.45 micron PTFE frit. The filtrate was concentrated to an oil, dried under high vacuum to give a yellow oil (3.00 g, 82.4%). $^1$H NMR (D$_2$O, 400 MHz): δ 0.74-0.77 (t, J=7, 3H), 1.20-1.30 (m, 18H), 1.32 (s, 6H), 1.60-1.70 (bs, 2H), 2.04-2.08 (m, 2H), 3.00 (s, 6H), 3.21-3.25 (m, 2H), 3.34-3.39 (m, 2H). LRMS (ESI+) for C$_{19}$H$_{43}$N$_2^+$ (299.2); Found: 299 (M+).

N-(3-(Dichloroamino)-3-methylbutyl)-N,N-dimethyldodecan-1-ammonium chloride

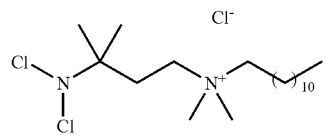

A solution of N-(3-amino-3-methylbutyl)-N,N-dimethyldodecan-1-ammonium chloride hydrochloride (1.80 g, 4.8 mmol) in methanol (100 mL) and was cooled in an ice bath for 15 min. t-BuOCl (1.75 mL, 3 equiv, 14.5 mmol) was added in one portion via syringe to the colorless solution to give a deep yellow solution. The reaction mixture was stirred for 30 min at 0° C., then concentrated under reduced pressure to yield a colorless oil. This oil was dissolved into water and purified via reverse phase chromatography on a Shimadzu Prep-LC utilizing water/acetonitrile and 0.05% acetic acid as modifier. Fractions were collected monitoring UV absorbance at 215 nm. Fractions were pooled and concentrated via rotovap with the water bath set at 25° C. to give a pale yellow solid, (0.579 g, 29.8%). $^1$H NMR (D$_2$O, 400 MHz): δ 0.79-0.82 (t, J=6, 3H), 1.15-1.38 (m, 19H), 1.42 (s, 6H), 1.60-1.70 (m, 2H), 2.13-2.17 (m, 2H), 3.08 (s, 6H), 3.25-3.29 (m, 2H), 3.32-3.36 (t, 2H). LRMS (ESI+) for C$_{19}$H$_{41}$Cl$_2$N$_2^+$ (367.1); Found: 367, 369 (M+, M2H+).

Example 29

Antimicrobial Activity

To determine antimicrobial activity, *Escherichia coli* (ATCC 25922), *Staphylococcus aureus* (ATCC 29213), *Pseudomonas aeruginosa* (ATCC 27853), and *Candida albicans* (ATCC 10231) were used in primary screening. In addition, *Escherichia coli* (MCC 80392), *Staphylococcus aureus* (MCC 91731), *Pseudomonas aeruginosa* (MCC 4438), and *Candida albicans* (MCC 50319), provided by Alcon Laboratories, Fort Worth, Tex., were used. The microbial cultures were diluted in sterile saline pH 4 to prepare inocula. Test compounds were titrated by stepwise two-fold dilutions in sterile saline pH 4. A total of 1.0×10$^5$ to 1.0×10$^6$ Colony Forming Units (CFU)/mL microbe was added to each tube, mixed by gentle vortexing, and then incubated at room temperature for 1 h. Microbial plating on Petri dishes (Tryptic Soy agar or Saboraud's Dextrose agar) was performed immediately after the designated exposure after neutralization of the test article dilutions in Dey-Engley Broth. Plates were incubated at 37° C., and the numbers of microbes were counted by direct colony count to quantitate the surviving microbes as CFU/mL. Positive growth controls were made with sterile 0.9% saline. Compounds were dissolved in unbuffered isotonic saline (SAL) or phosphate buffered saline (PBS) at pH 4 or pH 7 (using HCl and/or NaOH as needed). All compounds were tested three times. The results are tabulated to show the comparison of antimicrobial effectiveness range of the compounds.

Tables 2 and 3 show data obtained according to the method described above for selected compounds. Data shown are the Minimum Bactericidal Concentration (MBC) or Minimum Fungicidal Concentration (MFC) ($\geq$99.9% kill) in µg/mL.

TABLE 2

| Cmpd | E. coli ATCC 25922 pH 4 (Sal) | E. coli ATCC 25922 pH 7 (PBS) | S. aureus ATCC 29213 pH 4 (Sal) | S. aureus ATCC 29213 pH 7 (PBS) | C. albicans ATCC 10231 pH 4 (Sal) | C. albicans ATCC 10231 pH 7 (PBS) |
|---|---|---|---|---|---|---|
| 21-02 | 8 | * | 2 | * | 32 | * |
| 21-14 | 16 | 256 | 2 | * | 32 | * |
| 21-30 | 16 | * | 8 | * | 128 | * |
| 21-32 | 2 | 128 | 2 | 512 | 64 | >4096 |
| 21-48 | 16 | * | 4 | * | * | * |
| 21-78 | 16 | * | 8 | * | 64 | * |
| 21-80 | 2 | * | 4 | * | 32 | * |
| 21-86 | 8 | * | 4 | * | 128 | * |
| 21-90 | 64 | * | 16 | * | 128 | * |
| 21-92 | 8 | * | 4 | * | 32 | * |
| 21-93 | 4 | 512 | 2 | * | * | * |
| 21-106 | 4 | * | 2 | * | >256 | * |
| 21-108 | 8 | * | 2 | * | 256 | * |
| 21-110 | 64 | * | 16 | * | >1024 | * |
| 21-112 | 8 | * | 2 | * | 32 | * |
| 21-114 | 8 | * | 2 | * | 16 | * |
| 21-116 | 4 | * | 2 | * | 32 | * |
| 21-118 | 4 | * | 4 | * | 16 | * |
| 21-120 | 8 | * | 2 | * | 32 | * |
| 21-122 | 16 | * | 4 | * | * | * |
| 21-124 | 8 | * | 2 | * | 64 | * |
| 21-126 | 16 | * | 4 | * | >1024 | * |
| 21-128 | 16 | * | 4 | * | 128 | * |
| 21-130 | 4 | * | 2 | * | 32 | * |
| 21-132 | 4 | * | 2 | * | 32 | * |

TABLE 3

| Cmpd | E. coli MCC 80392 pH 4 (Sal) | E. coli MCC 80392 pH 7 (PBS) | S. aureus MCC 91731 pH 4 (Sal) | S. aureus MCC 91731 pH 7 (PBS) | C. albicans MCC 50319 pH 4 (Sal) | C. albicans MCC 50319 pH 7 (PBS) | P. aeruginosa MCC 4438 pH 4 (Sal) | P. aeruginosa MCC 4438 pH 7 (PBS) |
|---|---|---|---|---|---|---|---|---|
| 21-30 | 16 | 512 | 8 | 512 | 256 | >2048 | * | * |
| 21-32 | 8 | 256 | 1 | 256 | 32 | >1024 | * | 512 |
| 21-80 | 4 | 256 | 4 | >256 | 64 | >512 | 4 | >256 |
| 21-114 | 2 | 512 | 4 | 512 | * | * | 4 | 1024 |

Example 30

Cytotoxicity

Cytotoxicity was assessed by a colorimetric assay system using the Dojindo™ cell counting kit containing 2-(2-methoxy-4-nitrophenyl)-3-(4-nitrophenyl)-5-(2,4-disulfophenyl)-2H-tetrazolium, monosodium salt (WST-8). In this assay, the WST-8 reagent was bioreduced by cellular dehydrogenases to a formazan product that is highly soluble in tissue culture medium. The orange formazan, which is produced only by live cells, is a direct measure of cell viability and can be read spectrophotometrically (e.g., evaluation of a soluble tetrazolium/formazan assay for cell growth and drug sensitivity in culture using human and other tumor cell lines is described by D. A. Scudiero et al., Cancer Res., 48(17), 4827-33 (1988). Similar approaches for determining the cell viability are known in the art.

In a standard assay, mouse fibroblast cells (ATCC CCL-1, L929), were cultured in Minimum Essential Medium, α-medium supplemented with 10% heat inactivated fetal bovine serum, L-glutamine, penicillin and streptomycin. Cells were trypsinized and counted under the microscope and seeded at $1.5 \times 10^4$ total cells per 100 µL per well of a flat-bottom 96-well plate in order to achieve ~80% confluence after overnight incubation at 37° C. On the day of the assay, the tissue culture medium was removed and replaced with 30 µL of fresh medium.

Test articles were prepared as 2-fold serial dilutions and 170 µL of each dilution is added into each of 4-wells (total volume per well=200 µL). The test plate was then returned to the 37° C. incubator for 60 min. Immediately after the exposed time, test article from each well was replaced with 200 µL of fresh media. Plates were incubated at 37° C. for 18-20 hours. The following day growth medium was replaced with 100 µL/well of fresh medium containing 10 µL WST-8 reagent. Cells were incubated under growth conditions (5% $CO_2$ at 37° C. humidified incubator), protected from light, until color development was achieved (usually 1-4 hours). Absorbance was read at 450 nm with reference wavelength at 750 nm using Molecular Device SpectraMax M5 plate reader. Untreated or vehicle only treated cells receiving WST-8 reagent served as positive cell proliferation controls.

Table 4 shows data ($CT_{50}$, in mM) obtained according to the method described above for selected compounds. The $CT_{50}$ value for each compound was calculated from the absorbance values ($A_{450/750}$) and is defined as the concentration of test article that results in survival of 50% of the cells following treatment. The absorbance $A_{450/750}$ from each well of untreated cells and from each well within the dilution series was measured. To calculate the $CT_{50}$ for each compound, all compound concentrations were first log-transformed using GraphPad Prism4 (ver 4.03) software. Next, a non-linear regression (curve fit) analysis was performed on all the absorbance data measured from the dilution series, including the absorbance data obtained from wells of the untreated control cells. For each dilution within the dilution series, an average $A_{450/750}$ was calculated from the four replicate wells. The average $A_{450/750}$ data were plotted on a y-axis against the log-transformed compound concentration on the x-axis, and the $CT_{50}$ value calculated from the resulting best-fit curve.

TABLE 4

| Cmpd | L929 cells | | |
|---|---|---|---|
| | pH 4 (Sal) | pH 4 (Acetate) | pH 7 (PBS) |
| 21-02 | <0.03 | * | * |
| 21-30 | 0.5 | * | 0.5 |
| 21-32 | 1.7 | * | 1.8 |
| 21-80 | 0.9 | * | * |
| 21-86 | * | * | 0.6 |
| 21-110 | 0.9 | * | * |
| 21-112 | 1.4 | * | * |
| 21-114 | 1.3 | * | * |
| 21-116 | 3.0 | * | * |
| 21-118 | 0.9 | * | * |
| 21-120 | * | 1.3 | * |
| 21-122 | * | 1.0 | * |
| 21-124 | * | 1.0 | * |
| 21-126 | * | 0.6 | * |
| 21-128 | * | 1.3 | * |
| 21-134 | * | 1.4 | * |
| 21-138 | * | 0.5 | * |

While the foregoing description describes specific embodiments, those with orinary skill in the art will appreciate that various modifications and alternatives can be developed. Accordingly, the particular embodiments described above are meant to be illustrative only, and not to limit the scope of the invention, which is to be given the full breadth of the appended claims, and any and all equivalents thereof.

What is claimed is:

1. A compound of Formula I

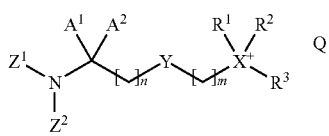

or a salt thereof, wherein:
n is an integer from 0 to 12;
m is an integer from 1 to 12;
$Z^1$ is Cl or Br;
$Z^2$ is H, Cl or Br;
Y is a single bond, or is selected from the group consisting of —$CF_2$—, —CHF—, —C($CF_3$)H—, and —C(=O)—,
X is N, P or S;
$A^1$ and $A^2$ are each independently selected from the group consisting of alkyl, aryl, cycloalkyl, heteroalkyl, heteroaryl, and heterocycloalkyl, each of which may be optionally substituted; or $A^1$ and $A^2$ together with the carbon atom to which they are attached form a cycloalkyl or heterocycloalkyl group, each of which may be optionally substituted;
$R^1$ and $R^2$ are each independently selected from the group consisting of alkyl, aryl, cycloalkyl, heteroalkyl, heteroaryl, and heterocycloalkyl, each of which may be optionally substituted; or $R^1$ and $R^2$ together with the X atom to which they are attached form an optionally substituted heterocycloalkyl group;
$R^3$ is alkyl, aryl, cycloalkyl, heteroalkyl, heteroaryl or heterocycloalkyl, each of which may be optionally substituted, and may further be O when X is N;
$R^a$, $R^b$, $R^c$ and $R^d$ are each independently selected from the group consisting of hydrogen, alkyl, aryl, cycloalkyl, heteroalkyl, heteroaryl and heterocycloalkyl, each of which may be optionally substituted; and
Q is a counter ion or absent;
with the proviso that $R^3$ is absent when X is S.

2. The compound of claim 1, wherein n is 1, 2 or 3.
3. The compound of claim 1, wherein m is 1, 2 or 3.
4. The compound of claim 1, wherein $Z^1$ and $Z^2$ are both Cl.
5. The compound of claim 1, wherein $Z^1$ is Cl and $Z^2$ is H.
6. The compound of claim 1, wherein Y is a single bond.
7. The compound of claim 1, wherein Y is selected from the group consisting of —$CF_2$—, —CHF—, —C($CF_3$)H—, and —C(=O)—.
8. The compound of claim 1, wherein X is N.
9. The compound of claim 1, wherein $R^1$, $R^2$ and $R^3$ are each independently selected from the group consisting of alkyl and aryl, each of which may be optionally substituted.
10. The compound of claim 1, wherein $R^1$ and $R^2$ together with the X atom to which they are attached form an optionally substituted heterocycloalkyl group, and $R^3$ is an optionally substituted alkyl or aryl.
11. A compound of Formula IB

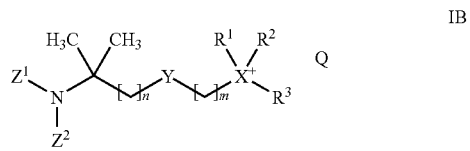

or a salt thereof, wherein:
n is an integer from 0 to 12;
m is an integer from 1 to 12;
$Z^1$ is Cl or Br;
$Z^2$ is H, Cl or Br;
Y is a single bond or is selected from the group consisting of —$CF_2$—, —CHF—, —C($CF_3$)H—, and —C(=O)—,
X is N, P or S;
$R^1$ and $R^2$ are each independently selected from the group consisting of alkyl, aryl, cycloalkyl, heteroalkyl, heteroaryl and heterocycloalkyl, each of which may be optionally substituted; or $R^1$ and $R^2$ together with the X atom to which they are attached form an optionally substituted heterocycloalkyl group;
$R^3$ is alkyl, aryl, cycloalkyl, heteroalkyl, heteroaryl or heterocycloalkyl, each of which may be optionally substituted, and may further be O when X is N;
$R^a$, $R^b$, $R^c$ and $R^d$ are each independently selected from the group consisting of hydrogen, alkyl, aryl, cycloalkyl, heteroalkyl, heteroaryl and heterocycloalkyl, each of which may be optionally substituted; and
Q is a counter ion or absent;
with the proviso that $R^3$ is absent when X is S.

12. The compound of claim 11, wherein X is N.
13. The compound of claim 11, wherein $Z^1$ and $Z^2$ are both Cl.
14. The compound of claim 11, wherein $Z^1$ is Cl and $Z^2$ is H.
15. The compound of claim 11, wherein:
n is 1, 2 or 3;
m is 1, 2 or 3;
$Z^1$ is Cl;
$Z^2$ is H or Cl;
Y is a single bond or is selected from the group consisting of —$CF_2$—, —CHF—, —C($CF_3$)H—, and —C(=O)—, R¹ and R² are each independently optionally substituted alkyl, or R¹ and R² together with the X atom to which they are attached form an optionally substituted heterocycloalkyl group; and R³ is optionally substituted alkyl.

16. A compound selected from the group consisting of:

2-(chloroamino)-N,N,N,2-tetramethylpropan-1-ammonium chloride;
2-(dichloroamino)-N,N,N,2-tetramethylpropan-1-ammonium chloride;
3-(chloroamino)-N,N,N,3-tetramethylbutan-1-ammonium chloride;
3-(dichloroamino)-N,N,N,3-tetramethylbutan-1-ammonium chloride;
2-(chloroamino)-N-(fluoromethyl)-N,N,2-trimethylpropan-1-ammonium chloride;
2-(dichloroamino)-N-(fluoromethyl)-N,N,2-trimethylpropan-1-ammonium chloride;
3-(chloroamino)-N-(fluoromethyl)-N,N,3-trimethylbutan-1-ammonium chloride;
3-(dichloroamino)-N-(fluoromethyl)-N,N,3-trimethylbutan-1-ammonium chloride;
2-(chloroamino)-N,N,2-trimethyl-N-(2,2,2-trifluoroethyl)propan-1-ammonium chloride;
2-(dichloroamino)-N,N,2-trimethyl-N-(2,2,2-trifluoroethyl)propan-1-ammonium chloride;
3-(chloroamino)-N,N,3-trimethyl-N-(2,2,2-trifluoroethyl)butan-1-ammonium chloride;
3-(dichloroamino)-N,N,3-trimethyl-N-(2,2,2-trifluoroethyl)butan-1-ammonium chloride;
N-(2-(chloroamino)-2-methylpropyl)-3,3,3-trifluoro-N,N-dimethylpropan-1-ammonium chloride;
N-(2-(dichloroamino)-2-methylpropyl)-3,3,3-trifluoro-N,N-dimethylpropan-1-ammonium chloride;
3-(chloroamino)-N,N,3-trimethyl-N-(3,3,3-trifluoropropyl)butan-1-aminium chloride;
3-(dichloroamino)-N,N,3-trimethyl-N-(3,3,3-trifluoropropyl)butan-1-aminium chloride;
N-butyl-N-(2-(chloroamino)-2-methylpropyl)-N-methylbutan-1-ammonium chloride;
N-butyl-N-(2-(dichloroamino)-2-methylpropyl)-N-methylbutan-1-ammonium chloride;
N,N-dibutyl-3-(chloroamino)-N,3-dimethylbutan-1-ammonium chloride;
N,N-dibutyl-3-(dichloroamino)-N,3-dimethylbutan-1-ammonium chloride;
N,N-dibutyl-N-(2-(chloroamino)-2-methylpropyl)butan-1-ammonium chloride;
N,N-dibutyl-N-(2-(dichloroamino)-2-methylpropyl)butan-1-ammonium chloride;
N,N,N-tributyl-3-(chloroamino)-3-methylbutan-1-ammonium chloride;
N,N,N-tributyl-3-(dichloroamino)-3-methylbutan-1-ammonium chloride;
N-(2-(chloroamino)-2-methylpropyl)-3-fluoro-N,N-dimethylbenzenaminium chloride;
N-(2-(dichloroamino)-2-methylpropyl)-3-fluoro-N,N-dimethylbenzenaminium chloride;
N-(3-(chloroamino)-3-methylbutyl)-3-fluoro-N,N-dimethylbenzenaminium chloride;
N-(3-(dichloroamino)-3-methylbutyl)-3-fluoro-N,N-dimethylbenzenaminium chloride;
5-(chloroamino)-3-fluoro-N,N,N,5-tetramethylhexan-1-ammonium chloride;
5-(dichloroamino)-3-fluoro-N,N,N, 5-tetramethylhexan1-ammonium chloride;
5-(chloroamino)-3,3-difluoro-N,N,N,5-tetramethylhexan-1-ammonium chloride;
5-(dichloroamino)-3,3-difluoro-N,N,N,5-tetramethylhexan-1-ammonium chloride;
6-(chloroamino)-3-fluoro-N,N,N, 6-tetramethylheptan-1-ammonium chloride;
6-(dichloroamino)-3-fluoro-N,N,N, 6-tetramethylheptan-1-ammonium chloride;
6-(chloroamino)-3,3-difluoro-N,N,N,6-tetramethylheptan-1-ammonium chloride;
6-(dichloroamino)-3,3-difluoro-N,N,N,6-tetramethylheptan-1-ammonium chloride;
N-(2-(chloroamino)-2-methylpropyl)-N,N-dimethyl-3-(trifluoromethy)benzenammonium chloride;
N-(2-(dichloroamino)-2-methylpropyl)-N,N-dimethyl-3-(trifluoromethyl)benzenammonium chloride;
N-(3-(chloroamino)-3-methylbutyl)-N,N-dimethyl-3-(trifluoromethyl)benzenammonium chloride;
N-(3-(dichloroamino)-3-methylbutyl)-N,N-dimethyl-3-(trifluoromethyl)benzenammonium chloride;
N-(2-(chloroamino)-2-methylpropyl)-N,N-dimethyl-5-(trifluoromethyl) pyridin-2-ammonium chloride;
N-(2-(dichloroamino)-2-methylpropyl)-N,N-dimethyl-5-(trifluoromethyl)pyridin-2-ammonium chloride;
N-(3-(chloroamino)-3-methylbutyl)-N,N-dimethyl-5-(trifluoromethyl) pyridin-2-ammonium chloride;
N-(3-(dichloroamino)-3-methylbutyl)-N,N-dimethyl-5-(trifluoromethyl)pyridin-2-ammonium chloride;
4-(2-(chloroamino)-2-methylpropyl)-4-methylmorpholin-4-ium chloride;
4-(2-(dichloroamino)-2-methylpropyl)-4-methylmorpholin-4-ium chloride;
4-(3-(chloroamino)-3-methylbutyl)-4-methylmorpholin-4-ium chloride;
4-(3-(dichloroamino)-3-methylbutyl)-4-methylmorpholin-4-ium chloride;
1-(2-(chloroamino)-2-methylpropyl)-1-methylpiperidinium chloride;
1-(2-(dichloroamino)-2-methylpropyl)-1-methylpiperidinium chloride;
1-(3-(chloroamino)-3-methylbutyl)-1-methylpiperidinium chloride;
1-(3-(dichloroamino)-3-methylbutyl)-1-methylpiperidinium chloride;
(2-(chloroamino)-2-methylpropyl) trimethylphosphonium chloride;
(2-(dichloroamino)-2-methylpropyl) trimethylphosphonium chloride;
(3-(chloroamino)-3-methylbutyl) trimethylphosphonium chloride;
(3-(dichloroamino)-3-methylbutyl) trimethylphosphonium chloride;
(2-(chloroamino)-2-methylpropyl) dimethylsulfonium chloride;
(2-(dichloroamino)-2-methylpropyl) dimethylsulfonium chloride;
(3-(chloroamino)-3-methylbutyl)dimethylsulfonium chloride;
(3-(dichloroamino)-3-methylbutyl)dimethylsulfonium chloride;
2-((2-(chloroamino)-2-methylpropyl)dimethylammonio) ethanesulfonate;
2-((2-(dichloroamino)-2-methylpropyl) dimethylammonio)ethanesulfonate;
2-(4-(2-(chloroamino)propan-2-yl)-1H-1,2,3-triazol-1-yl)-N,N,N-trimethylethanaminium chloride;

2-(4-(2-(dichloroamino)propan-2-yl)-1H-1,2,3-triazol-1-yl)-N,N,N-trimethylethanaminium chloride;
1-(2-(3-(dichloroamino)-3-methylbutanoyloxy)ethyl)-1-methylpiperidinium chloride;
1-(2-(3-(chloroamino)-3-methylbutanoyloxy)ethyl)-1-methylpiperidinium chloride;
5-(dichloroamino)-3-hydroxy-N,N,N,5-tetramethylhexan-1-aminium chloride;
5-(chloroamino)-3-hydroxy-N,N,N,5-tetramethylhexan-1-aminium chloride;
6-(dichloroamino)-4-hydroxy-N,N,N,6-tetramethylheptan-1-aminium chloride;
6-(dichloroamino)-4-hydroxy-N,N,N,6-tetramethylheptan-1-aminium chloride;
6-(dichloroamino)-4-fluoro-N,N,N,6-tetramethylheptan-1-aminium chloride;
6-(chloroamino)-4-fluoro-N,N,N,6-tetramethylheptan-1-aminium chloride;
1-(3-(dichloroamino)-3-methylbutyl)pyridinium chloride;
1-(3-(chloroamino)-3-methylbutyl)pyridinium chloride;
1-(4-(dichloroamino)-4-methylpentyl)pyridinium chloride;
1-(4-(chloroamino)-4-methylpentyl)pyridinium chloride;
(4-(chloroamino)-4-methylpentyl)trimethylphosphonium chloride;
(4-(dichloroamino)-4-methylpentyl)trimethylphosphonium chloride;
4-(chloroamino)-N,N,N-4-tetramethylpentan-1-ammonium chloride;
4-(dichloroamino)-N,N,N-4-tetramethylpentan-1-ammonium chloride;
4-acetyl-1-(2-(chloroamino)-2-methylpropyl)-1-methylpiperazin-1-ium chloride;
4-acetyl-1-(2-(dichloroamino)-2-methylpropyl)-1-methylpiperazin-1-ium chloride;
3-(3-(chloroamino)-3-methylbutylsulfonyl)-N,N,N-trimethylpropan-1-ammonium chloride;
3-(3-(dichloroamino)-3-methylbutylsulfonyl)-N,N,N-trimethylpropan-1-ammonium chloride;
3-(chloroamino)-N,N-diethyl-N-3-dimethylbutan-1-ammonium chloride;
3-(dichloroamino)-N,N-diethyl-N-3-dimethylbutan-1-ammonium chloride;
1-(3-(chloroamino)-3-methylbutyl)-4,4-difluoro-1-methylpiperidinium chloride;
1-(3-(Dichloroamino)-3-methylbutyl)-4,4-difluoro-1-methylpiperidinium chloride;
1-(3-(chloroamino)-3-methylbutyl)-1-methylazepanium chloride;
1-(3-(dichloroamino)-3-methylbutyl)-1-methylazepanium chloride;
1-(3-(chloroamino)-3-methylbutyl)-1-azoniabicyclo[2.2.2]octane methanesulfonate;
1-(3-(dichloroamino)-3-methylbutyl)-1-azoniabicyclo[2.2.2]octane methanesulfonate;
1-(3-(chloroamino)-3-methylbutyl)-1,4,4-trimethylpiperidinium chloride;
1-(3-(dichloroamino)-3-methylbutyl)-1,4,4-trimethylpiperidinium chloride;
N-butyl-3-(chloroamino)-N,N,3-trimethylbutan-1-ammonium chloride;
N-butyl-3-(dichloroamino)-N,N,3-trimethylbutan-1-ammonium chloride;
N-(3-(chloroamino)-3-methylbutyl)-N,N-dimethylcyclohexanammonium chloride;
N-(3-(dichloroamino)-3-methylbutyl)-N,N-dimethylcyclohexanammonium chloride;
N1-(3-(chloroamino)-3-methylbutyl)-N1,N1,N3,N3,N3-pentamethylpropane-1,3-diammonium chloride;
N1-(3-(dichloroamino)-3-methylbutyl)-N1,N1,N3,N3,N3-pentamethylpropane-1,3-diammonium chloride;
1-(3-(chloroamino)-3-methylbutyl)-1-methylpyrrolidinium chloride;
1-(3-(dichloroamino)-3-methylbutyl)-1-methylpyrrolidinium chloride;
3-(chloroamino)-N,N,3-trimethyl-N-(2,2,2-trifluoroethyl)butan-1-ammonium chloride;
3-(dichloroamino)-N,N,3-trimethyl-N-(2,2,2-trifluoroethyl)butan-1-ammonium chloride;
3-(chloroamino)-N-ethyl-N,N,3-trimethylbutan-1-aminium chloride;
3-(dichloroamino)-N-ethyl-N,N,3-trimethylbutan-1-aminium chloride;
N-(3-(chloroamino)-3-methylbutyl)-N,N-dimethylhexan-1-aminium chloride;
N-(3-(dichloroamino)-3-methylbutyl)-N,N-dimethylhexan-1-aminium chloride;
N-(3-(chloroamino)-3-methylbutyl)-N,N-dimethyldodecan-1-aminium chloride;
N-(3-(dichloroamino)-3-methylbutyl)-N,N-dimethyldodecan-1-aminium chloride;
4-(chloroamino)-N,N,N-trimethyl-4-propylheptan-1-aminium;
4-(dichloroamino)-N,N,N-trimethyl-4-propylheptan-1-aminium;
3-(1-(chloroamino)cyclohexyl)-N,N,N-trimethylpropan-1-aminium;
3-(1-(dichloroamino)cyclohexyl)-N,N,N-trimethylpropan-1-aminium;
3-(1-(chloroamino)cyclopentyl)-N,N,N-trimethylpropan-1-aminium; and
3-(1-(dichloroamino)cyclopentyl)-N,N,N-trimethylpropan-1-aminium, or a salt thereof.

17. The compound of claim 1 wherein the salt is a pharmaceutically acceptable salt.

18. A composition comprising a compound of claim 1 and a pharmaceutically acceptable carrier.

19. An antimicrobial composition comprising a compound of claim 1 and a pharmaceutically acceptable carrier or excipient, formulated as an aerosol, cream, emulsion, gel, lotion, ointment, paste, powder, solid, solution or suspensions.

20. A method for treating a microbial ailment, condition or infection in a patient, comprising administering an effective amount of a compound of claim 1 to the patient.

21. A method of treating a microbial infection of skin, nail, hair, or a mucous membrane comprising administering an effective amount of a compound of claim 1 to or near the infected area.

22. A method of treating a microbial infection of the upper respiratory tract, comprising administering an effective amount of a compound of claim 1 to or near the infected area.

23. A method for treating or disinfecting a surface, comprising applying an effective amount of a compound of claim 1 to the surface.

24. The method of claim 23, wherein the surface is a surface of a medical device.

25. The method of claim 24, wherein the medical device is selected from the group consisting of catheters, breathing tubes, contact lenses, dental implants and equipment, equipment used for organ preservation, hearing aids, prostheses and stents.

* * * * *